US 7,009,044 B1

(12) United States Patent
Nam et al.

(10) Patent No.: US 7,009,044 B1
(45) Date of Patent: Mar. 7, 2006

(54) HCV/BVDV CHIMERIC GENOMES AND USES THEREOF

(75) Inventors: Jae-Hwan Nam, GuyngGi-Do (KR); Jens Bukh, Bethesda, MD (US); Suzanne U. Emerson, Gaithersburg, MD (US); Robert H. Purcell, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/009,011

(22) PCT Filed: Feb. 6, 2000

(86) PCT No.: PCT/US00/15527

§ 371 (c)(1),
(2), (4) Date: Jul. 19, 2002

(87) PCT Pub. No.: WO00/75352

PCT Pub. Date: Dec. 14, 2000

Related U.S. Application Data

(60) Provisional application No. 60/137,817, filed on Jun. 4, 1999.

(51) Int. Cl.
*C07H 21/00* (2006.01)
*C12N 7/00* (2006.01)
*C12N 7/01* (2006.01)
*C12N 15/09* (2006.01)
*C12N 15/34* (2006.01)

(52) U.S. Cl. .............. 536/23.72; 536/23.1; 536/23.7; 435/235.1; 435/239; 435/69.1; 435/320.1

(58) Field of Classification Search ............ 424/184.1, 424/185.1, 186.1, 204.1, 205.1, 218.1, 228.1, 424/93.1, 93.2, 93.6, 189.1, 199.1, 202.1; 435/5, 235.1, 236, 239, 455, 456, 457, 320.1, 435/69.1, 69.3, 7.1; 536/23.1, 23.7, 23.72, 536/24.1, 24.2

See application file for complete search history.

(56) References Cited

U.S. PATENT DOCUMENTS 6,326,137 B1 * 12/2001 Hong et al. .................... 435/5

FOREIGN PATENT DOCUMENTS

| EP | WO 96/04385 | * | 2/1996 |
| WO | WO 98/37911 | * | 9/1998 |
| WO | WO 99/55366 | | 11/1999 |

OTHER PUBLICATIONS

Nam et al., Journal of Virological Methods, vol. 97 No. 1-2, pp. 113-123 (Sep. 2001).*
Vassilev et al., Journal of Virology, vol. 71 No. 1, pp. 471-478 (Jan. 1997).*
Kashiwakuma et al., Journal of Immunological Methods, vol. 190 No. 1, pp. 79-89 (Mar. 1996).*
Frolov, I et al, "Cis-Acting RNA Elements Required for Replication of Bovine Viral Diarrhea Virus-Hepatitius C Virus 5' Non-translated Region Chimeras" RNA, Cambridge University Press, Cambridge, GB 4:11 (pp. 1418-1435) Nov. 1998.
Lu, H. et al, "Poliovirus chimeras replicating under the translation control of genetic elements of HCV reveal unusual properties of the IRES of HCV" PNAS, NAS 93 (pp. 1412-1417) Feb. 1996.
Venugopal, K. and Gould, E.A., "Towards a new generation of Flavivirus Vaccines" Vaccine 2:11 (pp. 966-975) 1994.
Meyers, G. et al, "Recovery of Cytopathogenic and Non-Cytopathogenic Bovine Viral Diarrhea Viruses from cDNA Constructs" Journal of Virology, The AMerican Society for Microbiology 70:12 (pp. 8606-8613) Dec. 1996.
Yu, H. et al, "Sequence and Structural Elements at the 3' Terminus of Bovine Viraldiarrhea Virus Genomic RNA: Functional Role During RNA Replication" Journal of Virology, The American Society for Microbiology 73:5 (pp. 3638-3648) May 1999.
Lai, VC; Zhong, W.; Skelton, A.; Ingravallo, P.; Vassilev, V.; Donis, RO.; Hong, Z.; and Lau JY, "Generation and characterization of a hepatitis C virus NS3 protease-dependent bovine viral diarrhea virus." Journal of Virology 74:14 (pp. 6339-6347) Jul. 2000.

* cited by examiner

Primary Examiner—James C. Housel
Assistant Examiner—Zachariah Lucas
(74) Attorney, Agent, or Firm—Knobbe, Martens, Olson & Bear, LLP

(57) ABSTRACT

The present invention relates to molecular approaches to the production of nucleic acid sequences which comprise the genomes of chimeric hepatitis C virus-bovine viral diarrhea viruses (HCV/BVDV). The invention also relates to the use of these chimeric nucleic acid sequences to produce chimeric virions in cells and the use of these chimeric virions in HCV antibody neutralization assays, and for the development of vaccines and therapeutics for HCV.

15 Claims, 19 Drawing Sheets

H77C

|  | 10 | 20 | 30 | 40 | 50 |  |
|---|---|---|---|---|---|---|
|  | 1234567890 | 1234567890 | 1234567890 | 1234567890 | 1234567890 |  |
|  | GCCAGCCCCC | TGATGGGGGC | GACACTCCAC | CATGAATCAC | TCCCCTGTGA | 50 |
|  | GGAACTACTG | TCTTCACGCA | GAAAGCGTCT | AGCCATGGCG | TTAGTATGAG | 100 |
|  | TGTCGTGCAG | CCTCCAGGAC | CCCCCCTCCC | GGAGAGCCA | TAGTGGTCTG | 150 |
|  | CGGAACCGGT | GAGTACACCG | GAATTGCCAG | GACGACCGGG | TCCTTTCTTG | 200 |
|  | GATAAACCCG | CTCAATGCCT | GGAGATTTGG | GCGTGCCCCC | GCAAGACTGC | 250 |
|  | TAGCCGAGTA | GTGTTGGGTC | GCGAAAGGCC | TTGTGGTACT | GCCTGATAGG | 300 |
|  | GTGCTTGCGA | GTGCCCCGGG | AGGTCTCGTA | GACCGTGCAC | CATGAGCACG | 350 |
|  | AATCCTAAAC | CTCAAAGAAA | AACCAAACGT | AACACCAACC | GTCGCCCACA | 400 |
|  | GGACGTCAAG | TTCCCGGGTG | GCGGTCAGAT | CGTTGGTGGA | GTTTACTTGT | 450 |
|  | TGCCGCGCAG | GGGCCCTAGA | TTGGGTGTGC | GCGCGACGAG | GAAGACTTCC | 500 |
|  | GAGCGGTCGC | AACCTCGAGG | TAGACGTCAG | CCTATCCCA | AGGCAGGTCG | 550 |
|  | GCCCGAGGGC | AGGACCTGGG | CTCAGCCCGG | GTACCCTTGG | CCCTCTATG | 600 |
|  | GCAATGAGGG | TTGCGGGTCG | GCGGGATGGC | TCCTGTCTCC | CCGTGGCTCT | 650 |
|  | CGGCCTAGCT | GGGGCCCAC | AGACCCCCGG | CGTACGTCGC | GCAATTTGGG | 700 |
|  | TAAGGTCATC | GATACCCTTA | CGTGCGGCTT | CGCCGACCTC | ATGGGGTACA | 750 |
|  | TACCGCTCGT | CGGCGCCCCT | CTTGGAGCCG | CTGCCAGGCC | CCTGGCGCAT | 800 |
|  | GGCGTCCGGG | TTCTGGAAGA | CGGCGTGAAC | TATGCAACAG | GGAACCTTCC | 850 |
|  | TGGTTGCTCT | TTCTCTATCT | TCCTTCTGGC | CCTGCTCTCT | TGCCTGACTG | 900 |
|  | TGCCCGCTTC | AGCCTACCAA | GTGCGCAATT | CCTCGGGCT | TTACCATGTC | 950 |
|  | ACCAATGATT | GCCCTAACTC | GAGTATTGTG | TACGAGGCGG | CCGATGCCAT | 1000 |
|  | CCTGCACACT | CCGGGGTGTG | TCCCTTGCGT | TCGCGAGGGT | AACGCCTCGA | 1050 |
|  | GGTGTTGGGT | GGCGGTGACC | CCCACGGTGG | CCACCAGGGA | CGGCAAACTC | 1100 |
|  | CCCACAACGC | AGCTTCGACG | TCATATCGAT | CTGCTTGTCG | GGAGCGCCAC | 1150 |
|  | CCTCTGCTCG | GCCCTCTACG | TGGGGGACCT | GTGCGGGTCT | GTCTTTCTTG | 1200 |
|  | TTGGTCAACT | GTTTACCTTC | TCTCCCAGGC | GCCACTGGAC | GACGCAAGAC | 1250 |
|  | TGCAATTGTT | CTATCTATCC | CGGCCATATA | AGGGTCATC | GCATGGCATG | 1300 |
|  | GGATATGATG | ATGAACTGGT | CCCCTACGGC | AGCGTTGGTG | GTAGCTCAGC | 1350 |
|  | TGCTCCGGAT | CCCACAAGCC | ATCATGGACA | TGATCGCTGG | TGCTCACTGG | 1400 |
|  | GGAGTCCTGG | CGGGCATAGC | GTATTTCTCC | ATGGTGGGA | ACTGGGCGAA | 1450 |
|  | GGTCCTGGTA | GTGCTGCTGC | TATTTGCCGG | CGTCGACGCG | GAAACCCACG | 1500 |
|  | TCACCGGGGG | AAATGCCGGC | CGCACCACGG | CGGGCTTGT | TGGTCTCCTT | 1550 |
|  | ACACCAGGCG | CCAAGCAGAA | CATCCAACTG | ATCAACACCA | ACGGCAGTTG | 1600 |
|  | GCACATCAAT | AGCACGGCCT | TGAATTGCAA | TGAAAGCCTT | AACACCGGCT | 1650 |
|  | GGTTAGCAGG | GCTCTTCTAT | CAACACAAAT | TCAACTCTTC | AGGCTGTCCT | 1700 |
|  | GAGAGGTTGG | CCAGCTGCCG | ACGCCTTACC | GATTTTGCCC | AGGGCTGGGG | 1750 |
|  | TCCTATCAGT | TATGCCAACG | GAAGCGGCCT | CGACGAACGC | CCCTACTGCT | 1800 |
|  | GGCACTACCC | TCCAAGACCT | TGTGGCATTG | TGCCCGCAAA | GAGCGTGTGT | 1850 |
|  | GGCCCGGTAT | ATTGCTTCAC | TCCCAGCCCC | GTGGTGGTGG | AACGACCGA | 1900 |

```
         10         20         30         40         50
1234567890 1234567890 1234567890 1234567890 1234567890
CAGGTCGGGC GCGCCTACCT ACAGCTGGGG TGCAAATGAT ACGGATGTCT  1950
TCGTCCTTAA CAACACCAGG CCACGGCTGG GCAATTGGTT CGGTTGTACC  2000
TGGATGAACT CAACTGGATT CACCAAAGTG TGCGGAGCGC CCCCTTGTGT  2050
CATCGGAGGG GTGGGCAACA ACACCTTGCT CTGCCCCACT GATTGCTTCC  2100
GCAAACATCC GGAAGCCACA TACTCTCGGT GCGGCTCCGG TCCCTGGATT  2150
ACACCCAGGT GCATGGTCGA CTACCCGTAT AGGCTTTGGC ACTATCCTTG  2200
TACCATCAAT TACACCATAT TCAAAGTCAG GATGTACGTG GGAGGGGTCG  2250
AGCACAGGCT GGAAGCGGCC TGCAACTGGA CGCGGGGCGA ACGCTGTGAT  2300
CTGGAAGACA GGGACAGGTC CGAGCTCAGC CCGTTGCTGC TGTCCACCAC  2350
ACAGTGGCAG GTCCTTCCGT GTTCTTTCAC GACCCTGCCA GCCTTGTCCA  2400
CCGGCCTCAT CCACCTCCAC CAGAACATTG TGGACGTGCA GTACTTGTAC  2450
GGGGTAGGGT CAAGCATCGC GTCCTGGGCC ATTAAGTGGG AGTACGTCGT  2500
TCTCCTGTTC CTTCTGCTTG CAGACGCGCG CGTCTGCTCC TGCTTGTGGA  2550
TGATGTTACT CATATCCCAA GCGGAGGCGG CTTGGAGAA CCTCGTAATA  2600
CTCAATGCAG CATCCCTGCC CGGACGCAC GGTCTTGTGT CCTTCCTCGT  2650
GTTCTTCTGC TTTGCGTGGT ATCTGAAGGG TAGGTGGGTG CCCGGAGCGG  2700
TCTACGCCCT CTACGGGATG TGGCCTCTCC TCCTGCTCCT GCTGGCGTTG  2750
CCTCAGCGGG CATACGCACT GGACACGGAG GTGGCCGCGT CGTGTGGCGG  2800
CGTTGTTCTT GTCGGGTTAA TGGCGCTGAC TCTGTCGCCA TATTACAAGC  2850
GCTATATCAG CTGGTGCATG TGGTGGCTTC AGTATTTTCT GACCAGAGTA  2900
GAAGCGCAAC TGCACGTGTG GGTTCCCCCC CTCAACGTCC GGGGGGGGCG  2950
CGATGCCGTC ATCTTACTCA TGTGTGTAGT ACACCCGACC CTGGTATTTG  3000
ACATCACCAA ACTACTCCTG GCCATCTTCG GACCCCTTTG GATTCTTCAA  3050
GCCAGTTTGC TTAAAGTCCC CTACTTCGTG CGCGTTCAAG GCCTTCTCCG  3100
GATCTGCGCG CTAGCGCGGA AGATAGCCGG AGGTCATTAC GTGCAAATGG  3150
CCATCATCAA GTTAGGGGCG CTTACTGGCA CCTATGTGTA TAACCATCTC  3200
ACCCCTCTTC GAGACTGGGC GCACAACGGC CTGCGAGATC TGGCCGTGGC  3250
TGTGGAACCA GTCGTCTTCT CCCGAATGGA GACCAAGCTC ATCACGTGGG  3300
GGGCAGATAC CGCCGCGTGC GGTGACATCA TCAACGGCTT GCCCGTCTCT  3350
GCCCGTAGGG GCCAGGAGAT ACTGCTTGGG CCAGCCGACG GAATGGTCTC  3400
CAAGGGGTGG AGGTTGCTGG CGCCCATCAC GGCGTACGCC CAGCAGACGA  3450
GAGGCCTCCT AGGGTGTATA ATCACCAGCC TGACTGGCCG GGACAAAAAC  3500
CAAGTGGAGG GTGAGGTCCA GATCGTGTCA ACTGCTACCC AAACCTTCCT  3550
GGCAACGTGC ATCAATGGGG TATGCTGGAC TGTCTACCAC GGGCCGGAA  3600
CGAGGACCAT CGCATCACCC AAGGGTCCTG TCATCCAGAT GTATACCAAT  3650
GTGGACCAAG ACCTTGTGGG CTGGCCCGCT CCTCAAGGTT CCCGCTCATT  3700
GACACCCTGT ACCTGCGGCT CCTCGGACCT TTACCTGGTC ACGAGGCACG  3750
CCGATGTCAT TCCCGTGCGC CGGCGAGGTG ATAGCAGGGG TAGCCTGCTT  3800
```

|  10 | 20 | 30 | 40 | 50 | |
| 1234567890 | 1234567890 | 1234567890 | 1234567890 | 1234567890 | |
| TCGCCCCGGC | CCATTTCCTA | CTTGAAAGGC | TCCTCGGGGG | GTCCGCTGTT | 3850 |
| GTGCCCCGCG | GGACACGCCG | TGGGCTATT | CAGGGCCGCG | GTGTGCACCC | 3900 |
| GTGGAGTGGC | TAAAGCGGTG | GACTTTATCC | CTGTGGAGAA | CCTAGGGACA | 3950 |
| ACCATGAGAT | CCCCGGTGTT | CACGGACAAC | TCCTCTCCAC | CAGCAGTGCC | 4000 |
| CCAGAGCTTC | CAGGTGGCCC | ACCTGCATGC | TCCCACCGGC | AGCGGTAAGA | 4050 |
| GCACCAAGGT | CCCGGCTGCG | TACGCAGCCC | AGGGCTACAA | GGTGTTGGTG | 4100 |
| CTCAACCCCT | CTGTTGCTGC | AACGCTGGGC | TTTGGTGCTT | ACATGTCCAA | 4150 |
| GGCCCATGGG | GTTGATCCTA | ATATCAGGAC | CGGGGTGAGA | ACAATTACCA | 4200 |
| CTGGCAGCCC | CATCACGTAC | TCCACCTACG | GCAAGTTCCT | TGCCGACGGC | 4250 |
| GGGTGCTCAG | GAGGTGCTTA | TGACATAATA | ATTTGTGACG | AGTGCCACTC | 4300 |
| CACGGATGCC | ACATCCATCT | TGGGCATCGG | CACTGTCCTT | GACCAAGCAG | 4350 |
| AGACTGCGGG | GGCGAGACTG | GTTGTGCTCG | CCACTGCTAC | CCCTCCGGGC | 4400 |
| TCCGTCACTG | TGTCCCATCC | TAACATCGAG | GAGGTTGCTC | TGTCCACCAC | 4450 |
| CGGAGAGATC | CCCTTTTACG | GCAAGGCTAT | CCCCCTCGAG | GTGATCAAGG | 4500 |
| GGGAAGACA | TCTCATCTTC | TGCCACTCAA | AGAAGAAGTG | CGACGAGCTC | 4550 |
| GCCGCGAAGC | TGGTCGCATT | GGGCATCAAT | GCCGTGGCCT | ACTACCGCGG | 4600 |
| TCTTGACGTG | TCTGTCATCC | CGACCAGCGG | CGATGTTGTC | GTCGTGTCGA | 4650 |
| CCGATGCTCT | CATGACTGGC | TTTACCGGCG | ACTTCGACTC | TGTGATAGAC | 4700 |
| TGCAACACGT | GTGTCACTCA | GACAGTCGAT | TTCAGCCTTG | ACCCTACCTT | 4750 |
| TACCATTGAG | ACAACCACGC | TCCCCCAGGA | TGCTGTCTCC | AGGACTCAAC | 4800 |
| GCCGGGGCAG | GACTGGCAGG | GGGAAGCCAG | GCATCTATAG | ATTTGTGGCA | 4850 |
| CCGGGGGAGC | GCCCCTCCGG | CATGTTCGAC | TCGTCCGTCC | TCTGTGAGTG | 4900 |
| CTATGACGCG | GGCTGTGCTT | GGTATGAGCT | CACGCCCGCC | GAGACTACAG | 4950 |
| TTAGGCTACG | AGCGTACATG | AACACCCCGG | GCTTCCCGT | GTGCCAGGAC | 5000 |
| CATCTTGAAT | TTTGGGAGGG | CGTCTTTACG | GGCCTCACTC | ATATAGATGC | 5050 |
| CCACTTTTTA | TCCCAGACAA | AGCAGAGTGG | GGAGAACTTT | CCTTACCTGG | 5100 |
| TAGCGTACCA | AGCCACCGTG | TGCGCTAGGG | CTCAAGCCCC | TCCCCCATCG | 5150 |
| TGGGACCAGA | TGTGGAAGTG | TTTGATCCGC | CTTAAACCCA | CCCTCCATGG | 5200 |
| GCCAACACCC | CTGCTATACA | GACTGGGCGC | TGTTCAGAAT | GAAGTCACCC | 5250 |
| TGACGCACCC | AATCACCAAA | TACATCATGA | CATGCATGTC | GGCCGACCTG | 5300 |
| GAGGTCGTCA | CGAGCACCTG | GGTGCTCGTT | GGCGGCGTCC | TGGCTGCTCT | 5350 |
| GGCCGCGTAT | TGCCTGTCAA | CAGGCTGCGT | GGTCATAGTG | GGCAGGATCG | 5400 |
| TCTTGTCCGG | GAAGCCGGCA | ATTATACCTG | ACAGGGAGGT | TCTCTACCAG | 5450 |
| GAGTTCGATG | AGATGGAAGA | GTGCTCTCAG | CACTTACCCG | ACATGAGCCA | 5500 |
| AGGATGATG | CTCGCTGAGC | AGTTCAAGCA | GAAGGCCCTC | GGCCTCCTGC | 5550 |
| AGACCGCGTC | CCGCCATGCA | GAGGTTATCA | CCCCTGCTGT | CCAGACCAAC | 5600 |
| TGGCAGAAAC | TCGAGGTCTT | TTGGGCGAAG | CACATGTGGA | ATTTCATCAG | 5650 |
| TGGGATACAA | TACTTGGCGG | GCCTGTCAAC | CCTGCCTGGT | AACCCCGCCA | 5700 |

```
          10         20         30         40         50
 1234567890 1234567890 1234567890 1234567890 1234567890
 TTGCTTCATT GATGGCTTTT ACAGCTGCCG TCACCAGCCC ACTAACCACT  5750
 GGCCAAACCC TCCTCTTCAA CATATTGGGG GGTGGGTGG  CTGCCCAGCT  5800
 CGCCGCCCCC GGTGCCGCTA CTGCCTTTGT GGGTGCTGGC CTAGCTGGCG  5850
 CCGCCATCGG CAGCGTTGGA CTGGGGAAGG TCCTCGTGGA CATTCTTGCA  5900
 GGGTATGGCG CGGCGTGGC  GGAGCTCTT  GTAGCATTCA AGATCATGAG  5950
 CGGTCAGGTC CCCTCCACGG AGGACCTGGT CAATCTGCTG CCCGCCATCC  6000
 TCTCGCCTGG AGCCCTTGTA GTCGGTGTGG TCTGCGCAGC AATACTGCGC  6050
 CGGCACGTTG GCCCGGCGA  GGGGCAGTG  CAATGGATGA ACCGGCTAAT  6100
 AGCCTTCGCC TCCCGGGGA  ACCATGTTTC CCCCACGCAC TACGTGCCGG  6150
 AGAGCGATGC AGCCGCCCGC GTCACTGCCA TACTCAGCAG CCTCACTGTA  6200
 ACCCAGCTCC TGAGGCGACT GCATCAGTGG ATAAGCTCGG AGTGTACCAC  6250
 TCCATGCTCC GGTTCCTGGC TAAGGGACAT CTGGACTGG  ATATGCGAGG  6300
 TGCTGAGCGA CTTTAAGACC TGGCTGAAAG CCAAGCTCAT GCCACAACTG  6350
 CCTGGGATTC CCTTTGTGTC CTGCCAGCGC GGGTATAGG  GGGTCTGGCG  6400
 AGGAGACGGC ATTATGCACA CTCGCTGCCA CTGTGGAGCT GAGATCACTG  6900
 GACATGTCAA AAACGGGACG ATGAGGATCG TCGGTCCTAG GACCTGCAGG  6950
 AACATGTGGA GTGGACGTT  CCCCATTAAC GCCTACACCA CGGGCCCCTG  6550
 TACTCCCCTT CCTGCGCCGA ACTATAAGTT CCCGCTGTGG AGGGTGTCTG  6600
 CAGAGGAATA CGTGGAGATA AGGCGGGTGG GGACTTCCA  CTACGTATCG  6650
 GGTATGACTA CTGACAATCT TAAATGCCCG TGCCAGATCC CATCGCCCGA  6700
 ATTTTTCACA GAATTGGACG GGGTGCGCCT ACACAGGTTT GCGCCCCCTT  6750
 GCAAGCCCTT GCTGCGGGAG GAGGTATCAT TCAGAGTACG ACTCCACGAG  6800
 TACCCGGTCG GGTCGCAATT ACCTTGCGAG CCCGAACCGG ACGTAGCCGT  6850
 GTTGACGTCC ATGCTCACTG ATCCCTCCCA TATAACAGCA GAGGCGGCCG  6900
 GGAGAAGGTT GGCGAGAGGG TCACCCCCTT CTATGGCCAG CTCCTCGGCT  6950
 AGCCAGCTGT CCGCTCCATC TCTCAAGGCA ACTTGCACCG CCAACCATGA  7000
 CTCCCCTGAC GCCGAGCTCA TAGAGGCTAA CCTCCTGTGG AGGCAGGAGA  7050
 TGGGCGGCAA CATCACCAGG GTTGAGTCAG AGAACAAAGT GGTGATTCTG  7100
 GACTCCTTCG ATCCGCTTGT GGCAGAGGAG GATGAGCGG  AGGTCTCCGT  7150
 ACCTGCAGAA ATTCTGCGGA AGTCTCGGAG ATTCGCCGG  GCCCTGCCCG  7200
 TCTGGCCGCG GCCGGACTAC AACCCCCGC  TAGTAGAGAC GTGGAAAAAG  7250
 CCTGACTACG AACCACCTGT GGTCCATGGC TGCCCGCTAC CACCTCCACG  7300
 GTCCCCTCCT GTGCCTCCGC CTCGGAAAAA GGTACGGTG  GTCCTCACCG  7350
 AATCAACCCT ATCTACTGCC TTGCCCGAGC TTGCCACCAA AAGTTTTGGC  7400
 AGCTCCTCAA CTTCCGGCAT TACGGGCGAC AATACGACAA CATCCTCTGA  7450
 GCCCGCCCCT TCTGGCTGCC CCCCGACTC  CGACGTTGAG TCCTATTCTT  7500
 CCATGCCCCC CCTGGAGGG  GAGCCTGGG  ATCCGGATCT CAGCGACGGG  7550
 TCATGGTCGA CGGTCAGTAG TGGGCCCGAC ACGGAAGATG TCGTGTGCTG  7600
```

```
         10         20         30         40         50
1234567890 1234567890 1234567890 1234567890 1234567890
CTCAATGTCT TATTCCTGGA CAGGCGCACT CGTCACCCCG TGCGCTGCGG   7650
AAGAACAAAA ACTGCCCATC AACGCACTGA GCAACTCGTT GCTACGCCAT   7700
CACAATCTGG TGTATTCCAC CACTTCACGC AGTGCTTGCC AAAGGCAGAA   7750
GAAAGTCACA TTTGACAGAC TGCAAGTTCT GGACAGCCAT TACCAGGACG   7800
TGCTCAAGGA GGTCAAAGCA GCGGCGTCAA AAGTGAAGGC TAACTTGCTA   7850
TCCGTAGAGG AAGCTTGCAG CCTGACGCCC CCACATTCAG CCAAATCCAA   7900
GTTTGGCTAT GGGGCAAAAG ACGTCCGTTG CCATCCAGA AAGGCCGTAG    7950
CCCACATCAA CTCCGTGTGG AAAGACCTTC TGGAAGACAG TGTAACACCA   8000
ATAGACACTA CCATCATGGC CAAGAACGAG GTTTTCTGCG TTCAGCCTGA   8050
GAAGGGGGGT CGTAAGCCAG CTCGTCTCAT CGTGTTCCCC GACCTGGGCG   8100
TGCGCGTGTG CGAGAAGATG GCCCTGTACG ACGTGGTTAG CAAGCTCCCC   8150
CTGGCCGTGA TGGGAAGCTC CTACGGATTC CAATACTCAC CAGGACAGCG   8200
GGTTGAATTC CTCGTGCAAG CGTGGAAGTC CAAGAAGACC CCGATGGGGT   8250
TCTCGTATGA TACCCGCTGT TTTGACTCCA CAGTCACTGA GAGCGACATC   8300
CGTACGGAGG AGGCAATTTA CCAATGTGT GACCTGGACC CCCAAGCCCG    8350
CGTGGCCATC AAGTCCCTCA CTGAGAGGCT TTATGTTGGG GGCCCTCTTA   8400
CCAATTCAAG GGGGAAAAC TGCGGCTACC GCAGGTGCCG CGCGAGCGGC    8450
GTACTGACAA CTAGCTGTGG TAACACCCTC ACTTGCTACA TCAAGGCCCG   8500
GGCAGCCTGT CGAGCCGCAG GGCTCCAGGA CTGCACCATG CTCGTGTGTG   8550
GCGACGACTT AGTCGTTATC TGTGAAAGTG CGGGGGTCCA GGAGGACGCG   8600
GCGAGCCTGA GAGCCTTCAC GGAGGCTATG ACCAGGTACT CCGCCCCCCC   8650
CGGGGACCCC CCACAACCAG AATACGACTT GGAGCTTATA ACATCATGCT   8700
CCTCCAACGT GTCAGTCGCC CACGACGGCG CTGGAAAGAG GGTCTACTAC   8750
CTTACCCGTG ACCCTACAAC CCCCCTCGCG AGAGCCGCGT GGGAGACAGC   8800
AAGACACACT CCAGTCAATT CCTGGCTAGG CAACATAATC ATGTTTGCCC   8850
CCACACTGTG GGCGAGGATG ATACTGATGA CCCATTTCTT TAGCGTCCTC   8900
ATAGCCAGGG ATCAGCTTGA ACAGGCTCTT AACTGTGAGA TCTACGGAGC   8950
CTGCTACTCC ATAGAACCAC TGGATCTACC TCAATCATT CAAAGACTCC    9000
ATGGCCTCAG CGCATTTTCA CTCCACAGTT ACTCTCCAGG TGAAATCAAT   9050
AGGGTGGCCG CATGCCTCAG AAAACTTGGG GTCCCGCCCT TGCGAGCTTG   9100
GAGACACCGG GCCCGGAGCG TCCGCGCTAG GCTTCTGTCC AGAGGAGGCA   9150
GGGCTGCCAT ATGTGGCAAG TACCTCTTCA ACTGGGCAGT AAGAACAAAG   9200
CTCAAACTCA CTCCAATAGC GGCCGCTGGC CGGCTGGACT TGTCCGGTTG   9250
GTTCACGGCT GGCTACAGCG GGGAGACAT TTATCACAGC GTGTCTCATG    9300
CCCGGCCCCG CTGGTTCTGG TTTTGCCTAC TCCTGCTCGC TGCAGGGTA    9350
GGCATCTACC TCCTCCCCAA CCGATGAAGG TTGGGGTAAA CACTCCGCC    9400
TCTTAAGCCA TTTCCTGTTT TTTTTTTTTT TTTTTTTTTT TTTTCTTTT    9450
TTTTTTTCTT TCCTTTCCTT CTTTTTTTCC TTTCTTTTTC CCTTCTTTAA   9500
```

| 10 | 20 | 30 | 40 | 50 | |
|---|---|---|---|---|---|
| 1234567890 | 1234567890 | 1234567890 | 1234567890 | 1234567890 | |
| TGGTGGCTCC | ATCTTAGCCC | TAGTCACGGC | TAGCTGTGAA | AGGTCCGTGA | 9550 |
| GCCGCATGAC | TGCAGAGAGT | GCTGATACTG | GCCTCTCTGC | AGATCATGT | 9599 |

```
              10         20         30         40         50
         1234567890 1234567890 1234567890 1234567890 1234567890
         MSTNPKPQRK TKRNTNRRPQ DVKFPGGGQI VGGVYLLPRR GPRLGVRATR    50
         KTSERSQPRG RRQPIPKARR PEGRTWAQPG YPWPLYGNEG CGWAGWLLSP   100
         RGSRPSWGPT DPRRRSRNLG KVIDTLTCGF ADLMGYIPLV GAPLGGAARA   150
         LAHGVRVLED GVNYATGNLP GCSFSIFLLA LLSCLTVPAS AYQVRNSSGL   200
         YHVTNDCPNS SIVYEAADAI LHTPGCVPCV REGNASRCW  AVTPTVATRD   250
         GKLPTTQLRR HIDLLVGSAT LCSALYVGDL CGSVFLVGQL FTFSPRRHWT   300
         TQDCNCSIYP GHTTGHRMAW DMMMNWSPTA ALVVAQLLRI PQAIMDMIAG   350
         AHWGVLAGIA YFSMVGNWAK VLVVLLLFAG VDAETHVTGG NAGRTTAGLV   400
         GLLTPGAKQN IQLINTNGSW HINSTALNCN ESLNTGWLAG LFYQHKFNSS   450
         GCPERLASCR RLTDFAQGWG PISYANGSGL DERPYCWHYP PRPCGIVPAK   500
         SVCGPVYCFT PSPVVVGTTD RSGAPTYSWG ANDIDVFVLN NTRPPLGNWF   550
         GCTWMNSTGF TKVCGAPPCV IGGVGNNTLL CPTDCFRKHP EATYSRCGSG   600
         PWITPRCMVD YPYRLWHYPC TINYTIFKVR MYVGGVEHRL EAACNWTRGE   650
         RCDLEDRDRS ELSPLLLSTT QWQVLPCSFT TLPALSTGLI HLHQNIVDVQ   700
         YLYGVGSSIA SWAIKWEYVV LLFLLLADAR VCSCLWMML  ISQAEAALEN   750
         LVILNAASLA GTHGLVSFLV FFCFAWYLKG RWVPGAVYAL YGMWPLLLLL   800
         LALPQRAYAL DTEVAASCGG VVLVGLMALT LSPYYKRYIS WCMWWLQYFL   850
         TRVEAQLHVW VPPLNVRGGR DAVILLMCVV HPTLVFDITK LLLAIFGPLW   900
         ILQASLLKVP YFVRVQGLLR ICALARKIAG GHYVQMAIIK LGALTGTYVY   950
         NHLTPLRDWA HNGLRDLAVA VEPVVFSRME TKLITWGADT AACGDIINGL  1000
         PVSARRGQEI LLGPADGMVS KGWRLLAPIT AYAQQTRGLL GCIITSLTGR  1050
         DKNQVEGEVQ IVSTATQTFL ATCINGVCWT VYHGAGTRTI ASPKGPVIQM  1100
         YTNVDQDLVG WPAPQGSRSL TPCTCGSSDL YLVTRHADVI PVRRRGDSRG  1150
         SLLSPRPISY LKGSSGGPLL CPAGHAVGLF RAAVCTRGVA KAVDFIPVEN  1200
         LGTTMRSPVF TDNSSPPAVP QSFQVAHLHA PTGSGKSTKV PAAYAAQGYK  1250
         VLVLNPSVAA TLGFGAYMSK AHGVDPNIRT GVRTITTGSP ITYSTYGKFL  1300
         ADGGCSGGAY DIIICDECHS TDATSILGIG TVLDQAETAG ARLVVLATAT  1350
         PPGSVTVSHP NIEEVALSTT GEIPFYGKAI PLEVIKGGRH LIFCHSKKKC  1400
         DELAAKLVAL GINAVAYYRG LDVSVIPTSG DVVVVSTDAL MTGFTGDFDS  1450
         VIDCNTCVTQ TVDFSLDPTF TIETTTLPQD AVSRTQRRGR TGRGKPGIYR  1500
         FVAPGERPSG MFDSSVLCEC YDAGCAWYEL TPAETTVRLR AYMNTPGLPV  1550
         CQDHLEFWEG VFTGLTHIDA HFLSQTKQSG ENFPYLVAYQ ATVCARAQAP  1600
         PPSWDQMWKC LIRLKPTLHG PTPLLYRLGA VQNEVTLTHP ITKYIMTCMS  1650
         ADLEVVTSTW VLVGGVLAAL AAYCLSTGCV VIVGRIVLSG KPAIIPDREV  1700
         LYQEFDEMEE CSQHLPYIEQ GMMLAEQFKQ KALGLLQTAS RHAEVITPAV  1750
         QTNWQKLEVF WAKHMWNFIS GIQYLAGLST LPGNPAIASL MAFTAAVTSP  1800
         LTTGQTLLFN ILGGWVAAQL AAPGAATAFV GAGLAGAAIG SVGLGKVLVD  1850
         ILAGYGAGVA GALVAFKIMS GEVPSTEDLV NLLPAILSPG ALVVGVVCAA  1900
```

```
           10         20         30         40         50
  1234567890 1234567890 1234567890 1234567890 1234567890
  ILRRHVGPGE GAVQWMNRLI AFASRGNHVS PTHYVPESDA AARVTAILSS   1950
  LTVTQLLRRL HQWISSECTT PCSGSWLRDI WDWICEVLSD FKTWLKAKLM   2000
  PQLPGIPFVS CQRGYRGVWR GDGIMHTRCH CGAEITGHVK NGTMRIVGPR   2050
  TCRNMWSGTF PINAYTTGPC TPLPAPNYKF ALWRVSAEEY VEIRRVGDFH   2100
  YVSGMTTDNL KCPCQIPSPE FFTELDGVRL HRFAPPCKPL LREEVSFRVG   2150
  LHEYPVGSQL PCEPEPDVAV LTSMLTDPSH ITAEAAGRRL ARGSPPSMAS   2200
  SSASQLSAPS LKATCTANHD SPDAELIEAN LLWRQEMGGN ITRVESENKV   2250
  VILDSFDPLV AEEDEREVSV PAEILRKSRR FARALPVWAR PDYNPPLVET   2300
  WKKPDYEPPV VHGCPLPPPR SPPVPPPRKK RTVVLTESTL STALAELATK   2350
  SFGSSSTSGI TGDNTTTSSE PAPSGCPPDS DVESYSSMPP LEGEPGDPDL   2400
  SDGSWSTVSS GADTEDVVCC SMSYSWTGAL VTPCAAEEQK LPINALSNSL   2450
  LRHHNLVYST TSRSACQRQK KVTFDRLQVL DSHYQDVLKE VKAAASKVKA   2500
  NLLSVEEACS LTPPHSAKSK FGYGAKDVRC HARKAVAHIN SVWKDLLEDS   2550
  VTPIDTTIMA KNEVFCVQPE KGGRKPARLI VFPDLGVRVC EKMALYDVVS   2600
  KLPLAVMGSS YGFQYSPGQR VEFLVQAWKS KKTPMGFSYD TRCFDSTVTE   2650
  SDIRTEEAIY QCCDLDPQAR VAIKSLTERL YVGGPLTNSR GENCGYRRCR   2700
  ASGVLTTSCG NTLTCYIKAR AACRAAGLQD CTMLVCGDDL VVICESAGVQ   2750
  EDAASLRAFT EAMTRYSAPP GDPPQPEYDL ELITSCSSNV SVAHDGAGKR   2800
  VYYLTRDPTT PLARAAWETA RHTPVNSWLG NIIMFAPTLW ARMILMTHFF   2850
  SVLIARDQLE QALNCEIYGA CYSIEPLDLP PIIQRLHGLS AFSLHSYSPG   2900
  EINRVAACLR KLGVPPLRAW RHRARSVRAR LLSRGGRAAI CGKYLFNWAV   2950
  RTKLKLTPIA AAGRLDLSGW FTAGYSGGDI YHSVSHARPR WFWFCLLLLA   3000
  AGVGIYLLPN R                                             3011
```

|  | 10 | 20 | 30 | 40 | 50 |  |
|---|---|---|---|---|---|---|
|  | 1234567890 | 1234567890 | 1234567890 | 1234567890 | 1234567890 |  |
|  | GCCAGCCCCC | TGATGGGGGC | GACACTCCAC | CATGAATCAC | TCCCCTGTGA | 50 |
|  | GGAACTACTG | TCTTCACGCA | GAAAGCGTCT | AGCCATGCCG | TTAGTATGAG | 100 |
|  | TGTCGTGCAG | CCTCCAGGAC | CCCCCCTCCC | GGAGAGCCA | TAGTGGTCTG | 150 |
|  | CGGAACCGGT | GAGTACACCG | GAATTGCCAG | GACGACCGGG | TCCTTTCTTG | 200 |
|  | GATCAACCCG | CTCAATGCCT | GGAGATTTGG | GCGTGCCCCC | GCGAGACTGC | 250 |
|  | TAGCCGAGTA | GTGTTGGGTC | GCGAAAGGCC | TTGTGGTACT | GCCTGATAGG | 300 |
|  | GTGCTTGCGA | GTGCCCCGGG | AGGTCTCGTA | GACCGTGCAC | CATGAGCACG | 350 |
|  | AATCCTAAAC | CTCAAAGAAA | AACCAAACGT | AACACCAACC | GCCGCCACA | 400 |
|  | GGACGTCAAG | TTCCCGGGCG | GTGGTCAGAT | CGTTGGTGGA | GTTTACCTGT | 450 |
|  | TGCCGCGCAG | GGGCCCCAGG | TTGGGTGTGC | GCGCGACTAG | GAAGGCTTCC | 500 |
|  | GAGCGGTCGC | AACCTCGTGG | AAGGCGACAA | CCTATCCAA | AGGCTCGCCG | 550 |
|  | ACCCGAGGGC | AGGGCCTGGG | CTCAGCCCGG | GTACCCTTGG | CCCCTCTATG | 600 |
|  | GCAATGAGGG | CCTGGGGTGG | GCAGGATGGC | TCCTGTCACC | CCGCGGCTCC | 650 |
|  | CGGCCTAGTT | GGGGCCCCAC | GGACCCCCGG | CGTAGGTCGC | GTAACTTGGG | 700 |
|  | TAAGGTCATC | GATACCCTTA | CATGCGGCTT | CGCCGATCTC | ATGGGTACA | 750 |
|  | TTCCGCTCGT | CGGCGCCCCC | CTAGGGGCG | CTGCCAGGGC | CTTGGCACAC | 800 |
|  | GGTGTCCGGG | TTCTGGAGGA | CGGCGTGAAC | TATGCAACAG | GAACTTGCC | 850 |
|  | CGGTTGCTCT | TTCTCTATCT | TCCTCTTGGC | TCTGCTGTCC | TGTTTGACCA | 900 |
|  | TCCCAGCTTC | CGCTTATGAA | GTGCGCAACG | TGTCCGGGAT | ATACCATGTC | 950 |
|  | ACGAACGACT | GCTCCAACTC | AAGCATTGTG | TATGAGGCAG | CGGACGTGAT | 1000 |
|  | CATGCATACT | CCCGGGTGCG | TGCCCTGTGT | TCAGGAGGGT | AACAGCTCCC | 1050 |
|  | GTTGCTGGGT | AGCGCTCACT | CCCACGCTCG | CGGCCAGGAA | TGCCAGCGTC | 1100 |
|  | CCCACTACGA | CAATACGACG | CCACGTCGAC | TTGCTCGTTG | GGACGGCTGC | 1150 |
|  | TTTCTGCTCC | GCTATGTACG | TGGGGATCT | CTGCGGATCT | ATTTTCCTCG | 1200 |
|  | TCTCCCAGCT | GTTCACCTTC | TCGCCTCGCC | GGCATGAGAC | AGTGCAGGAC | 1250 |
|  | TGCAACTGCT | CAATCTATCC | CGGCCATGTA | TCAGGTCACC | GCATGGCTTG | 1300 |
|  | GGATATGATG | ATGAACTGGT | CACCTACAAC | AGCCCTAGTG | GTGTCGCAGT | 1350 |
|  | TGCTCCGGAT | CCCACAAGCT | GTCGTGGACA | TGGTGGCGGG | GCCCACTGG | 1400 |
|  | GGAGTCCTGG | CGGGCCTTGC | CTACTATTCC | ATGGTAGGGA | ACTGGGCTAA | 1450 |
|  | GGTTCTGATT | GTGGCGCTAC | TCTTTGCCGG | CGTTGACGGG | GAGACCACA | 1500 |
|  | CGACGGGAG | GGTGGCCGGC | CACACCACCT | CCGGGTTCAC | GTCCCTTTTC | 1550 |
|  | TCATCTGGGG | CGTCTCAGAA | AATCCAGCTT | GTGAATACCA | ACGGCAGCTG | 1600 |
|  | GCACATCAAC | AGGACTGCCC | TAAATTGCAA | TGACTCCCTC | CAAACTGGGT | 1650 |
|  | TCTTTGCCGC | GCTGTTTTAC | GCACACAAGT | TCAACTCGTC | CGGGTGCCCG | 1700 |
|  | GAGCGCATGG | CCAGCTGCCG | CCCCATTGAC | TGGTTCGCCC | AGGGGTGGGG | 1750 |
|  | CCCCATCACC | TATACTAAGC | CTAACAGCTC | GGATCAGAGG | CCTTATTGCT | 1800 |
|  | GGCATTACGC | GCCTCGACCG | TGTGGTGTCG | TACCGCGTC | GCAGGTGTGT | 1850 |
|  | GGTCCAGTGT | ATTGTTTCAC | CCCAAGCCCT | GTTGTGGTGG | GGACCACCGA | 1900 |

```
         10         20         30         40         50
1234567890 1234567890 1234567890 1234567890 1234567890
TCGTTCCGGT GTCCCTACGT ATAGCTGGGG GGAGAATGAG ACAGACGTCA  1950
TGCTCCTCAA CAACACGCGT CCGCCACAAG GCAACTGGTT CGGCTGTACA  2000
TGGATGAATA GTACTGGGTT CACTAAGACG TCGGAGGTC CCCCGTGTAA  2050
CATCGGGGG GTCGGTAACC GCACCTTGAT CTGCCCCACG GACTGCTTCC  2100
GGAAGCACCC CGAGGCTACT TACACAAAAT GTGGCTCGGG GCCCTGGTTG  2150
ACACCTAGGT GCCTAGTAGA CTACCCATAC AGGCTTTGGC ACTACCCCTG  2200
CACTCTCAAT TTTTCCATCT TTAAGGTTAG GATGTATGTG GGGGCCGTGG  2250
AGCACAGGCT CAATGCCGCA TGCAATTGGA CTCGAGGAGA GGGCTGTAAC  2300
TTGGAGGACA GGGATAGGTC AGAACTCAGC CCGCTGCTGC TGTCTACAAC  2350
AGAGTGGCAG ATACTGCCCT GTGCTTTCAC CACCCTACCG GCTTTATCCA  2400
CTGGTTTGAT CCATCTCCAT CAGAACATCG TGGACGTGCA ATACCTGTAC  2450
GGTGTAGGGT CAGCGTTTGT CTCCTTTGCA ATCAAATGGG AGTACATCCT  2500
GTTGCTTTTC CTTCTCCTGG CAGACGCGCG CGTGTGTGCC TGCTTGTGGA  2550
TGATGCTGCT GATAGCCCAG GCTGAGGCCG CCTTAGAGAA CTTGGTGGTC  2600
CTCAATGCGG CGTCCGTGGC CGGAGCGCAT GGTATTCTCT CCTTCTTGT  2650
GTTCTTCTGC GCCGCCTGGT ACATTAAGGG CAGGCTGGCT CCTGGGCGG  2700
CGTATGCTTT TTATGGCGTA TGCCCGCTGC TCCTGCTCCT ACTGGCGTTA  2750
CCACCACGAG CTTACGCCTT GGACCGGGAG ATGGCTGCAT CGTCCGGGG  2800
TGCGGTTCTT GTAGGTCTGG TATTCTTGAC CTTGTCACCA TACTACAAAG  2850
TGTTTCTCAC TAGGCTCATA TGGTGGTTAC AATACTTTAT CACCAGAGCC  2900
GAGGCGCACA TGCAAGTGTG GGTCCCCCCC CTCAACGTTC GGGAGGCCG  2950
CGATGCCATC ATCCTCCTCA CGTGTGCGGT TCATCCAGAG TTAATTTTTG  3000
ACATCACCAA ACTCCTGCTC GCCATACTCG GCCCGCTCAT GGTGCTCCAG  3050
GCTGGCATAA CGAGAGTGCC GTACTTGTG CGCGCTCAAG GGCTCATTCG  3100
TGCATGCATG TTAGTGCGAA AAGTCGCCGG GGGTCATTAT GTCCAAATGG  3150
TCTTCATGAA GCTGGGCGCG CTGACAGGTA CGTACGTTTA TAACCATCTT  3200
ACCCCACTGC GGGACTGGGC CCACGCGGGC CTACGAGACC TTGCCGGTGCC  3250
GGTAGAGCCC GTCGTCTTCT CCGCCATGGA GACCAAGGTC ATCACCTGG  3300
GAGCAGACAC CGCTGCGTGT GGGACATCA TCTTGGGCT ACCCGTCTCC  3350
GCCCGAAGGG GGAAGGAGAT ATTTTTGGGA CCGGCTGATA GTCTCGAAGG  3400
GCAAGGGTGG CGACTCCTTG CGCCCATCAC GGCCTACTCC CAACAAACGC  3450
GGGCGTACT TGGTTGCATC ATCACTAGCC TCACAGGCCG GACAAGAAC   3500
CAGGTCGAAG GGAGGTTCA AGTGGTTTCT ACCGCAACAC AATCTTTCCT  3550
GGCGACCTGC ATCAACGGCG TGTGCTGGAC TGTCTACCAT GGCGCTGGCT  3600
CGAAGACCCT AGCCGGTCCA AAAGGTCCAA TCACCCAAAT GTACACCAAT  3650
GTAGACCTGG ACCTCGTCGG CTGGCAGGCG CCCCCCGGG CGCGCTCCAT   3700
GACACCATGC AGCTGTGGCA GCTCGGACCT TTACTTGGTC ACGAGACATG  3750
CTGATGTCAT TCCGGTGCGC CGGCGAGGCG ACAGCAGGGG AAGTCTACTC  3800
```

```
         10         20         30         40         50
1234567890 1234567890 1234567890 1234567890 1234567890
TCCCCCAGGC CCGTCTCCTA CCTGAAAGGC TCCTCGGGTG GTCCATTGCT  3850
TTGCCCTTCG GGGCACGTCG TGGGCGTCTT CCGGGCTGCT GTGTGCACCC  3900
GGGGGGTCGC GAAGGCGGTG GACTTCATAC CCGTTGAGTC TATGGAAACT  3950
ACCATGCGGT CTCCGGTCTT CACAGACAAC TCAACCCCCC CGGCTGTACC  4000
GCAGACATTC CAAGTGGCAC ATCTGCACGC TCCTACTGGC AGCGGCAAGA  4050
GCACCAAAGT GCCGGCTGCG TATGCAGCCC AAGGGTACAA GGTGCTCGTC  4100
CTGAACCCGT CCGTTGCCGC CACCTTAGGG TTTGGGCGT ATATGTCCAA   4150
GGCACACGGT ATCGACCCTA ACATCAGAAC TGGGTAAGG ACCATTACCA   4200
CGGGCGGCTC CATTACGTAC TCCACCTATG GCAAGTTCCT TGCCGACGGT  4250
GGCTGTTCTG GGGCGCCTA TGACATCATA ATATGTGATG AGTGCCACTC   4300
AACTGACTCG ACTACCATCT TGGGCATCGG CACAGTCCTG GACCAAGCGG  4350
AGACGGCTGG AGCGCGGCTC GTCGTGCTCG CCACCGCTAC ACCTCCGGGA  4400
TCGGTTACCG TGCCACACCC CAATATCGAG GAAATAGGCC TGTCCAACAA  4450
TGAGAGATC CCCTTCTATG GCAAAGCCAT CCCCATTGAG GCCATCAAGG   4500
GGGGGAGGCA TCTCATTTTC TGCCATTCCA AGAAGAAATG TGACGAGCTC  4550
GCCGCAAAGC TGACAGGCCT CGGACTGAAC GCTGTAGCAT ATTACCGGGG  4600
CCTTGATGTG TCCGTCATAC CGCCTATCGG AGACGTCGTT GTCGTGGCAA  4650
CAGACGCTCT AATGACGGGT TTCACCGGCG ATTTGACTC AGTGATCGAC   4700
TGCAATACAT GTGTCACCCA GACAGTCGAC TTCAGCTTGG ATCCCACCTT  4750
CACCATTGAG ACGACGACCG TGCCCCAAGA CGCGGTGTCG CGCTCGCAAC  4800
GGCGAGGTAG AACTGGCAGG GGTAGGAGTG GCATCTACAG GTTTGTGACT  4850
CCAGGAGAAC GGCCCTCGGG CATGTTCGAT TCTTCGGTCC TGTGTGAGTG  4900
CTATGACGCG GGCTGTGCTT GGTATGAGCT CACGCCCGCT GAGACCTCGG  4950
TTAGGTTGCG GGCTTACCTA AATACACCAG GGTTGCCCGT CTGCCAGGAC  5000
CATCTGGAGT TCTGGGAGAG CGTCTTCACA GGCCTCACCC ACATAGATGC  5050
CCACTTCCTG TCCCAGACTA AACAGGCAGG AGACAACTTT CCTTACCTGG  5100
TGGCATATCA AGCTACAGTG TGCGCCAGGG CTCAAGCTCC ACCTCCATCG  5150
TGGACCAAA TGTGGAAGTG TCTCATACGG CTGAAACCTA CACTGCACGG   5200
GCCAACACCC CTGCTGTATA GGCTAGGAGC CGTCCAAAAT GAGGTCATCC  5250
TCACACACCC CATAACTAAA TACATCATGG CATGCATGTC GGCTGACCTG  5300
GAGGTCGTCA CTAGCACCTG GGTGCTGGTA GGCGGAGTCC TTGCAGCTTT  5350
GGCCCGCATAC TGCCTGACGA CAGGCAGTGT GGTCATTGTG GCCAGGATCA 5400
TCTTGTCCGG GAAGCCAGCT GTCGTTCCCG ACAGGAAGT CCTCTACCAG   5450
GAGTTCGATG AGATGGAAGA GTGTGCCTCA CAACTTCCTT ACATCGAGCA  5500
GGGAATGCAG CTCGCCGAGC AATTCAAGCA AAAGGCGCTC GGGTTGTTGC  5550
AAACGGCCAC CAAGCAAGCG GAGGCTGCTG CTCCCGTGGT GGAGTCCAAG  5600
TGGCGAGCCC TTGAGACCTT CTGGGCGAAG CACATGTGGA ATTTCATCAG  5650
CGGAATACAG TACCTAGCAG GCTTATCCAC TCTGCCTGGA AACCCCGCGA  5700
```

```
         10         20         30         40         50
1234567890 1234567890 1234567890 1234567890 1234567890
TAGCATCATT GATGGCATTT ACAGCTTCTA TCACTAGCCC GCTCACCACC  5750
CAAAACACCC TCCTGTTTAA CATCTTGGGG GGATGGGTGG CTGCCCAACT  5800
CGCTCCTCCC AGCGCTGCGT CAGCTTTCGT GGGCGCCGGC ATGCCCGGAG  5850
CGGCTGTTGG CAGCATAGGC CTTGGGAAGG TGCTCGTGGA CATCTTGGCG  5900
GGCTATGGGG CAGGGGTAGC CGGCGCACTC GTGGCCTTTA AGGTCATGAG  5950
CGGCGAGGTG CCCTCCACCG AGGACCTGGT CAACTTACTC CCTGCCATCC  6000
TCTCTCCTGG TGCCCTCGTC GTCGGGGTCG TGTGCGCAGC AATACTGCGT  6050
CGGCACGTGG GCCGGGAGA GGGGCTGTG CAGTGGATGA ACCGGCTGAT   6100
AGCGTTCGCT TCGCGGGGTA ACCACGTCTC CCCTACGCAC TATGTGCCTG  6150
AGAGCGACGC TGCAGCACGT GTCACTCAGA TCCTCTCTAG CCTTACCATC  6200
ACTCAACTGC TGAAGCGGCT CCACCAGTGG ATTAATGAGG ACTGCTCTAC  6250
GCCATGCTCC GGCTCGTGGC TAAGGGATGT TTGGGATTGG ATATGCACGG  6300
TGTTGACTGA CTTCAAGACC TGGCTCCAGT CCAAACTCCT GCCGCGGTTA  6350
CCGGGAGTCC CTTTCCTGTC ATGCCAACGC GGTACAAGG  GAGTCTGCCG   6400
GGGGACGGC ATCATGCAAA CCACCTGCCC ATGCGGAGCA CAGATCGCCG   6450
GACATGTCAA AAACGGTTCC ATGAGGATCG TAGGGCCTAG AACCTGCAGC  6500
AACACGTGGC ACGGAACGTT CCCCATCAAC GCATACACCA CGGACCTTG   6550
CACACCCTCC CCGGCGCCCA ACTATTCCAG GCCGCTATGG CGGGTGGCTG  6600
CTGAGGAGTA CGTGGAGGTT ACGCGTGTGG GGATTTCCA CTACGTGACG   6650
GGCATGACCA CTGACAACGT AAAGTGCCCA TGCCAGGTTC CGGCCCCGA   6700
ATTCTTCACG GAGGTGGATG GAGTGCGGTT GCACAGGTAC GCTCCGGCGT  6750
GCAAACCTCT TCTACGGGAG GACGTCACGT TCCAGGTCGG GCTCAACCAA  6800
TACTTGGTCG GGTCGCAGCT CCCATGCGAG CCCGAACCGG ACGTAACAGT  6850
GCTTACTTCC ATGCTCACCG ATCCCTCCCA CATTACAGCA GAGACGGCTA  6900
AGCGTAGGCT GGCTAGAGGG TCTCCCCCCT CTTTAGCCAG CTCATCAGCT  6950
AGCCAGTTGT CTGCGCCTTC TTTGAAGGCG ACATGCACTA CCCACCATGA  7000
CTCCCCGGAC GCTGACCTCA TGAGGCCAA  CCTCTTGTGG CGGCAGGAGA  7050
TGGGCGGAAA CATCACTCGC GTGGAGTCAG AGAATAAGGT AGTAATTCTG  7100
GACTCTTTCG AACCGCTTCA CGCGGAGGGG GATGAGAGGG AGATATCCGT  7150
CGCGGCGGAG ATCCTGCGAA AATCCAGGAA GTTCCCCTCA GCGTTGCCCA  7200
TATGGGCACG CCCGGACTAC AATCCTCCAC TGCTAGAGTC CTGGAAGGAC  7250
CCGGACTACG TCCCTCCGGT GGTACACGGA TGCCCATTGC CACCTACCAA  7300
GGCTCCTCCA ATACCACCTC CACGGAGAAA GAGGACGGTT GTCCTGACAG  7350
AATCCAATGT GTCTTCTGCC TTGCGGAGC  TGCCACTAA  GACCTTCGGT   7400
AGCTCCGGAT CGTCGGCCGT TGATAGCGGC ACGGCGACCG CCCTTCCTGA  7450
CCTGGCCTCC GACGACGGTG ACAAAGGATC CGACGTTGAG TCGTACTCCT  7500
CCATGCCCCC CCTTGAAGGG GAGCCGGGG  ACCCCGATCT CAGCGACGGG  7550
TCTTGGTCTA CCGTGAGTGA GGAGGCTAGT GAGGATGTCG TCTGCTGCTC  7600
```

```
         10         20         30         40         50
1234567890 1234567890 1234567890 1234567890 1234567890
AATGTCCTAT ACGTGGACAG GCGCCCTGAT CACGCCATGC GCTGCGGAGG   7650
AAAGTAAGCT GCCCATCAAC CCGTTGAGCA ACTCTTTGCT GGGTCACCAC   7700
AACATGGTCT ACGCCACAAC ATCCCGCAGC GCAAGCCTCC GGCAGAAGAA   7750
GGTCACCTTT GACAGATTGC AAGTCCTGGA TGATCATTAC CGGAACGTAC   7800
TCAAGGAGAT GAAGGCGAAG GCGTCCACAG TTAAGGCTAA GCTTCTATCT   7850
ATAGAGGAGG CCTGCAAGCT GACGCCCCCA CATTCGCCA  AATCCAAATT   7900
TGGCTATGGG GCAAAGGACG TCCGAACCT  ATCCAGCAGG GCCGTTAACC   7950
ACATCCGCTC CGTGTGGGAG GACTTGCTGG AAGACACTGA AACACCAATT   8000
GACACCACCA TCATGGCAAA AAGTGAGGTT TTCTGCGTCC AACCAGAGAA   8050
GGGAGGCCGC AAGCCAGCTC GCCTTATCGT ATTCCCAGAC CTGGGAGTTC   8100
GTGTATGCGA GAAGATGGCC CTTTACGACG TGGTCTCCAC CCTTCCTCAG   8150
GCCGTGATGG GCTCCTCATA CGGATTTCAA TACTCCCCA  AGCAGCGGGT   8200
CGAGTTCCTG GTGAATACCT GGAAATCAAA GAAATGCCCT ATGGGCTTCT   8250
CATATGACAC CCGCTGTTTT GACTCAACGG TCACTGAGAG TGACATTCGT   8300
GTTGAGGAGT CAATTTACCA ATGTTGTGAC TTGGCCCCCG AGGCCAGACA   8350
GGCCATAAGG TGCTCACAG  AGCGGCTTTA CATCGGGGGT CCCCTGACTA   8400
ACTCAAAAGG GCAGAACTGC GGTTATCGCC GGTGCCGCGC AAGTGGCGTG   8450
CTGACGACTA GCTGCGGTAA TACCCTCACA TGTTACTTGA AGGCCACTGC   8500
AGCCTGTCGA GCTGCAAAGC TCCAGGACTG CACGATGCTC GTGAACGGAG   8550
ACGACCTTGT CGTTATCTGT GAAAGCGCGG GAACCCAGGA GGATGCGGCG   8600
GCCCTACGAG CCTTCACGGA GGCTATGACT AGGTATTCCG CCCCCCCCGG   8650
GGATCCGCCC CAACCAGAAT ACGACCTGGA GCTGATAACA TCATGTTCCT   8700
CCAATGTGTC AGTCGCGCAC GATGCATCTG GCAAAAGGGT ATACTACCTC   8750
ACCCGTGACC CCACCACCCC CCTTGCACGG GCTGCGTGGG AGACAGCTAG   8800
ACACACTCCA ATCAACTCTT GGCTAGGCAA TATCATCATG TATGCGCCCA   8850
CCCTATGGGC AAGGATGATT CTGATGACTC ACTTTTTCTC CATCCTTCTA   8900
GCTCAAGAGC AACTTGAAAA AGCCCTGGAT TGTCAGATCT ACGGGCTTG   8950
CTACTCCATT GAGCCACTTG ACCTACCTCA GATCATTGAA CGACTCCATG   9000
GTCTTAGCGC ATTTACACTC CACAGTTACT CTCCAGGTGA GATCAATAGG   9050
GTGGCTTCAT GCCTCAGGAA ACTTGGGGTA CCACCCTTGC GAACCTGGAG   9100
ACATCGGGCC AGAAGTGTCC GCGCTAAGCT ACTGTCCCAG GGGGGAGGG   9150
CCGCCACTTG TGGCAGATAC CTCTTTAACT GGGCAGTAAG GACCAAGCTT   9200
AAACTCACTC CAATCCCGGC CGCGTCCAG  CTGGACTTGT CTGGCTGGTT   9250
CGTCGCTGGT TACAGCGGGG GAGACATATA TCACAGCCTG TCTCGTGCCC   9300
GACCCCGCTG GTTTCCGTTG TGCCTACTCC TACTTTCTGT AGGGGTAGGC   9350
ATTTACCTGC TCCCCAACCG ATGAACGGGG AGCTAACCAC TCCAGGCCTT   9400
AAGCCATTTC CTGTTTTTTT TTTTTTTTTT TTTTTTTTTT TCTTTTTTTT   9450
TTTCTTTCCT TTCCTTCTTT TTTCCTTTC  TTTTTCCCTT CTTTAATGGT   9500
```

FIG. 4E

```
          10         20         30         40         50
 1234567890 1234567890 1234567890 1234567890 1234567890
 GGCTCCATCT TAGCCCTAGT CACGGCTAGC TGTGAAAGGT CCGTGAGCCG    9550
 CATGACTGCA GAGAGTGCTG ATACTGGCCT CTCTGCAGAT CATGT         9595
```

FIG. 4F

|  | 10 | 20 | 30 | 40 | 50 |  |
|---|---|---|---|---|---|---|
|  | 1234567890 | 1234567890 | 1234567890 | 1234567890 | 1234567890 |  |
| MSINPKPQRK | TKRNINRRPQ | DVKFPGGQI | VGGVYLLPRR | GPRLGVRATR |  | 50 |
| KASERSQPRG | RRQPIPKARR | PEGRAWAQPG | YPWPLYGNEG | LGWAGWLLSP |  | 100 |
| RGSRPSWGPT | DPRRRSRNLG | KVIDTLJTOGF | ADLMGYIPLV | GAPLGGAARA |  | 150 |
| LAHGVRVLED | GVNYATGNLP | GCSFSIFLLA | LLSCLTIPAS | AYEVRNWSGI |  | 200 |
| YHVINDCSNS | SIVYEAADVI | MHITPGCVPCV | QEGNSSRCWV | ALTPILAARN |  | 250 |
| ASVPTTTIRR | HVDLLVGIAA | FCSAMYVGDL | CGSIFLVSQL | FIFSPRRHET |  | 300 |
| VQDCNCSTYP | GHVSGHRMAW | DMMMNWSPTT | ALVVSQLLRI | PQAVVDMVAG |  | 350 |
| AHWGVLAGLA | YYSMVGNWAK | VLIVALLFAG | VDGEIHITGR | VAGHTTSGFT |  | 400 |
| SLFSSGASQK | IQLVNINGSW | HINRTALNCN | DSLQTGFFAA | LFYAHKFNSS |  | 450 |
| GCPERMASCR | PIDWFAQGWG | PITYIKPNSS | DQRPYCWHYA | PRPCGVVPAS |  | 500 |
| QVCGPVYCFT | PSPVVVGTTD | RSGVPTYSWG | ENETDVMLLN | NIRPPQGNWF |  | 550 |
| GCTWMNSTGF | TKTCGGPPCN | IGGVGNRTLI | CPTDCFRKHP | EATYTKCGSG |  | 600 |
| PWLTPRCLVD | YPYRLWHYPC | TLNFSIFKVR | MYVGGVEHRL | NAACNWIRGE |  | 650 |
| RCNLEDRDRS | ELSPLLLSTT | EWQILPCAFT | TLPALSTGLI | HLHQNIVDVQ |  | 700 |
| YLYGVGSAFV | SFAIKWEYIL | LLFLLLADAR | VCACLWMMLL | IAQAEAALEN |  | 750 |
| LWVLNAASVA | GAHGILSFLV | FFCAAWYIKG | RLAPGAAYAF | YGVWPLLLLL |  | 800 |
| LALPPRAYAL | DREMAASCGG | AVLVGLVFLT | LSPYYKVFLT | RLIWWLQYFI |  | 850 |
| TRAEAHMQWV | VPPLNVRGGR | DAIILLTCAV | HPELIFDITK | LLLAILGPLM |  | 900 |
| VLQAGITRVP | YFVRAQGLIR | ACMLVRKVAG | GHYVQMVFMK | LGALTGTYVY |  | 950 |
| NHLTPLRDWA | HAGLRDLAVA | VEPVVFSAME | TKVTIWGADT | AACGDIILGL |  | 1000 |
| PVSARRGKEI | FLGPADSLEG | QGWRLLAPIT | AYSQQTRGVL | GCITTSLTGR |  | 1050 |
| DKNQVEGEVQ | VVSTATQSFL | ATCINGVCWT | VYHGAGSKTL | AGPKGPITQM |  | 1100 |
| YTNVDLDLVG | WQAPPGARSM | TPCSCGSSDL | YLVTRHADVI | PVRRRGDSRG |  | 1150 |
| SLLSPRPVSY | LKGSSGGPLL | CPSGHVVGVF | RAAVCTRGVA | KAVDFIPVES |  | 1200 |
| METTMRSPVF | TDNSTPPAVP | QTFQVAHLHA | PTGSGKSTKV | PAAYAAQGYK |  | 1250 |
| VLVLNPSVAA | TLGFGAYMSK | AHGIDPNIRT | GVRTTTTGGS | ITYSTYGKFL |  | 1300 |
| ADGGCSGGAY | DIIICDECHS | TDSTTILGIG | TVLDQAETAG | ARLVVLATAT |  | 1350 |
| PPGSVIVPHP | NIEEIGLSNN | GEIPFYGKAI | PIEAIKGGRH | LIFCHSKKKC |  | 1400 |
| DELAAKLTGL | GLNAVAYYRG | LDVSVIPPIG | DVVVVATDAL | MTGFTGDFDS |  | 1450 |
| VIDCNTCVTQ | TVDFSLDPTF | TIETTTVPQD | AVSRSQRRGR | TGRGRSGIYR |  | 1500 |
| FVTPGERPSG | MFDSSVLCEC | YDAGCAWYEL | TPAETSVRLR | AYLNTPGLPV |  | 1550 |
| CQDHLEFWES | VFTGLTHIDA | HFLSQTKQAG | DNFPYLVAYQ | ATVCARAQAP |  | 1600 |
| PPSWDQMWKC | LIRLKPTLHG | PTPLLYRLGA | VQNEVILTHP | ITKYIMACMS |  | 1650 |
| ADLEVVTSTW | VLVGGVLAAL | AAYCLTTGSV | VIVGRIILSG | KPAVVPDREV |  | 1700 |
| LYQEFDEMEE | CASQLPYIEQ | GMQLAEQFKQ | KALGLLQTAT | KQAEAAAPVV |  | 1750 |
| ESKWRALETF | WAKHMWNFIS | GIQYLAGLST | LPGNPAIASL | MAFTASITSP |  | 1800 |
| LTTQNTLLFN | ILGGWVAAQL | APPSAASAFV | GAGIAGAAVG | SIGLGKVLVD |  | 1850 |
| ILAGYGAGVA | GALVAFKVMS | GEVPSTEDLV | NLLPAILSPG | ALVVGVVCAA |  | 1900 |

FIG. 4G

```
          10         20         30         40         50
 1234567890 1234567890 1234567890 1234567890 1234567890
ILRRHVGPGE GAVQWMNRLI AFASRGNHVS PIHYVPESDA AARVIQILSS  1950
LTTTQLLKRL HQWINEDCST PCSGSWLRDV WDWICIVLID FKIWLQSKLL  2000
PRLPGVPFLS CQRGYKGVWR GDGIMQTTCP CGAQIAGHVK NGSMRIVGPR  2050
TCSNIWHGTF PINAYTTGPC TPSPAPNYSR ALWRVAAEEY VEVIRVGDFH  2100
YVTGMTTDNV KCPCQVPAPE FFTEVDGVRL HRYAPACKPL LREDVIFQVG  2150
LNQYLVGSQL PCEPEPDVIV LTSMLTDPSH ITAETAKRRL ARGSPPSLAS  2200
SSASQLSAPS LKATCTIHHD SPDADLIEAN LLWRQEMGGN ITRVESENKV  2250
VILDSFEPLH AEGDEREISV AAEILRKSRK FPSALPIWAR PDYNPPLLES  2300
WKDPDYVPPV VHGCPLPPTK APPIPPPRRK RIVVLTESNV SSALAELATK  2350
TFGSSGSSAV DSGIATALPD LASDDGDKGS DVESYSSMPP LEGEPGDPDL  2400
SDGSWSTVSE EASEDVVCCS MSYTWIGALI TPCAAEESKL PINPLSNSLL  2450
RHHNMVYATT SRSASLRQKK VIFDRLQVLD DHYRDVLKEM KAKASTVKAK  2500
LLSIEEACKL TPPHSAKSKF GYGAKDVRNL SSRAVNHIRS WEDLLEDTE   2550
TPIDTTIMAK SEVFCVQPEK GGRKPARLIV FPDLGVRVCE KMALYDWWST  2600
LPQAVMGSSY GFQYSPKQRV EFLVNIWKSK KCPMGFSYDT RCFDSTVIES  2650
DIRVEESIYQ CCDLAPEARQ AIRSLTERLY IGGPLINSKG QNCGYRRCRA  2700
SGVLTTSCGN TLTCYLKATA ACRAAKLQDC TMLVNGDDLV VICESAGTQE  2750
DAAALRAFTE AMTRYSAPPG DPPQPEYDLE LITSCSSNVS VAHDASGKRV  2800
YYLTRDPTTP LARAAWETAR HTPINSWLGN IIMYAPTLWA RMILMIHFFS  2850
ILAQEQLEK ALDCQIYGAC YSIEPLDLPQ IIERLHGLSA FTLHSYSPGE   2900
INRVASCLRK LGVPPLRIWR HRARSVRAKL LSQGGRAATC GRYLFNWAVR  2950
TKLKLTPIPA ASQLDLSGWF VAGYSGGDIY HSLSRARPRW FPLCLLLLSV  3000
GVGIYLLPNR                                              3010
```

FIG. 4H

SEQUENCE LISTING

<160> NUMBER OF SEQ ID NOS: 4

<210> SEQ ID NO 1
<211> LENGTH: 12119

-continued

```
<212> TYPE: DNA
<213> ORGANISM: Chimaera sp.

<400> SEQUENCE: 1
gtatacgaga attagaaaag gcactcgtat acgtattggg caattaaaaa taataattag      60
gcctagggaa caaatccctc tcagcgaagg ccgaaaagag gctagccatg cccttagtag     120
gactagcata atgaggggg tagcaacagt ggtgagttcg ttggatggct taagccctga     180
gtacagggta gtcgtcagtg gttcgacgcc ttggaataaa ggtctcgaga tgccacgtgg     240
acgagggcat gcccaaagca catcttaacc tgagcggggg tcgcccaggt aaaagcagtt     300
ttaaccgact gttacgaata cagcctgata gggtgctgca gaggcccact gtattgctac     360
taaaaatctc tgctgtacat ggcacatgga gttgatcaca aatgaacttt tatacaaaac     420
atacaaacaa aaacccgtcg gggtggagga acctgtttat gatcaggcag gtgatccctt     480
atttggtgaa agggagcag tccaccctca atcgacgcta agctcccac acaagagagg     540
ggaacgcgat gttccaacca acttggcatc cttaccaaaa agaggtgact gcaggtcggg     600
taatagcaga ggacctgtga gcgggatcta acctgaagcca gggccactat tttaccagga     660
ctataaaggt cccgtctatc acagggcccc gctggagctc tttgaggagg gatccatgtg     720
tgaaacgact aaacggatag ggagagtaac tggaagtgac ggaaagctgt accacattta     780
tgtgtgtata gatggatgta taataataaa aagtgccacg agaagttacc aaagggtgtt     840
caggtgggtc cataataggc ttgactgccc tctatgggtc acaagttgca gcacgaatcc     900
taaacctcaa agaaaaacca aacgtaacac caaccgtcgc ccacaggacg tcaagttccc     960
gggtggcggt cagatcgttg gtggagttta cttgttgccg cgcaggggcc ctagattggg    1020
tgtgcgcgcg acgaggaaga cttccgagcg gtcgcaacct cgaggtagac gtcagcctat    1080
ccccaaggca cgtcggcccg agggcaggac ctgggctcag cccgggtacc cttggccct    1140
ctatggcaat gagggttgcg ggtgggcggg atggctcctg tctccccgtg gctctcggcc    1200
tagctggggc cccacagacc cccggcgtag gtcgcgcaat ttgggtaagg tcatcgatac    1260
ccttacgtgc ggcttcgccg acctcatggg gtacataccg ctcgtcggcg ccctcttgg    1320
aggcgctgcc agggccctgg cgcatggcgt ccgggttctg gaagacggcg tgaactatgc    1380
aacagggaac cttcctggtt gctctttctc tatcttcctt ctggccctgc tctcttgcct    1440
gactgtgccc gcttcagcct accaagtgcg caattcctcg ggctttacc atgtcaccaa    1500
tgattgccct aactcgagta ttgtgtacga ggcggccgat gccatcctgc acactccggg    1560
gtgtgtccct tgcgttcgcg agggtaacgc ctcgaggtgt tgggtggcgg tgaccccccac   1620
ggtggccacc agggacggca aactccccac aacgcagctt cgacgtcata tcgatctgct    1680
tgtcgggagc gccaccctct gctcggccct ctacgtgggg gacctgtgcg ggtctgtctt    1740
tcttgttggt caactgttta ccttctctcc caggcgccac tggacgacgc aagactgcaa    1800
ttgttctatc tatcccggcc atataacggg tcatcgcatg gcatgggata tgatgatgaa    1860
ctggtcccct acggcagcgt tggtggtagc tcagctgctc cggatcccac aagccatcat    1920
ggacatgatc gctggtgctc actggggagt cctggcgggc atagcgtatt tctccatggt    1980
ggggaactgg gcgaaggtcc tggtagtgct gctgctattt gccggcgtcg acgcggaaac    2040
ccacgtcacc gggggaaatg ccggccgcac cacggctggg cttgttggtc tccttacacc    2100
aggcgccaag cagaacatcc aactgatcaa caccaacggc agttggcaca tcaatagcac    2160
ggccttgaat tgcaatgaaa gccttaacac cggctggtta gcaggggctct tctatcaaca    2220
```

-continued

```
caaattcaac tcttcaggct gtcctgagag gttggccagc tgccgacgcc ttaccgattt     2280
tgcccagggc tggggtccta tcagttatgc caacggaagc ggcctcgacg aacgcccta      2340
ctgctggcac tacccctccaa gaccttgtgg cattgtgccc gcaaagagcg tgtgtggccc    2400
ggtatattgc ttcactccca gccccgtggt ggtgggaacg accacaggt cgggcgcgcc      2460
tacctacagc tggggtgcaa atgatacgga tgtcttcgtc cttaacaaca ccaggccacc     2520
gctgggcaat tggttcggtt gtacctggat gaactcaact ggattcacca aagtgtgcgg     2580
agcgcccct tgtgtcatcg gaggggtggg caacaacacc ttgctctgcc ccactgattg      2640
cttccgcaaa catccggaag ccacatactc tcggtgcggc tccggtccct ggattacacc    2700
caggtgcatg gtcgactacc cgtataggct ttggcactat ccttgtacca tcaattacac    2760
catattcaaa gtcaggatgt acgtgggagg gtcgagcac aggctggaag cggcctgcaa      2820
ctggacgcgg ggcgaacgct gtgatctgga agacagggac aggtccgagc tcagcccgtt    2880
gctgctgtcc accacacagt ggcaggtcct tccgtgttct ttcacgaccc tgccagcctt    2940
gtccaccggc ctcatccacc tccaccagaa cattgtggac gtgcagtact tgtacggggt    3000
agggtcaagc atcgcgtcct gggccattaa gtgggagtac gtcgttctcc tgttccttct    3060
gcttgcagac gcgcgcgtct gctcctgctt gtggatgatg ttactcatat cccaagcgga    3120
ggcgattcag tatggatcag gggaagtggt gatgatgggc aacttgctaa cccataacaa    3180
tattgaagtg gtgacatact tcttgctgct gtacctactg ctgagggagg agagcgtaaa    3240
gaagtgggtc ttactcttat accacatctt agtggtacac ccaatcaaat ctgtaattgt    3300
gatcctactg atgattgggg atgtggtaaa ggccgattca ggggccaag agtacttggg     3360
gaaaatagac ctctgtttta caacagtagt actaatcgtc ataggtttaa tcatagccag    3420
gcgtgaccca actatagtgc cactggtaac aataatggca gcactgaggg tcactgaact    3480
gacccaccag cctggagttg acatcgctgt ggcggtcatg actataaccc tactgatggt    3540
tagctatgtg acagattatt ttagatataa aaaatggtta cagtgcattc tcagcctggt    3600
atctggggtg ttcttgataa gaagcctaat atacctaggt agaatcgaga tgccagaggt    3660
aactatccca aactggagac cactaacttt aatactatta tatttgatct caacaacaat    3720
tgtaacgagg tggaaggttg acgtggctgg cctattgttg caatgtgtgc ctatcttatt    3780
gctggtcaca accttgtggg ccgacttctt aaccctaata ctgatcctgc ctacctatga    3840
attggttaaa ttatactatc tgaaaactgt taggactgat atagaaagaa gttggctagg    3900
ggggatagac tatacaagag ttgactccat ctacgacgtt gatgagagtg gagagggcgt    3960
atatctttt ccatcaaggc agaaagcaca ggggaatttt tctatactct tgccccttat     4020
caaagcaaca ctgataagtt gcgtcagcag taaatggcag ctaatataca tgagttactt    4080
aactttggac tttatgtact acatgcacag gaaagttata aagagatct caggaggtac     4140
caacataata tccaggttag tggcagcact catagagctg aactggtcca tggaagaaga    4200
ggagagcaaa ggcttaaaga agttttatct attgtctgga aggttgagaa acctaataat    4260
aaaacataag gtaaggaatg agaccgtggc ttccttggtac ggggaggagg aagtctacgg   4320
tatgccaaag atcatgacta taatcaaggc cagtacactg agtaagagca ggcactgcat    4380
aatatgcact gtatgtgagg gccgagagtg gaaaggtggc acctgcccaa aatgtggacg    4440
ccatgggaag ccgataacgt gtgggatgtc gctagcagat tttgaagaaa gacactataa    4500
aagaatcttt ataagggaag gcaactttga gggtatgtgc agccgatgcc agggaaagca    4560
taggaggttt gaaatggacc gggaacctaa gagtgccaga tactgtgctg agtgtaatag    4620
```

```
gctgcatcct gctgaggaag gtgacttttg ggcagagtcg agcatgttgg gcctcaaaat      4680
cacctacttt gcgctgatgg atggaaaggt gtatgatatc acagagtggg ctggatgcca      4740
gcgtgtggga atctccccag ataccacag agtcccttgt cacatctcat ttggttcacg       4800
gatgcctttc aggcaggaat acaatggctt tgtacaatat accgctaggg ggcaactatt      4860
tctgagaaac ttgcccgtac tgcaactaa agtaaaaatg ctcatggtag caaccttgg        4920 agaagaaatt ggtaatctgg aacatcttgg gtggatccta aggggcctg ccgtgtgtaa       4980 gaagatcaca gagcacgaaa aatgccacat taatatactg gataaactaa ccgcattttt      5040
cgggatcatg ccaaggggga ctacacccag agccccggtg aggttccta cgagcttact       5100 aaaagtgagg aggggtctgg agactggctg ggcttacaca caccaaggcg ggataagttc      5160
agtcgaccat gtaaccgccg gaaaagatct actggtctgt gacagcatgg gacgaactag      5220
agtggtttgc caaagcaaca acaggttgac cgatgagaca gagtatggcg tcaagactga      5280
ctcagggtgc ccagacggtg ccagatgtta tgtgttaaat ccagaggccg ttaacatatc      5340
aggatccaaa gggcagtcg ttcacctcca aaagacaggt ggagaattca cgtgtgtcac       5400
cgcatcaggc acaccggctt tcttcgacct aaaaaacttg aaaggatggt caggcttgcc      5460
tatatttgaa gcctccagcg ggagggtggt tggcagagtc aaagtaggga agaatgaaga      5520
gtctaaacct acaaaaataa tgagtggaat ccagaccgtc tcaaaaaaca cagcagacct      5580
gaccgagatg gtcaagaaga taaccagcat gaacagggga gacttcaagc agattacttt      5640
ggcaacaggg gcaggcaaaa ccacagaact cccaaaagca gttatagagg agataggaag       5700
acacaagaga gtattagttc ttataccatt aagggcagcg gcagagtcag tctaccagta      5760
tatgagattg aaacacccaa gcatctcttt taacctaagg ataggggaca tgaaagaggg      5820
ggacatggca accgggataa cctatgcatc atacgggtac ttctgccaaa tgcctcaacc      5880
aaagctcaga gctgctatgg tagaatactc atacatattc ttagatgaat accattgtgc      5940
cactcctgaa caactggcaa ttatcgggaa gatccacaga ttttcagaga gtataagggt      6000
tgtcgccatg actgccacgc cagcagggtc ggtgaccaca acaggtcaaa agcacccaat      6060
agaggaattc atagccccg aggtaatgaa agggaggat cttggtagtc agttccttga        6120
tatagcaggg ttaaaaatac cagtggatga gatgaaaggc aatatgttgg tttttgtacc      6180
aacgagaaac atggcagtag aggtagcaaa aagctaaaa gctaagggct ataactctgg       6240
atactattac agtggagagg atccagccaa tctgagagtt gtgacatcac aatcccccta      6300
tgtaatcgtg gctacaaatg ctattgaatc aggagtgaca ctaccagatt tggacacggt      6360
tatagacacg ggggttgaaat gtgaaaagag ggtgagggta tcatcaaaga taccttcat     6420 cgtaacaggc cttaagagga tggccgtgac tgtgggtgag caggcgcagc gtaggggcag      6480
agtaggtaga gtgaaacccg ggaggtatta taggagccag gaaacagcaa cagggtcaaa     6540
ggactaccac tatgacctct gcaggcaca aagatacggg attgaggatg gaatcaacgt      6600
gacgaaatcc tttagggaga tgaattacga ttggagccta tacgaggagg acagcctact      6660
aataacccag ctggaaatac taatatct actcatctca gaagacttgc cagccgctgt       6720
taagaacata atggccagga ctgatcaccc agagccaatc aacttgcat acaacagcta       6780 tgaagtccag gtcccggtcc tgttcccaaa ataaggaat ggagaagtca cagacaccta      6840
cgaaaattac tcgtttctaa atgccagaaa gttaggggag gatgtgcccg tgtatatcta      6900
cgctactgaa gatgaggatc tggcagttga cctcttaggg ctagactggc ctgatcctgg      6960
```

```
gaaccagcag gtagtggaga ctggtaaagc actgaagcaa gtgaccgggt tgtcctcggc    7020
tgaaaatgcc ctactagtgg ctttatttgg gtatgtgggt taccaggctc tctcaaagag    7080
gcatgtccca atgataacag acatatatac catcgaggac cagagactag aagacaccac    7140
ccacctccag tatgcaccca acgccataaa aaccgatggg acagagactg aactgaaaga    7200
actggcgtcg ggtgacgtgg aaaaaatcat gggagccatt tcagattatg cagctggggg    7260
actggagttt gttaaatccc aagcagaaaa gataaaaaca gctcctttgt ttaaagaaaa    7320
cgcagaagcc gcaaaagggt atgtccaaaa attcattgac tcattaattg aaaataaaga    7380
agaaataatc agatatggtt tgtggggaac acacacagca ctatacaaaa gcatagctgc    7440
aagactgggg catgaaacag cgtttgccac actagtgtta aagtggctag cttttggagg    7500
ggaatcagtg tcagaccacg tcaagcaggc ggcagttgat ttagtggtct attatgtgat    7560
gaataagcct tccttcccag gtgactccga gacacagcaa gaagggaggc gattcgtcgc    7620
aagcctgttc atctccgcac tggcaaccta cacatacaaa acttggaatt accacaatct    7680
ctctaaagtg gtggaaccag ccctggctta cctcccctat gctaccagcg cattaaaaat    7740
gttcacccca acgcggctgg agagcgtggt gatactgagc accacgatat ataaaacata    7800
cctctctata aggaagggga agagtgatgg attgctgggt acggggataa gtgcagccat    7860
ggaaatcctg tcacaaaacc cagtatcggt aggtatatct gtgatgttgg gggtaggggc    7920
aatcgctgcg cacaacgcta ttgagtccag tgaacagaaa aggaccctac ttatgaaggt    7980
gtttgtaaag aacttcttgg atcaggctgc aacagatgag ctggtaaaag aaaacccaga    8040
aaaaattata atggccttat ttgaagcagt ccagacaatt ggtaaccccc tgagactaat    8100
ataccacctg tatggggttt actacaaagg ttgggaggcc aaggaactat ctgagaggac    8160
agcaggcaga aacttattca cattgataat gtttgaagcc ttcgagttat tagggatgga    8220
ctcacaaggg aaaataagga acctgtccgg aaattacatt ttggatttga tatacggcct    8280
acacaagcaa atcaacagag ggctgaagaa aatggtactg gggtgggccc ctgcaccctt    8340
tagttgtgac tggaccccta gtgacgagag gatcagattg ccaacagaca actatttgag    8400
ggtagaaacc aggtgcccat gtggctatga gatgaaagct ttcaaaaatg taggtggcaa    8460
acttaccaaa gtggaggaga gcgggccttt cctatgtaga aacagacctg gtaggggacc    8520
agtcaactac agagtcacca gtattacgga tgacaacctc agagagataa aaccagtagc    8580
aaagttggaa ggacaggtag agcactacta caaagggggtc acagcaaaaa ttgactacag    8640
taaaggaaaa atgctcttgg ccactgacaa gtgggaggtg aacatggtg tcataaccag    8700 gttagctaag agatatactg gggtcgggtt caatggtgca tacttaggtg acgagcccaa    8760
tcaccgtgct ctagtggaga gggactgtgc aactataacc aaaaacacag tacagtttct    8820
aaaaatgaag aagggtgtg cgttcaccta tgacctgacc atctccaatc tgaccaggct    8880
catcgaacta gtacacagga acaatcttga agagaaggaa atacccaccg ctacggtcac    8940
cacatggcta gcttacacct tcgtgaatga agacgtaggg actataaaac cagtactagg    9000
agagagagta atccccgacc ctgtagttga tatcaattta caaccagagg tgcaagtgga    9060
cacgtcagag gttgggatca caataattgg aagggaaacc ctgatgacaa cgggagtgac    9120
acctgtcttg gaaaaagtag agcctgacgc cagcgacaac caaaactcgg tgaagatcgg    9180
gttggatgag ggtaattacc cagggcctgg aatacagaca catacactaa cagaagaaat    9240
acacaacagg gatgcgaggc ccttcatcat gatcctgggc tcaaggaatt ccatatcaaa    9300
tagggcaaag actgctagaa atataaatct gtacacagga aatgaccca gggaaatacg    9360
```

```
agacttgatg gctgcagggc gcatgttagt agtagcactg agggatgtcg accctgagct   9420
gtctgaaatg gtcgatttca aggggacttt tttagatagg gaggccctgg aggctctaag   9480
tctcgggcaa cctaaaccga agcaggttac caaggaagct gttaggaatt tgatagaaca   9540
gaaaaaagat gtggagatcc ctaactggtt tgcatcagat gacccagtat ttctggaagt   9600
ggccttaaaa aatgataagt actacttagt aggagatgtt ggagaggtaa agatcaagc    9660 taaagcactt ggggccacgg atcagacaag aattataaag gaggtaggct caaggacgta   9720
tgccatgaag ctatctagct ggttcctcca ggcatcaaac aaacagatga gtttaactcc   9780
actgtttgag gaattgttgc tacggtgccc acctgcaact aagagcaata aggggcacat   9840
ggcatcagct taccaattgg cacagggtaa ctgggagccc ctcggttgcg gggtgcacct   9900
aggtacaata ccagccagaa gggtgaagat acacccatat gaagcttacc tgaagttgaa   9960
agatttcata aagaagaag agaagaaacc tagggttaag gatacagtaa taagagagca  10020
caacaaatgg atacttaaaa aataaggtt tcaaggaaac ctcaacacca agaaaatgct   10080
caaccctggg aaactatctg aacagttgga caggagggg cgcaagagga acatctacaa   10140
ccaccagatt ggtactataa tgtcaagtgc aggcataagg ctggagaaat tgccaatagt   10200
gagggcccaa accgacacca aaacctttca tgaggcaata agagataaga tagacaagag   10260
tgaaaaccgg caaaatccag aattgcacaa caaattgttg gagattttcc acacgatagc   10320
ccaacccacc ctgaaacaca cctacggtga ggtgacgtgg gagcaacttg aggcggggat   10380
aaatagaaag ggggcagcag gcttcctgga agaagaac atcggagaag tattggattc    10440
agaaaagcac ctggtagaac aattggtcag ggatctgaag gccgggagaa agataaaata   10500
ttatgaaact gcaataccaa aaatgaaga gagagatgtc agtgatgact ggcaggcagg    10560
ggacctggtg gttgagaaga ggccaagagt tatccaatac cctgaagcca agacaaggct   10620
agccatcact aaggtcatgt ataactgggt gaaacagcag cccgttgtga ttccaggata   10680
tgaaggaaag accccccttgt tcaacatctt tgataaagtg agaaaggaat gggactcgtt   10740
caatgagcca gtggccgtaa gttttgacac caaagcctgg gacactcaag tgactagtaa   10800
ggatctgcaa cttattggag aaatccagaa atattactat aagaaggagt ggcacaagtt  10860
cattgacacc atcaccgacc acatgacaga agtaccagtt ataacagcag atggtgaagt   10920
atatataaga aatgggcaga gagggagcgg ccagccagac acaagtgctg caacagcat    10980 gttaaatgtc ctgacaatga tgtacgcctt ctgcgaaagc acaggggtac cgtacaagag   11040
tttcaacagg gtgcaagga tccacgtctg tgggatgat ggcttcttaa taactgaaaa    11100
agggttaggc ctgaaatttg ctaacaaagg gatgcagatt cttcatgaag caggcaaacc    11160
tcagaagata acggaagggg aaaagatgaa agttgcctat agatttgagg atatagagtt   11220
ctgttctcat accccagtcc ctgttaggtg gtccgacaac accagtagtc acatggccgg   11280
gagagacacc gctgtgatac tatcaaagat ggcaacaaga ttggattcaa gtggagagag    11340
gggtaccact gcatatgaaa aagcggtagc cttcagtttc ttgctgatgt attcctggaa    11400
cccgcttgtt aggaggattt gcctgttggt cctttcgcaa cagccagaga cagacccatc   11460
aaaacatgcc acttattatt acaaaggtga tccaataggg gcctataaag atgtaatagg    11520
tcggaatcta agtgaactga gagaacagg cttttgagaaa ttggcaaatc taaacctaag   11580
cctgtccacg ttggggatct ggactaagca cacaagcaaa agaataattc aggactgtgt   11640
tgccattggg aaagaagagg gcaactggct agttaacgcc gacaggctga tatccagcaa   11700
```

-continued

```
aactggccac ttatacatac ctgataaagg ctttacatta caaggaaagc attatgagca    11760
actgcagcta agaacagaga caaacccggt catgggggtt gggactgaga gatacaagtt    11820
aggtcccata gtcaatctgc tgctgagaag gttgaaaatt ctgctcatga cggccgtcgg    11880
cgtcagcagc tgagacaaaa tgtatatatt gtaaataaat taatccatgt acatagtgta    11940
tataaatata gttgggaccg tccacctcaa gaagacgaca cgcccaacac gcacagctaa    12000
acagtagtca agattatcta cctcaagata acactacatt taatgcacac agcactttag    12060
ctgtatgagg atacgcccga cgtctatagt tggactaggg aagacctcta acagccccc     12119
```

<210> SEQ ID NO 2
<211> LENGTH: 3835
<212> TYPE: PRT
<213> ORGANISM: Chimaera sp.

<400> SEQUENCE: 2

```
Met Glu Leu Ile Thr Asn Glu Leu Leu Tyr Lys Thr Tyr Lys Gln Lys
  1               5                  10                  15

Pro Val Gly Val Glu Glu Pro Val Tyr Asp Gln Ala Gly Asp Pro Leu
             20                  25                  30

Phe Gly Glu Arg Gly Ala Val His Pro Gln Ser Thr Leu Lys Leu Pro
         35                  40                  45

His Lys Arg Gly Glu Arg Asp Val Pro Thr Asn Leu Ala Ser Leu Pro
     50                  55                  60

Lys Arg Gly Asp Cys Arg Ser Gly Asn Ser Arg Gly Pro Val Ser Gly
 65                  70                  75                  80

Ile Tyr Leu Lys Pro Gly Pro Leu Phe Tyr Gln Asp Tyr Lys Gly Pro
                 85                  90                  95

Val Tyr His Arg Ala Pro Leu Glu Leu Phe Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Val Cys Ile Asp Gly Cys Ile Ile Ile Lys Ser Ala
    130                 135                 140

Thr Arg Ser Tyr Gln Arg Val Phe Arg Trp Val His Asn Arg Leu Asp
145                 150                 155                 160

Cys Pro Leu Trp Val Thr Ser Cys Ser Thr Asn Pro Lys Pro Gln Arg
                165                 170                 175

Lys Thr Lys Arg Asn Thr Asn Arg Arg Pro Gln Asp Val Lys Phe Pro
            180                 185                 190

Gly Gly Gly Gln Ile Val Gly Gly Val Tyr Leu Leu Pro Arg Arg Gly
        195                 200                 205

Pro Arg Leu Gly Val Arg Ala Thr Arg Lys Thr Ser Glu Arg Ser Gln
    210                 215                 220

Pro Arg Gly Arg Gln Pro Ile Pro Lys Ala Arg Arg Pro Glu Gly
225                 230                 235                 240

Arg Thr Trp Ala Gln Pro Gly Tyr Pro Trp Pro Leu Tyr Gly Asn Glu
                245                 250                 255

Gly Cys Gly Trp Ala Gly Trp Leu Leu Ser Pro Arg Gly Ser Arg Pro
            260                 265                 270

Ser Trp Gly Pro Thr Asp Pro Arg Arg Ser Arg Asn Leu Gly Lys
        275                 280                 285

Val Ile Asp Thr Leu Thr Cys Gly Phe Ala Asp Leu Met Gly Tyr Ile
    290                 295                 300
```

```
Pro Leu Val Gly Ala Pro Leu Gly Gly Ala Ala Arg Ala Leu Ala His
305                 310                 315                 320

Gly Val Arg Val Leu Glu Asp Gly Val Asn Tyr Ala Thr Gly Asn Leu
            325                 330                 335

Pro Gly Cys Ser Phe Ser Ile Phe Leu Ala Leu Leu Ser Cys Leu
            340                 345                 350

Thr Val Pro Ala Ser Ala Tyr Gln Val Arg Asn Ser Ser Gly Leu Tyr
            355                 360                 365

His Val Thr Asn Asp Cys Pro Asn Ser Ser Ile Val Tyr Glu Ala Ala
    370                 375                 380

Asp Ala Ile Leu His Thr Pro Gly Cys Val Pro Cys Val Arg Glu Gly
385                 390                 395                 400

Asn Ala Ser Arg Cys Trp Val Ala Val Thr Pro Thr Val Ala Thr Arg
                405                 410                 415

Asp Gly Lys Leu Pro Thr Thr Gln Leu Arg Arg His Ile Asp Leu Leu
            420                 425                 430

Val Gly Ser Ala Thr Leu Cys Ser Ala Leu Tyr Val Gly Asp Leu Cys
            435                 440                 445

Gly Ser Val Phe Leu Val Gly Gln Leu Phe Thr Phe Ser Pro Arg Arg
    450                 455                 460

His Trp Thr Thr Gln Asp Cys Asn Cys Ser Ile Tyr Pro Gly His Ile
465                 470                 475                 480

Thr Gly His Arg Met Ala Trp Asp Met Met Met Asn Trp Ser Pro Thr
                485                 490                 495

Ala Ala Leu Val Val Ala Gln Leu Leu Arg Ile Pro Gln Ala Ile Met
            500                 505                 510

Asp Met Ile Ala Gly Ala His Trp Gly Val Leu Ala Gly Ile Ala Tyr
            515                 520                 525

Phe Ser Met Val Gly Asn Trp Ala Lys Val Leu Val Val Leu Leu Leu
    530                 535                 540

Phe Ala Gly Val Asp Ala Glu Thr His Val Thr Gly Gly Asn Ala Gly
545                 550                 555                 560

Arg Thr Thr Ala Gly Leu Val Gly Leu Leu Thr Pro Gly Ala Lys Gln
                565                 570                 575

Asn Ile Gln Leu Ile Asn Thr Asn Gly Ser Trp His Ile Asn Ser Thr
            580                 585                 590

Ala Leu Asn Cys Asn Glu Ser Leu Asn Thr Gly Trp Leu Ala Gly Leu
    595                 600                 605

Phe Tyr Gln His Lys Phe Asn Ser Ser Gly Cys Pro Glu Arg Leu Ala
610                 615                 620

Ser Cys Arg Arg Leu Thr Asp Phe Ala Gln Gly Trp Gly Pro Ile Ser
625                 630                 635                 640

Tyr Ala Asn Gly Ser Gly Leu Asp Glu Arg Pro Tyr Cys Trp His Tyr
                645                 650                 655

Pro Pro Arg Pro Cys Gly Ile Val Pro Ala Lys Ser Val Cys Gly Pro
            660                 665                 670

Val Tyr Cys Phe Thr Pro Ser Pro Val Val Val Gly Thr Thr Asp Arg
            675                 680                 685

Ser Gly Ala Pro Thr Tyr Ser Trp Gly Ala Asn Asp Thr Asp Val Phe
    690                 695                 700

Val Leu Asn Asn Thr Arg Pro Pro Leu Gly Asn Trp Phe Gly Cys Thr
705                 710                 715                 720

Trp Met Asn Ser Thr Gly Phe Thr Lys Val Cys Gly Ala Pro Pro Cys
```

-continued

```
                725                 730                 735
Val Ile Gly Gly Val Gly Asn Asn Thr Leu Leu Cys Pro Thr Asp Cys
            740                 745                 750

Phe Arg Lys His Pro Glu Ala Thr Tyr Ser Arg Cys Gly Ser Gly Pro
            755                 760                 765

Trp Ile Thr Pro Arg Cys Met Val Asp Tyr Pro Tyr Arg Leu Trp His
            770                 775                 780

Tyr Pro Cys Thr Ile Asn Tyr Thr Ile Phe Lys Val Arg Met Tyr Val
785                 790                 795                 800

Gly Gly Val Glu His Arg Leu Glu Ala Ala Cys Asn Trp Thr Arg Gly
                805                 810                 815

Glu Arg Cys Asp Leu Glu Asp Arg Asp Arg Ser Glu Leu Ser Pro Leu
            820                 825                 830

Leu Leu Ser Thr Thr Gln Trp Gln Val Leu Pro Cys Ser Phe Thr Thr
            835                 840                 845

Leu Pro Ala Leu Ser Thr Gly Leu Ile His Leu His Gln Asn Ile Val
850                 855                 860

Asp Val Gln Tyr Leu Tyr Gly Val Gly Ser Ser Ile Ala Ser Trp Ala
865                 870                 875                 880

Ile Lys Trp Glu Tyr Val Val Leu Leu Phe Leu Leu Leu Ala Asp Ala
                885                 890                 895

Arg Val Cys Ser Cys Leu Trp Met Met Leu Leu Ile Ser Gln Ala Glu
            900                 905                 910

Ala Ile Gln Tyr Gly Ser Gly Glu Val Val Met Met Gly Asn Leu Leu
            915                 920                 925

Thr His Asn Asn Ile Glu Val Val Thr Tyr Phe Leu Leu Leu Tyr Leu
            930                 935                 940

Leu Leu Arg Glu Glu Ser Val Lys Lys Trp Val Leu Leu Tyr His
945                 950                 955                 960

Ile Leu Val Val His Pro Ile Lys Ser Val Ile Val Ile Leu Leu Met
                965                 970                 975

Ile Gly Asp Val Val Lys Ala Asp Ser Gly Gly Gln Glu Tyr Leu Gly
            980                 985                 990

Lys Ile Asp Leu Cys Phe Thr Thr Val Val Leu Ile Val Ile Gly Leu
            995                 1000                1005

Ile Ile Ala Arg Arg Asp Pro Thr Ile Val Pro Leu Val Thr Ile Met
    1010                1015                1020

Ala Ala Leu Arg Val Thr Glu Leu Thr His Gln Pro Gly Val Asp Ile
1025                1030                1035                1040

Ala Val Ala Val Met Thr Ile Thr Leu Leu Met Val Ser Tyr Val Thr
                1045                1050                1055

Asp Tyr Phe Arg Tyr Lys Lys Trp Leu Gln Cys Ile Leu Ser Leu Val
            1060                1065                1070

Ser Gly Val Phe Leu Ile Arg Ser Leu Ile Tyr Leu Gly Arg Ile Glu
            1075                1080                1085

Met Pro Glu Val Thr Ile Pro Asn Trp Arg Pro Leu Thr Leu Ile Leu
            1090                1095                1100

Leu Tyr Leu Ile Ser Thr Thr Ile Val Thr Arg Trp Lys Val Asp Val
1105                1110                1115                1120

Ala Gly Leu Leu Leu Gln Cys Val Pro Ile Leu Leu Leu Val Thr Thr
                1125                1130                1135

Leu Trp Ala Asp Phe Leu Thr Leu Ile Leu Ile Leu Pro Thr Tyr Glu
            1140                1145                1150
```

```
Leu Val Lys Leu Tyr Tyr Leu Lys Thr Val Arg Thr Asp Ile Glu Arg
     1155                1160                1165

Ser Trp Leu Gly Gly Ile Asp Tyr Thr Arg Val Asp Ser Ile Tyr Asp
     1170                1175                1180

Val Asp Glu Ser Gly Glu Gly Val Tyr Leu Phe Pro Ser Arg Gln Lys
1185                1190                1195                1200

Ala Gln Gly Asn Phe Ser Ile Leu Leu Pro Leu Ile Lys Ala Thr Leu
                1205                1210                1215

Ile Ser Cys Val Ser Ser Lys Trp Gln Leu Ile Tyr Met Ser Tyr Leu
                1220                1225                1230

Thr Leu Asp Phe Met Tyr Tyr Met His Arg Lys Val Ile Glu Glu Ile
     1235                1240                1245

Ser Gly Gly Thr Asn Ile Ile Ser Arg Leu Val Ala Ala Leu Ile Glu
     1250                1255                1260

Leu Asn Trp Ser Met Glu Glu Glu Ser Lys Gly Leu Lys Lys Phe
1265                1270                1275                1280

Tyr Leu Leu Ser Gly Arg Leu Arg Asn Leu Ile Ile Lys His Lys Val
                1285                1290                1295

Arg Asn Glu Thr Val Ala Ser Trp Tyr Gly Glu Glu Val Tyr Gly
                1300                1305                1310

Met Pro Lys Ile Met Thr Ile Ile Lys Ala Ser Thr Leu Ser Lys Ser
     1315                1320                1325

Arg His Cys Ile Ile Cys Thr Val Cys Glu Gly Arg Glu Trp Lys Gly
     1330                1335                1340

Gly Thr Cys Pro Lys Cys Gly Arg His Gly Lys Pro Ile Thr Cys Gly
1345                1350                1355                1360

Met Ser Leu Ala Asp Phe Glu Glu Arg His Tyr Lys Arg Ile Phe Ile
                1365                1370                1375

Arg Glu Gly Asn Phe Glu Gly Met Cys Ser Arg Cys Gln Gly Lys His
                1380                1385                1390

Arg Arg Phe Glu Met Asp Arg Glu Pro Lys Ser Ala Arg Tyr Cys Ala
     1395                1400                1405

Glu Cys Asn Arg Leu His Pro Ala Glu Glu Gly Asp Phe Trp Ala Glu
     1410                1415                1420

Ser Ser Met Leu Gly Leu Lys Ile Thr Tyr Phe Ala Leu Met Asp Gly
1425                1430                1435                1440

Lys Val Tyr Asp Ile Thr Glu Trp Ala Gly Cys Gln Arg Val Gly Ile
                1445                1450                1455

Ser Pro Asp Thr His Arg Val Pro Cys His Ile Ser Phe Gly Ser Arg
                1460                1465                1470

Met Pro Phe Arg Gln Glu Tyr Asn Gly Phe Val Gln Tyr Thr Ala Arg
     1475                1480                1485

Gly Gln Leu Phe Leu Arg Asn Leu Pro Val Leu Ala Thr Lys Val Lys
     1490                1495                1500

Met Leu Met Val Gly Asn Leu Gly Glu Glu Ile Gly Asn Leu Glu His
1505                1510                1515                1520

Leu Gly Trp Ile Leu Arg Gly Pro Ala Val Cys Lys Lys Ile Thr Glu
                1525                1530                1535

His Glu Lys Cys His Ile Asn Ile Leu Asp Lys Leu Thr Ala Phe Phe
                1540                1545                1550

Gly Ile Met Pro Arg Gly Thr Thr Pro Arg Ala Pro Val Arg Phe Pro
     1555                1560                1565
```

```
Thr Ser Leu Leu Lys Val Arg Arg Gly Leu Glu Thr Gly Trp Ala Tyr
    1570                1575                1580

Thr His Gln Gly Gly Ile Ser Ser Val Asp His Val Thr Ala Gly Lys
1585                1590                1595                1600

Asp Leu Leu Val Cys Asp Ser Met Gly Arg Thr Arg Val Val Cys Gln
            1605                1610                1615

Ser Asn Asn Arg Leu Thr Asp Glu Thr Glu Tyr Gly Val Lys Thr Asp
        1620                1625                1630

Ser Gly Cys Pro Asp Gly Ala Arg Cys Tyr Val Leu Asn Pro Glu Ala
    1635                1640                1645

Val Asn Ile Ser Gly Ser Lys Gly Ala Val Val His Leu Gln Lys Thr
1650                1655                1660

Gly Gly Glu Phe Thr Cys Val Thr Ala Ser Gly Thr Pro Ala Phe Phe
1665                1670                1675                1680

Asp Leu Lys Asn Leu Lys Gly Trp Ser Gly Leu Pro Ile Phe Glu Ala
            1685                1690                1695

Ser Ser Gly Arg Val Val Gly Arg Val Lys Val Gly Lys Asn Glu Glu
        1700                1705                1710

Ser Lys Pro Thr Lys Ile Met Ser Gly Ile Gln Thr Val Ser Lys Asn
    1715                1720                1725

Thr Ala Asp Leu Thr Glu Met Val Lys Ile Thr Ser Met Asn Arg
1730                1735                1740

Gly Asp Phe Lys Gln Ile Thr Leu Ala Thr Gly Ala Gly Lys Thr Thr
1745                1750                1755                1760

Glu Leu Pro Lys Ala Val Ile Glu Glu Ile Gly Arg His Lys Arg Val
            1765                1770                1775

Leu Val Leu Ile Pro Leu Arg Ala Ala Ala Glu Ser Val Tyr Gln Tyr
        1780                1785                1790

Met Arg Leu Lys His Pro Ser Ile Ser Phe Asn Leu Arg Ile Gly Asp
    1795                1800                1805

Met Lys Glu Gly Asp Met Ala Thr Gly Ile Thr Tyr Ala Ser Tyr Gly
    1810                1815                1820

Tyr Phe Cys Gln Met Pro Gln Pro Lys Leu Arg Ala Ala Met Val Glu
1825                1830                1835                1840

Tyr Ser Tyr Ile Phe Leu Asp Glu Tyr His Cys Ala Thr Pro Glu Gln
            1845                1850                1855

Leu Ala Ile Ile Gly Lys Ile His Arg Phe Ser Glu Ser Ile Arg Val
        1860                1865                1870

Val Ala Met Thr Ala Thr Pro Ala Gly Ser Val Thr Thr Thr Gly Gln
    1875                1880                1885

Lys His Pro Ile Glu Glu Phe Ile Ala Pro Glu Val Met Lys Gly Glu
    1890                1895                1900

Asp Leu Gly Ser Gln Phe Leu Asp Ile Ala Gly Leu Lys Ile Pro Val
1905                1910                1915                1920

Asp Glu Met Lys Gly Asn Met Leu Val Phe Val Pro Thr Arg Asn Met
            1925                1930                1935

Ala Val Glu Val Ala Lys Lys Leu Lys Ala Lys Gly Tyr Asn Ser Gly
        1940                1945                1950

Tyr Tyr Tyr Ser Gly Glu Asp Pro Ala Asn Leu Arg Val Val Thr Ser
    1955                1960                1965

Gln Ser Pro Tyr Val Ile Val Ala Thr Asn Ala Ile Glu Ser Gly Val
    1970                1975                1980

Thr Leu Pro Asp Leu Asp Thr Val Ile Asp Thr Gly Leu Lys Cys Glu
```

-continued

```
          1985                1990                1995                2000
Lys Arg Val Arg Val Ser Ser Lys Ile Pro Phe Ile Val Thr Gly Leu
              2005                2010                2015
Lys Arg Met Ala Val Thr Val Gly Glu Gln Ala Gln Arg Arg Gly Arg
              2020                2025                2030
Val Gly Arg Val Lys Pro Gly Arg Tyr Tyr Arg Ser Gln Glu Thr Ala
              2035                2040                2045
Thr Gly Ser Lys Asp Tyr His Tyr Asp Leu Leu Gln Ala Gln Arg Tyr
              2050                2055                2060
Gly Ile Glu Asp Gly Ile Asn Val Thr Lys Ser Phe Arg Glu Met Asn
2065                2070                2075                2080
Tyr Asp Trp Ser Leu Tyr Glu Glu Asp Ser Leu Leu Ile Thr Gln Leu
              2085                2090                2095
Glu Ile Leu Asn Asn Leu Leu Ile Ser Glu Asp Leu Pro Ala Ala Val
              2100                2105                2110
Lys Asn Ile Met Ala Arg Thr Asp His Pro Glu Pro Ile Gln Leu Ala
              2115                2120                2125
Tyr Asn Ser Tyr Glu Val Gln Val Pro Val Leu Phe Pro Lys Ile Arg
              2130                2135                2140
Asn Gly Glu Val Thr Asp Thr Tyr Glu Asn Tyr Ser Phe Leu Asn Ala
2145                2150                2155                2160
Arg Lys Leu Gly Glu Asp Val Pro Val Tyr Ile Tyr Ala Thr Glu Asp
              2165                2170                2175
Glu Asp Leu Ala Val Asp Leu Leu Gly Leu Asp Trp Pro Asp Pro Gly
              2180                2185                2190
Asn Gln Gln Val Val Glu Thr Gly Lys Ala Leu Lys Gln Val Thr Gly
              2195                2200                2205
Leu Ser Ser Ala Glu Asn Ala Leu Leu Val Ala Leu Phe Gly Tyr Val
              2210                2215                2220
Gly Tyr Gln Ala Leu Ser Lys Arg His Val Pro Met Ile Thr Asp Ile
2225                2230                2235                2240
Tyr Thr Ile Glu Asp Gln Arg Leu Glu Asp Thr Thr His Leu Gln Tyr
              2245                2250                2255
Ala Pro Asn Ala Ile Lys Thr Asp Gly Thr Glu Thr Glu Leu Lys Glu
              2260                2265                2270
Leu Ala Ser Gly Asp Val Glu Lys Ile Met Gly Ala Ile Ser Asp Tyr
              2275                2280                2285
Ala Ala Gly Gly Leu Glu Phe Val Lys Ser Gln Ala Glu Lys Ile Lys
              2290                2295                2300
Thr Ala Pro Leu Phe Lys Glu Asn Ala Glu Ala Ala Lys Gly Tyr Val
2305                2310                2315                2320
Gln Lys Phe Ile Asp Ser Leu Ile Glu Asn Lys Glu Glu Ile Ile Arg
              2325                2330                2335
Tyr Gly Leu Trp Gly Thr His Thr Ala Leu Tyr Lys Ser Ile Ala Ala
              2340                2345                2350
Arg Leu Gly His Glu Thr Ala Phe Ala Thr Leu Val Leu Lys Trp Leu
              2355                2360                2365
Ala Phe Gly Gly Glu Ser Val Ser Asp His Val Lys Gln Ala Ala Val
              2370                2375                2380
Asp Leu Val Val Tyr Tyr Val Met Asn Lys Pro Ser Phe Pro Gly Asp
2385                2390                2395                2400
Ser Glu Thr Gln Gln Glu Gly Arg Arg Phe Val Ala Ser Leu Phe Ile
              2405                2410                2415
```

```
Ser Ala Leu Ala Thr Tyr Thr Tyr Lys Thr Trp Asn Tyr His Asn Leu
        2420                2425                2430

Ser Lys Val Val Glu Pro Ala Leu Ala Tyr Leu Pro Tyr Ala Thr Ser
    2435                2440                2445

Ala Leu Lys Met Phe Thr Pro Thr Arg Leu Glu Ser Val Val Ile Leu
2450                2455                2460

Ser Thr Thr Ile Tyr Lys Thr Tyr Leu Ser Ile Arg Lys Gly Lys Ser
2465                2470                2475                2480

Asp Gly Leu Leu Gly Thr Gly Ile Ser Ala Ala Met Glu Ile Leu Ser
            2485                2490                2495

Gln Asn Pro Val Ser Val Gly Ile Ser Val Met Leu Gly Val Gly Ala
        2500                2505                2510

Ile Ala Ala His Asn Ala Ile Glu Ser Ser Glu Gln Lys Arg Thr Leu
    2515                2520                2525

Leu Met Lys Val Phe Val Lys Asn Phe Leu Asp Gln Ala Ala Thr Asp
2530                2535                2540

Glu Leu Val Lys Glu Asn Pro Glu Lys Ile Ile Met Ala Leu Phe Glu
2545                2550                2555                2560

Ala Val Gln Thr Ile Gly Asn Pro Leu Arg Leu Ile Tyr His Leu Tyr
            2565                2570                2575

Gly Val Tyr Tyr Lys Gly Trp Glu Ala Lys Glu Leu Ser Glu Arg Thr
        2580                2585                2590

Ala Gly Arg Asn Leu Phe Thr Leu Ile Met Phe Glu Ala Phe Glu Leu
    2595                2600                2605

Leu Gly Met Asp Ser Gln Gly Lys Ile Arg Asn Leu Ser Gly Asn Tyr
2610                2615                2620

Ile Leu Asp Leu Ile Tyr Gly Leu His Lys Gln Ile Asn Arg Gly Leu
2625                2630                2635                2640

Lys Lys Met Val Leu Gly Trp Ala Pro Ala Pro Phe Ser Cys Asp Trp
            2645                2650                2655

Thr Pro Ser Asp Glu Arg Ile Arg Leu Pro Thr Asp Asn Tyr Leu Arg
        2660                2665                2670

Val Glu Thr Arg Cys Pro Cys Gly Tyr Glu Met Lys Ala Phe Lys Asn
    2675                2680                2685

Val Gly Gly Lys Leu Thr Lys Val Glu Glu Ser Gly Pro Phe Leu Cys
2690                2695                2700

Arg Asn Arg Pro Gly Arg Gly Pro Val Asn Tyr Arg Val Thr Lys Tyr
2705                2710                2715                2720

Tyr Asp Asp Asn Leu Arg Glu Ile Lys Pro Val Ala Lys Leu Glu Gly
            2725                2730                2735

Gln Val Glu His Tyr Tyr Lys Gly Val Thr Ala Lys Ile Asp Tyr Ser
        2740                2745                2750

Lys Gly Lys Met Leu Leu Ala Thr Asp Lys Trp Glu Val Glu His Gly
    2755                2760                2765

Val Ile Thr Arg Leu Ala Lys Arg Tyr Thr Gly Val Gly Phe Asn Gly
2770                2775                2780

Ala Tyr Leu Gly Asp Glu Pro Asn His Arg Ala Leu Val Glu Arg Asp
2785                2790                2795                2800

Cys Ala Thr Ile Thr Lys Asn Thr Val Gln Phe Leu Lys Met Lys Lys
            2805                2810                2815

Gly Cys Ala Phe Thr Tyr Asp Leu Thr Ile Ser Asn Leu Thr Arg Leu
        2820                2825                2830
```

-continued

Ile Glu Leu Val His Arg Asn Asn Leu Glu Glu Lys Glu Ile Pro Thr
            2835                2840                2845

Ala Thr Val Thr Thr Trp Leu Ala Tyr Thr Phe Val Asn Glu Asp Val
        2850                2855                2860

Gly Thr Ile Lys Pro Val Leu Gly Glu Arg Val Ile Pro Asp Pro Val
2865                2870                2875                2880

Val Asp Ile Asn Leu Gln Pro Glu Val Gln Val Asp Thr Ser Glu Val
            2885                2890                2895

Gly Ile Thr Ile Ile Gly Arg Glu Thr Leu Met Thr Thr Gly Val Thr
        2900                2905                2910

Pro Val Leu Glu Lys Val Glu Pro Asp Ala Ser Asp Asn Gln Asn Ser
            2915                2920                2925

Val Lys Ile Gly Leu Asp Glu Gly Asn Tyr Pro Gly Pro Gly Ile Gln
            2930                2935                2940

Thr His Thr Leu Thr Glu Glu Ile His Asn Arg Asp Ala Arg Pro Phe
2945                2950                2955                2960

Ile Met Ile Leu Gly Ser Arg Asn Ser Ile Ser Asn Arg Ala Lys Thr
                2965                2970                2975

Ala Arg Asn Ile Asn Leu Tyr Thr Gly Asn Asp Pro Arg Glu Ile Arg
            2980                2985                2990

Asp Leu Met Ala Ala Gly Arg Met Leu Val Val Ala Leu Arg Asp Val
            2995                3000                3005

Asp Pro Glu Leu Ser Glu Met Val Asp Phe Lys Gly Thr Phe Leu Asp
        3010                3015                3020

Arg Glu Ala Leu Glu Ala Leu Ser Leu Gly Gln Pro Lys Pro Lys Gln
3025                3030                3035                3040

Val Thr Lys Glu Ala Val Arg Asn Leu Ile Glu Gln Lys Lys Asp Val
                3045                3050                3055

Glu Ile Pro Asn Trp Phe Ala Ser Asp Asp Pro Val Phe Leu Glu Val
            3060                3065                3070

Ala Leu Lys Asn Asp Lys Tyr Tyr Leu Val Gly Asp Val Gly Glu Val
            3075                3080                3085

Lys Asp Gln Ala Lys Ala Leu Gly Ala Thr Asp Gln Thr Arg Ile Ile
    3090                3095                3100

Lys Glu Val Gly Ser Arg Thr Tyr Ala Met Lys Leu Ser Ser Trp Phe
3105                3110                3115                3120

Leu Gln Ala Ser Asn Lys Gln Met Ser Leu Thr Pro Leu Phe Glu Glu
            3125                3130                3135

Leu Leu Leu Arg Cys Pro Pro Ala Thr Lys Ser Asn Lys Gly His Met
                3140                3145                3150

Ala Ser Ala Tyr Gln Leu Ala Gln Gly Asn Trp Glu Pro Leu Gly Cys
            3155                3160                3165

Gly Val His Leu Gly Thr Ile Pro Ala Arg Arg Val Lys Ile His Pro
    3170                3175                3180

Tyr Glu Ala Tyr Leu Lys Leu Lys Asp Phe Ile Glu Glu Glu Glu Lys
3185                3190                3195                3200

Lys Pro Arg Val Lys Asp Thr Val Ile Arg Glu His Asn Lys Trp Ile
                3205                3210                3215

Leu Lys Lys Ile Arg Phe Gln Gly Asn Leu Asn Thr Lys Lys Met Leu
            3220                3225                3230

Asn Pro Gly Lys Leu Ser Glu Gln Leu Asp Arg Glu Gly Arg Lys Arg
            3235                3240                3245

Asn Ile Tyr Asn His Gln Ile Gly Thr Ile Met Ser Ser Ala Gly Ile

-continued

```
           3250                3255                3260
Arg Leu Glu Lys Leu Pro Ile Val Arg Ala Gln Thr Asp Thr Lys Thr
3265                3270                3275                3280

Phe His Glu Ala Ile Arg Asp Lys Ile Asp Lys Ser Glu Asn Arg Gln
           3285                3290                3295

Asn Pro Glu Leu His Asn Lys Leu Leu Glu Ile Phe His Thr Ile Ala
      3300                3305                3310

Gln Pro Thr Leu Lys His Thr Tyr Gly Glu Val Thr Trp Glu Gln Leu
      3315                3320                3325

Glu Ala Gly Ile Asn Arg Lys Gly Ala Ala Gly Phe Leu Glu Lys Lys
3330                3335                3340

Asn Ile Gly Glu Val Leu Asp Ser Glu Lys His Leu Val Glu Gln Leu
3345                3350                3355                3360

Val Arg Asp Leu Lys Ala Gly Arg Lys Ile Lys Tyr Tyr Glu Thr Ala
           3365                3370                3375

Ile Pro Lys Asn Glu Lys Arg Asp Val Ser Asp Trp Gln Ala Gly
      3380                3385                3390

Asp Leu Val Val Glu Lys Arg Pro Arg Val Ile Gln Tyr Pro Glu Ala
      3395                3400                3405

Lys Thr Arg Leu Ala Ile Thr Lys Val Met Tyr Asn Trp Val Lys Gln
   3410                3415                3420

Gln Pro Val Val Ile Pro Gly Tyr Glu Gly Lys Thr Pro Leu Phe Asn
3425                3430                3435                3440

Ile Phe Asp Lys Val Arg Lys Glu Trp Asp Ser Phe Asn Glu Pro Val
           3445                3450                3455

Ala Val Ser Phe Asp Thr Lys Ala Trp Asp Thr Gln Val Thr Ser Lys
      3460                3465                3470

Asp Leu Gln Leu Ile Gly Glu Ile Gln Lys Tyr Tyr Tyr Lys Lys Glu
      3475                3480                3485

Trp His Lys Phe Ile Asp Thr Ile Thr Asp His Met Thr Glu Val Pro
   3490                3495                3500

Val Ile Thr Ala Asp Gly Glu Val Tyr Ile Arg Asn Gly Gln Arg Gly
3505                3510                3515                3520

Ser Gly Gln Pro Asp Thr Ser Ala Gly Asn Ser Met Leu Asn Val Leu
           3525                3530                3535

Thr Met Met Tyr Ala Phe Cys Glu Ser Thr Gly Val Pro Tyr Lys Ser
      3540                3545                3550

Phe Asn Arg Val Ala Arg Ile His Val Cys Gly Asp Asp Gly Phe Leu
      3555                3560                3565

Ile Thr Glu Lys Gly Leu Gly Leu Lys Phe Ala Asn Lys Gly Met Gln
   3570                3575                3580

Ile Leu His Glu Ala Gly Lys Pro Gln Lys Ile Thr Glu Gly Glu Lys
3585                3590                3595                3600

Met Lys Val Ala Tyr Arg Phe Glu Asp Ile Glu Phe Cys Ser His Thr
           3605                3610                3615

Pro Val Pro Val Arg Trp Ser Asp Asn Thr Ser Ser His Met Ala Gly
      3620                3625                3630

Arg Asp Thr Ala Val Ile Leu Ser Lys Met Ala Thr Arg Leu Asp Ser
      3635                3640                3645

Ser Gly Glu Arg Gly Thr Thr Ala Tyr Glu Lys Ala Val Ala Phe Ser
   3650                3655                3660

Phe Leu Leu Met Tyr Ser Trp Asn Pro Leu Val Arg Arg Ile Cys Leu
3665                3670                3675                3680
```

```
Leu Val Leu Ser Gln Gln Pro Glu Thr Asp Pro Ser Lys His Ala Thr
        3685                3690                3695
Tyr Tyr Tyr Lys Gly Asp Pro Ile Gly Ala Tyr Lys Asp Val Ile Gly
        3700                3705                3710
Arg Asn Leu Ser Glu Leu Lys Arg Thr Gly Phe Glu Lys Leu Ala Asn
        3715                3720                3725
Leu Asn Leu Ser Leu Ser Thr Leu Gly Ile Trp Thr Lys His Thr Ser
        3730                3735                3740
Lys Arg Ile Ile Gln Asp Cys Val Ala Ile Gly Lys Glu Glu Gly Asn
3745                3750                3755                3760
Trp Leu Val Asn Ala Asp Arg Leu Ile Ser Ser Lys Thr Gly His Leu
        3765                3770                3775
Tyr Ile Pro Asp Lys Gly Phe Thr Leu Gln Gly Lys His Tyr Glu Gln
        3780                3785                3790
Leu Gln Leu Arg Thr Glu Thr Asn Pro Val Met Gly Val Gly Thr Glu
        3795                3800                3805
Arg Tyr Lys Leu Gly Pro Ile Val Asn Leu Leu Leu Arg Arg Leu Lys
        3810                3815                3820
Ile Leu Leu Met Thr Ala Val Gly Val Ser Ser
3825                3830                3835

<210> SEQ ID NO 3
<211> LENGTH: 9711
<212> TYPE: DNA
<213> ORGANISM: Hepatitis C virus

<400> SEQUENCE: 3
```

| | | | |
|---|---|---|---|
| acccgcccct | aatagggggcg | acactccgcc atgaatcact | ccctgtgag gaactactgt | 60 |
| cttcacgcag | aaagcgtcta | gccatggcgt tagtatgagt | gtcgtacagc ctccaggccc | 120 |
| cccctcccg | ggagagccat | agtggtctgc ggaaccggtg | agtacaccgg aattgccggg | 180 |
| aagactgggt | cctttcttgg | ataaacccac tctatgcccg | gccatttggg cgtgcccccg | 240 |
| caagactgct | agccgagtag | cgttgggttg cgaaaggcct | tgtggtactg cctgataggg | 300 |
| tgcttgcgag | tgccccggga | ggtctcgtag accgtgcacc | atgagcacaa atcctaaacc | 360 |
| tcaaagaaaa | accaaaagaa | acaccaaccg tcgcccacaa | gacgttaagt ttccgggcgg | 420 |
| cggccagatc | gttggcggag | tatacttgtt gccgcgcagg | ggccccaggt tgggtgtgcg | 480 |
| cgcgacaagg | aagacttcgg | agcggtccca gccacgtgga | aggcgccagc ccatccctaa | 540 |
| agatcggcgc | tccactggca | aatcctgggg aaaaccagga | taccctggc ccctatacgg | 600 |
| gaatgaggga | ctcggctggg | caggatggct cctgtccccc | cgaggttccc gtccctcttg | 660 |
| gggccccaat | gaccccggc | ataggtcgcg caacgtgggt | aaggtcatcg ataccctaac | 720 |
| gtgcggcttt | gccgacctca | tggggtacat ccctgtcgtg gcgcccccgc | tcggcggcgt | 780 |
| cgccagagct | ctcgcgcatg | gcgtgagagt cctggaggac ggggttaatt | ttgcaacagg | 840 |
| gaacttaccc | ggttgctcct | tttctatctt cttgctggcc ctgctgtcct | gcatcaccac | 900 |
| cccggtctcc | gctgccgaag | tgaagaacat cagtaccggc tacatggtga | ctaacgactg | 960 |
| caccaatgac | agcattacct | ggcagctcca ggctgctgtc ctccacgtcc | ccgggtgcgt | 1020 |
| cccgtgcgag | aaagtgggga | atgcatctca gtgctggata ccggtctcac | cgaatgtggc | 1080 |
| cgtgcagcgg | cccggcgccc | tcacgcaggg cttgcgacg cacatcgaca | tggttgtgat | 1140 |
| gtccgccacg | ctctgctctg | ccctctacgt ggggacctc tgcggtgggg | tgatgctcgc | 1200 |

```
agcccaaatg ttcattgtct cgccgcagca ccactggttt gtccaagact gcaattgctc    1260
catctaccct ggtaccatca ctggacaccg catggcatgg acatgatga tgaactggtc     1320 gcccacggct accatgatct tggcgtacgc gatgcgtgtc cccgaggtca ttatagacat    1380
cattagcggg gctcattggg gcgtcatgtt cggcttggcc tacttctcta tgcagggagc    1440
gtgggcgaaa gtcgttgtca tccttctgtt ggccgccggg gtggacgcgc gcacccatac    1500
tgttgggggt tctgccgcgc agaccaccgg gcgcctcacc agcttatttg acatgggccc    1560
caggcagaaa atccagctcg ttaacaccaa tggcagctgg cacatcaacc gcaccgccct    1620
gaactgcaat gactccttgc acaccggctt tatcgcgtct ctgttctaca cccacagctt    1680
caactcgtca ggatgtcccg aacgcatgtc cgcctgccgc agtatcgagg ccttccgggt    1740
gggatggggc gccttgcaat atgaggataa tgtcaccaat ccagaggata tgagaccctta    1800 ttgctggcac tacccaccaa ggcagtgtgg cgtggtctcc gcgaagactg tgtgtggccc    1860
agtgtactgt ttcacccca gcccagtggt agtgggcacg accgacaggc ttggagcgcc     1920
cacttacacg tggggggaga atgagacaga tgtcttccta ttgaacagca ctcgaccacc    1980
gctgggtcta tggttcggct gcacgtggat gaactcttct ggctacacca agacttgcgg    2040
cgcaccaccc tgccgtacta gagctgactt caacgccagc acggacctgt tgtgcccaac    2100
ggactgtttt aggaagcatc ctgataccac ttacctcaaa tgcggctctg ggccctggct    2160
cacgccaagg tgcctgatcg actacccta caggctctgg cattacccct gcacagttaa     2220
ctataccatc ttcaaaataa ggatgtatgt gggagggggtt gagcacaggc tcacggctgc    2280
atgcaatttc actcgtgggg atcgttgcaa cttggaggac agagacagaa gtcaactgtc    2340
tcctttgttg cactccacca cggaatgggc cattttacct tgctcttact cggacctgcc    2400
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcggacgcca gggtttgcgc ctgcttatgg atgctcatct tgttgggcca    2580
ggccgaagca gcactagaga agctggtcat cttgcacgct gcgagcgcag ctagctgcaa    2640
tggcttccta tattttgtca tcttttttcgt ggctgcttgg tacatcaagg gtcgggtagt    2700 cccccttagct acctattccc tcactggcct gtggtccttt agcctactgc tcctagcatt    2760
gccccaacag gcttatgctt atgacgcatc tgtgcatggc cagataggag cggctctgct    2820
ggtaatgatc actctctta ctctcacccc cgggtataag acccttctca gccggttttt      2880
gtggtggttg tgctatcttc tgaccctggg ggaagctatg gtccaggagt gggcaccacc    2940
tatgcaggtg cgcggtggcc gtgatggcat catatgggcc gtcgccatat tctacccagg    3000
tgtggtgttt gacataacca agtggctctt ggcggtgctt gggcctgctt acctcctaaa    3060
aggtgctttg acgcgcgtgc cgtacttcgt cagggctcac gctctactga ggatgtgcac    3120
catggcaagg catctcgcgg ggggcaggta cgtccagatg gcgctactag cccttggcag    3180
gtggactggc acttacatct atgaccacct caccctatg tcggattggg ctgctagtgg    3240
cctgcgggac ctggcggtcg ccgttgagcc tatcatcttc agtccgatgg agaagaaagt    3300
cattgtctgg ggagcggaga cagctgcttg tggggacatt ttacacggac ttcccgtgtc    3360
cgcccgactt ggtcgggagg tcctccttgg cccagctgat ggctatacct caagggggtg    3420
gagtcttctc gccccccatca ctgcttacgc ccagcagaca cgtggccttt tgggcaccat    3480
agtggtgagc atgacggggc gcgacaagac agaacaggct ggggaaattc aggtcctgtc    3540
cacagtcact cagtccttcc tcggaacatc catctcgggg gttttgtgga ctgtctacca    3600
```

```
tggagctggc aacaagactc tggccggctc acggggtccg gtcacgcaga tgtactccag    3660
tgctgagggg gacttagtag ggtggcccag ccccctggg actaaatctt tggagccgtg    3720
cacgtgtgga gcggtcgacc tgtacctggt cacgcggaac gctgatgtca tcccggctcg    3780
aagacgcggg gacaaacggg gagcgctact ctccccgaga cctctttcca ccttgaaggg    3840
gtcctcagga ggcccggtgc tatgcccag gggccacgct gtcggagtct tccgggcagc    3900
tgtgtgctct cggggcgtgg ctaagtccat agatttcatc cccgttgaga cactcgacat    3960
cgtcacgcgg tcccccacct ttagtgacaa cagcacacca cctgctgtgc cccagaccta    4020
tcaggtcggg tacttgcatg ccccgactgg cagtggaaag agcaccaaag ttcctgtcgc    4080
atatgctgct cagggtata aagtgctagt gcttaatccc tcagtggctg ccaccctggg    4140
gtttggggcg tacttgtcta aggcacatgg catcaatccc aacattagga ctggagtcag    4200
gactgtgacg accggggcgc ccatcacgta ctccacatat ggcaaattcc tcgccgatgg    4260
gggctgtgcg ggcggcgcct acgacatcat catatgtgat gaatgccatg ccgtggactc    4320
taccaccatc cttggcatcg gaacagtcct tgatcaagca gagacagctg ggtcagact    4380 aactgtgctg gctacagcta cgccccctgg gtcagtgaca accccccacc ccaacataga    4440
ggaggtggcc cttgggcagg agggcgagat ccccttctat gggagggcga ttccctgtc    4500 ttacatcaag ggaggaagac atctgatctt ctgccattca aagaaaaagt gtgacgagct    4560
cgcggcggcc cttcgggta tgggcttgaa ctcagtggca tactacagag ggttggacgt    4620
ctccgtaata ccaactcagg gagacgtagt ggtcgtcgcc accgacgccc tcatgacagg    4680
gtatactggg gactttgact ccgtgatcga ctgcaacgta gcggtcactc aagttgtaga    4740
cttcagttta gaccccacat tcaccataac cacacagatt gtccctcaag acgctgtctc    4800
acgtagccag cgccggggtc gcacgggtag gggaagactg ggcatttata ggtatgtttc    4860
cactggtgag cgagcctcag gaatgtttga cagtgtagtg ctctgtgagt gctacgacgc    4920 agggggccgca tggtatgagc tcacaccatc ggagaccacc gtcaggctca gggcgtattt    4980
caacacgccc ggtttgcctg tgtgccaaga ccatcttgag ttttgggagg cagttttcac    5040
cggcctcaca cacatagatg cccacttcct ttcccaaaca aagcaatcgg gggaaaattt    5100
cgcatactta acagcctacc aggctacagt gtgcgctagg gccaaagccc ccccccgtc    5160 ctgggacgtc atgtggaagt gtttgactcg actcaagccc acactcgtgg gccccacacc    5220
tctcctgtac cgcttgggct ctgttaccaa cgaggtcacc ctcacacatc ccgtgacgaa    5280
atacatcgcc acctgcatgc aagccgacct tgaggtcatg accagcacat gggtcttggc    5340
agggggagtc ttgcgccg tcgccgcgta ttgcctggcg accgggtgtg tttgcatcat    5400
cggccgcttg cacattaacc agcgagccgt cgttgcgccg gacaaggagg tcctctatga    5460
ggcttttgat gagatggagg aatgtgcctc tagggcggct ctcattgaag aggggcagcg    5520
gatagccgag atgctgaagt ccaagatcca aggcttattg cagcaagctt ccaaacaagc    5580
tcaagacata caacccactg tgcaggcttc atgcccaag gtagaacaat ctgggccaa    5640 acacatgtgg aacttcatta gcggcatcca ataccctcgca ggactatcaa cactgccagg    5700
gaaccctgca gtagcttcca tgatggcgtt cagtgccgcc ctcaccagtc cgctgtcaac    5760
aagcaccact atccttctca acatttttggg gggctggcta gcatcccaaa ttgcaccacc    5820
cgcgggggcc actggcttcg ttgtcagtgg cctagtggga ctgccgtag gcagtatagg    5880 cttaggtaag gtgctagtgg acatcctggc agggtatggt gcgggcattt cgggggctct    5940
```

```
cgtcgcattc aagatcatgt ctggcgagaa gccctccatg gaggatgtcg tcaacttgct    6000
gcctggaatt ctgtctccgg gtgccttggt agtgggagtc atctgcgcgg ccattctgcg    6060
ccgacacgtg ggaccggggg aaggcgccgt ccaatggatg aatagactca ttgcctttgc    6120
ttccagagga aatcacgtcg cccccaccca ctacgtgacg gagtcggatg cgtcgcagcg    6180
tgtgacccaa ctacttggct cccttaccat aaccagcctg ctcagaagac tccacaactg    6240
gattactgag gactgcccca tcccatgcgg cggctcgtgg ctccgcgatg tgtgggactg    6300
ggtttgcacc atcctaacag actttaaaaa ttggctgacc tccaaattat tcccaaagat    6360 gccccggcctc ccctttgtct cctgtcaaaa ggggtacaag ggcgtgtggg ccggcactgg    6420
catcatgacc acacggtgtc cttgcggcgc caatatctct ggcaatgtcc gcttgggctc    6480
catgagaatc acgggcccta agacctgcat gaatatctgg caggggacct ttcctatcaa    6540
ttgttacacg gagggccagt gcgtgccgaa acccgcgcca aactttaagg tcgccatctg    6600
gagggtggcg gcctcagagt acgcggaggt gacgcagcac gggtcatacc actacataac    6660
aggactcacc actgataact tgaaagtccc ctgccaacta ccctctcccg agttcttttc    6720
ctgggtggac ggagtgcaga tccataggtt tgccccccaca ccgaagccgt ttttccggga    6780
tgaggtctcg ttctgcgttg ggcttaattc atttgtcgtc gggtcccagc ttccttgcga    6840
ccctgaaccc gacacagacg tattgatgtc catgctaaca gatccatctc atatcacggc    6900
ggagactgca gcgcggcgtt tagcgcgggg gtcacccccca tccgaggcaa gctcctcggc    6960
gagccagcta tcggcaccat cgctgcgagc cacctgcacc acccacgcca aagcctatga    7020
tgtggacatg gtggatgcta acctgttcat gggggggcgat gtgactcgga tagagtctgg    7080
gtccaaagtg gtcgttctgg actctctcga cccaatggtc gaagaaagga gcgaccttga    7140
gccttcgata ccatcagaat acatgctccc caagaagagg ttcccaccag ctttaccggc    7200
ctgggcacgg cctgattaca acccaccgct tgtggaatcg tggaaaaggc cagattacca    7260
accggccact gttgcgggct gtgctctccc tcctcctagg aaaacccga cgcctccccc    7320 aaggaggcgc cggacagtgg gcctaagtga ggactccata ggagatgccc ttcaacagct    7380
ggccattaag tccttttggcc agccccccccc aagcggcgat tcaggccttt ccacgggggc    7440
gggcgctgcc gattccggca gtcagacgcc tcctgatgag ttggccccttt cggagacagg    7500 ttccatctct tccatgcccc ccctcgaggg ggagcttgga gatccagacc tggagcctga    7560
gcaggtagag ccccaacccc ccccccaggg ggggtggca gctccggcct cggactcggg    7620
gtcctggtct acttgctccg aggaggacga ctccgtcgtg tgctgctcca tgtcatactc    7680
ctggaccggg gctctaataa ctccttgtag tcccgaagag gagaagttac cgattaaccc    7740
cttgagcaac tccctgttgc gatatcacaa caaggtgtac tgtaccacaa caaagagcgc    7800
ctcactaagg gctaaaaagg taactttgga taggatgcaa gtgctcgact cctactacga    7860
ctcagtctta aaggacatta agctagcgcc ctccaaggtc accgcaaggc tcctcaccat    7920
ggaggaggct tgccagttaa ccccaccccca ttctgcaaga tctaaatatg ggttttgggggc    7980 taaggaggtc cgcagcttgt ccgggagggc cgttaaccac atcaagtccg tgtgaagga    8040 cctcctggag gactcagaaa caccaattcc cacaaccatt atggccaaaa atgaggtgtt    8100
ctgcgtggac cccaccaagg ggggcaagaa agcagctcgc cttatcgttt accctgacct    8160
cggcgtcagg gtctgcgaga agatggccct ttatgacatt acacaaaaac ttcctcaggc    8220
ggtgatgggg gcttccttatg gattccagta ttcccccgct cagcgggtag agtttctctt    8280
gaaagcatgg gcggaaaaga aggaccctat gggtttttcg tatgataccc gatgctttga    8340
```

-continued

```
ctcaaccgtc actgagagag acatcaggac tgaggagtcc atatatcggg cctgctcctt    8400
gcccgaggag gcccacactg ccatacactc gctaactgag agactttacg tgggagggcc    8460
tatgttcaac agcaagggcc aaacctgcgg gtacaggcgt tgccgcgcca gcggggtgct    8520
caccactagc atggggaaca ccatcacatg ctacgtgaaa gccttagcgg cttgtaaagc    8580
tgcagggata tcgcgccca caatgctggt atgcggcgat gacttggttg tcatctcaga    8640
aagccagggg accgaggagg acgagcggaa cctgagagcc ttcacggagg ctatgaccag    8700
gtattctgcc cctcctggtg accccccag accggagtat gatctggagc tgataacatc    8760
ttgctcctca aatgtgtctg tggcgctggg cccacaaggc cgccgcagat actacctgac    8820
cagagaccct accactccaa tcgcccgggc tgcctgggaa acagttagac actcccctgt    8880
caattcatgg ctgggaaaca tcatccagta cgccccgacc atatgggctc gcatggtcct    8940
gatgacacac ttcttctcca ttctcatggc tcaagacacg ctggaccaga acctcaactt    9000
tgagatgtac ggagcggtgt actccgtgag tcccttggac ctcccagcta taattgaaag    9060
gttacatggg cttgacgctt tttctctgca cacatacact ccccacgaac tgacacgggt    9120
ggcttcagcc ctcagaaaac ttggggcgcc accctcaga gcgtggaaga gccgggcacg    9180
tgcagtcagg gcgtccctca tctcccgtgg ggggagagcg gccgtttgcg gtcgatatct    9240
cttcaattgg gcggtgaaga ccaagctcaa actcactcca ttgccggaag cgcgcctcct    9300
ggatttatcc agctggttca ccgtcggcgc cggcggggc gacatttatc acagcgtgtc    9360
gcgtgcccga ccccgcttat tgctctttgg cctactccta cttttgtag gggtaggcct    9420 tttcctactc cccgctcggt agagcggcac acattagcta cactccatag ctaactgtcc    9480
cttttttttt tttttttttt tttttttttt tttttttttt tttttttttt tttttttttt    9540
tttttttttt tttttttttt tttttctttt tttctctttt ccttctttct taccttattt    9600
tactttcttt cctggtggct ccatcttagc cctagtcacg gctagctgtg aaaggtccgt    9660
gagccgcatg actgcagaga gtgccgtaac tggtctctct gcagatcatg t              9711
```

<210> SEQ ID NO 4
<211> LENGTH: 3033
<212> TYPE: PRT
<213> ORGANISM: Hepatitis C virus

<400> SEQUENCE: 4

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
            100                 105                 110

Arg His Arg Ser Arg Asn Val Gly Lys Val Ile Asp Thr Leu Thr Cys
        115                 120                 125
```

```
Gly Phe Ala Asp Leu Met Gly Tyr Ile Pro Val Val Gly Ala Pro Leu
        130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
                195                 200                 205

Asn Asp Ser Ile Thr Trp Gln Leu Gln Ala Ala Val Leu His Val Pro
210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
                260                 265                 270

Ser Ala Leu Tyr Val Gly Asp Leu Cys Gly Gly Val Met Leu Ala Ala
                275                 280                 285

Gln Met Phe Ile Val Ser Pro Gln His His Trp Phe Val Gln Asp Cys
290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335

Ala Met Arg Val Pro Glu Val Ile Ile Asp Ile Ile Ser Gly Ala His
                340                 345                 350

Trp Gly Val Met Phe Gly Leu Ala Tyr Phe Ser Met Gln Gly Ala Trp
                355                 360                 365

Ala Lys Val Val Val Ile Leu Leu Leu Ala Ala Gly Val Asp Ala Arg
370                 375                 380

Thr His Thr Val Gly Gly Ser Ala Ala Gln Thr Thr Gly Arg Leu Thr
385                 390                 395                 400

Ser Leu Phe Asp Met Gly Pro Arg Gln Lys Ile Gln Leu Val Asn Thr
                405                 410                 415

Asn Gly Ser Trp His Ile Asn Arg Thr Ala Leu Asn Cys Asn Asp Ser
                420                 425                 430

Leu His Thr Gly Phe Ile Ala Ser Leu Phe Tyr Thr His Ser Phe Asn
                435                 440                 445

Ser Ser Gly Cys Pro Glu Arg Met Ser Ala Cys Arg Ser Ile Glu Ala
450                 455                 460

Phe Arg Val Gly Trp Gly Ala Leu Gln Tyr Glu Asp Asn Val Thr Asn
465                 470                 475                 480

Pro Glu Asp Met Arg Pro Tyr Cys Trp His Tyr Pro Pro Arg Gln Cys
                485                 490                 495

Gly Val Val Ser Ala Lys Thr Val Cys Gly Pro Val Tyr Cys Phe Thr
                500                 505                 510

Pro Ser Pro Val Val Val Gly Thr Thr Asp Arg Leu Gly Ala Pro Thr
                515                 520                 525

Tyr Thr Trp Gly Glu Asn Glu Thr Asp Val Phe Leu Leu Asn Ser Thr
                530                 535                 540

Arg Pro Pro Leu Gly Ser Trp Phe Gly Cys Thr Trp Met Asn Ser Ser
```

```
                545                 550                 555                 560
Gly Tyr Thr Lys Thr Cys Gly Ala Pro Pro Cys Arg Thr Arg Ala Asp
                565                 570                 575
Phe Asn Ala Ser Thr Asp Leu Leu Cys Pro Thr Asp Cys Phe Arg Lys
                580                 585                 590
His Pro Asp Thr Thr Tyr Leu Lys Cys Gly Ser Gly Pro Trp Leu Thr
                595                 600                 605
Pro Arg Cys Leu Ile Asp Tyr Pro Tyr Arg Leu Trp His Tyr Pro Cys
                610                 615                 620
Thr Val Asn Tyr Thr Ile Phe Lys Ile Arg Met Tyr Val Gly Gly Val
625                             630                 635                 640
Glu His Arg Leu Thr Ala Ala Cys Asn Phe Thr Arg Gly Asp Arg Cys
                645                 650                 655
Asn Leu Glu Asp Arg Asp Arg Ser Gln Leu Ser Pro Leu Leu His Ser
                660                 665                 670
Thr Thr Glu Trp Ala Ile Leu Pro Cys Ser Tyr Ser Asp Leu Pro Ala
                675                 680                 685
Leu Ser Thr Gly Leu Leu His Leu His Gln Asn Ile Val Asp Val Gln
                690                 695                 700
Phe Met Tyr Gly Leu Ser Pro Ala Leu Thr Lys Tyr Ile Val Arg Trp
705                             710                 715                 720
Glu Trp Val Ile Leu Leu Phe Leu Leu Leu Ala Asp Ala Arg Val Cys
                725                 730                 735
Ala Cys Leu Trp Met Leu Ile Leu Leu Gly Gln Ala Glu Ala Ala Leu
                740                 745                 750
Glu Lys Leu Val Ile Leu His Ala Ala Ser Ala Ala Ser Cys Asn Gly
                755                 760                 765
Phe Leu Tyr Phe Val Ile Phe Phe Val Ala Ala Trp Tyr Ile Lys Gly
                770                 775                 780
Arg Val Val Pro Leu Ala Thr Tyr Ser Leu Thr Gly Leu Trp Ser Phe
785                             790                 795                 800
Ser Leu Leu Leu Leu Ala Leu Pro Gln Gln Ala Tyr Ala Tyr Asp Ala
                805                 810                 815
Ser Val His Gly Gln Ile Gly Ala Ala Leu Leu Val Met Ile Thr Leu
                820                 825                 830
Phe Thr Leu Thr Pro Gly Tyr Lys Thr Leu Leu Ser Arg Phe Leu Trp
                835                 840                 845
Trp Leu Cys Tyr Leu Leu Thr Leu Gly Glu Ala Met Val Gln Glu Trp
                850                 855                 860
Ala Pro Pro Met Gln Val Arg Gly Gly Arg Asp Gly Ile Ile Trp Ala
865                             870                 875                 880
Val Ala Ile Phe Tyr Pro Gly Val Val Phe Asp Ile Thr Lys Trp Leu
                885                 890                 895
Leu Ala Val Leu Gly Pro Ala Tyr Leu Leu Lys Gly Ala Leu Thr Arg
                900                 905                 910
Val Pro Tyr Phe Val Arg Ala His Ala Leu Leu Arg Met Cys Thr Met
                915                 920                 925
Ala Arg His Leu Ala Gly Gly Arg Tyr Val Gln Met Ala Leu Leu Ala
                930                 935                 940
Leu Gly Arg Trp Thr Gly Thr Tyr Ile Tyr Asp His Leu Thr Pro Met
945                             950                 955                 960
Ser Asp Trp Ala Ala Ser Gly Leu Arg Asp Leu Ala Val Ala Val Glu
                965                 970                 975
```

```
Pro Ile Ile Phe Ser Pro Met Glu Lys Lys Val Ile Val Trp Gly Ala
            980                 985                 990

Glu Thr Ala Ala Cys Gly Asp Ile Leu His Gly Leu Pro Val Ser Ala
        995                1000                1005

Arg Leu Gly Arg Glu Val Leu Leu Gly Pro Ala Asp Gly Tyr Thr Ser
    1010                1015                1020

Lys Gly Trp Ser Leu Leu Ala Pro Ile Thr Ala Tyr Ala Gln Gln Thr
1025                1030                1035                1040

Arg Gly Leu Leu Gly Thr Ile Val Val Ser Met Thr Gly Arg Asp Lys
        1045                1050                1055

Thr Glu Gln Ala Gly Glu Ile Gln Val Leu Ser Thr Val Thr Gln Ser
            1060                1065                1070

Phe Leu Gly Thr Ser Ile Ser Gly Val Leu Trp Thr Val Tyr His Gly
        1075                1080                1085

Ala Gly Asn Lys Thr Leu Ala Gly Ser Arg Gly Pro Val Thr Gln Met
    1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Thr Cys Gly Ala Val Asp Leu Tyr Leu
        1125                1130                1135

Val Thr Arg Asn Ala Asp Val Ile Pro Ala Arg Arg Arg Gly Asp Lys
        1140                1145                1150

Arg Gly Ala Leu Leu Ser Pro Arg Pro Leu Ser Thr Leu Lys Gly Ser
    1155                1160                1165

Ser Gly Gly Pro Val Leu Cys Pro Arg Gly His Ala Val Gly Val Phe
1170                1175                1180

Arg Ala Ala Val Cys Ser Arg Gly Val Ala Lys Ser Ile Asp Phe Ile
1185                1190                1195                1200

Pro Val Glu Thr Leu Asp Ile Val Thr Arg Ser Pro Thr Phe Ser Asp
            1205                1210                1215

Asn Ser Thr Pro Pro Ala Val Pro Gln Thr Tyr Gln Val Gly Tyr Leu
    1220                1225                1230

His Ala Pro Thr Gly Ser Gly Lys Ser Thr Lys Val Pro Val Ala Tyr
        1235                1240                1245

Ala Ala Gln Gly Tyr Lys Val Leu Val Leu Asn Pro Ser Val Ala Ala
    1250                1255                1260

Thr Leu Gly Phe Gly Ala Tyr Leu Ser Lys Ala His Gly Ile Asn Pro
1265                1270                1275                1280

Asn Ile Arg Thr Gly Val Arg Thr Val Thr Thr Gly Ala Pro Ile Thr
        1285                1290                1295

Tyr Ser Thr Tyr Gly Lys Phe Leu Ala Asp Gly Gly Cys Ala Gly Gly
        1300                1305                1310

Ala Tyr Asp Ile Ile Ile Cys Asp Glu Cys His Ala Val Asp Ser Thr
    1315                1320                1325

Thr Ile Leu Gly Ile Gly Thr Val Leu Asp Gln Ala Glu Thr Ala Gly
    1330                1335                1340

Val Arg Leu Thr Val Leu Ala Thr Ala Thr Pro Pro Gly Ser Val Thr
1345                1350                1355                1360

Thr Pro His Pro Asn Ile Glu Glu Val Ala Leu Gly Gln Glu Gly Glu
            1365                1370                1375

Ile Pro Phe Tyr Gly Arg Ala Ile Pro Leu Ser Tyr Ile Lys Gly Gly
            1380                1385                1390
```

```
Arg His Leu Ile Phe Cys His Ser Lys Lys Cys Asp Glu Leu Ala
    1395                1400                1405

Ala Ala Leu Arg Gly Met Gly Leu Asn Ser Val Ala Tyr Tyr Arg Gly
1410                1415                1420

Leu Asp Val Ser Val Ile Pro Thr Gln Gly Asp Val Val Val Ala
1425                1430                1435                1440

Thr Asp Ala Leu Met Thr Gly Tyr Thr Gly Asp Phe Asp Ser Val Ile
            1445                1450                1455

Asp Cys Asn Val Ala Val Thr Gln Val Val Asp Phe Ser Leu Asp Pro
        1460                1465                1470

Thr Phe Thr Ile Thr Thr Gln Ile Val Pro Gln Asp Ala Val Ser Arg
    1475                1480                1485

Ser Gln Arg Arg Gly Arg Thr Gly Arg Gly Arg Leu Gly Ile Tyr Arg
    1490                1495                1500

Tyr Val Ser Thr Gly Glu Arg Ala Ser Gly Met Phe Asp Ser Val Val
1505                1510                1515                1520

Leu Cys Glu Cys Tyr Asp Ala Gly Ala Ala Trp Tyr Glu Leu Thr Pro
            1525                1530                1535

Ser Glu Thr Thr Val Arg Leu Arg Ala Tyr Phe Asn Thr Pro Gly Leu
        1540                1545                1550

Pro Val Cys Gln Asp His Leu Glu Phe Trp Glu Ala Val Phe Thr Gly
    1555                1560                1565

Leu Thr His Ile Asp Ala His Phe Leu Ser Gln Thr Lys Gln Ser Gly
    1570                1575                1580

Glu Asn Phe Ala Tyr Leu Thr Ala Tyr Gln Ala Thr Val Cys Ala Arg
1585                1590                1595                1600

Ala Lys Ala Pro Pro Pro Ser Trp Asp Val Met Trp Lys Cys Leu Thr
            1605                1610                1615

Arg Leu Lys Pro Thr Leu Val Gly Pro Thr Pro Leu Leu Tyr Arg Leu
        1620                1625                1630

Gly Ser Val Thr Asn Glu Val Thr Leu Thr His Pro Val Thr Lys Tyr
    1635                1640                1645

Ile Ala Thr Cys Met Gln Ala Asp Leu Glu Val Met Thr Ser Thr Trp
    1650                1655                1660

Val Leu Ala Gly Gly Val Leu Ala Ala Val Ala Ala Tyr Cys Leu Ala
1665                1670                1675                1680

Thr Gly Cys Val Cys Ile Ile Gly Arg Leu His Ile Asn Gln Arg Ala
            1685                1690                1695

Val Val Ala Pro Asp Lys Glu Val Leu Tyr Glu Ala Phe Asp Glu Met
        1700                1705                1710

Glu Glu Cys Ala Ser Arg Ala Ala Leu Ile Glu Glu Gly Gln Arg Ile
    1715                1720                1725

Ala Glu Met Leu Lys Ser Lys Ile Gln Gly Leu Leu Gln Gln Ala Ser
    1730                1735                1740

Lys Gln Ala Gln Asp Ile Gln Pro Thr Val Gln Ala Ser Trp Pro Lys
1745                1750                1755                1760

Val Glu Gln Phe Trp Ala Lys His Met Trp Asn Phe Ile Ser Gly Ile
            1765                1770                1775

Gln Tyr Leu Ala Gly Leu Ser Thr Leu Pro Gly Asn Pro Ala Val Ala
        1780                1785                1790

Ser Met Met Ala Phe Ser Ala Ala Leu Thr Ser Pro Leu Ser Thr Ser
    1795                1800                1805

Thr Thr Ile Leu Leu Asn Ile Leu Gly Gly Trp Leu Ala Ser Gln Ile
```

-continued

```
                1810                1815                1820
Ala Pro Pro Ala Gly Ala Thr Gly Phe Val Val Ser Gly Leu Val Gly
            1825                1830                1835                1840
Ala Ala Val Gly Ser Ile Gly Leu Gly Lys Val Leu Val Asp Ile Leu
            1845                1850                1855
Ala Gly Tyr Gly Ala Gly Ile Ser Gly Ala Leu Val Ala Phe Lys Ile
            1860                1865                1870
Met Ser Gly Glu Lys Pro Ser Met Glu Asp Val Val Asn Leu Leu Pro
            1875                1880                1885
Gly Ile Leu Ser Pro Gly Ala Leu Val Val Gly Val Ile Cys Ala Ala
            1890                1895                1900
Ile Leu Arg Arg His Val Gly Pro Gly Glu Gly Ala Val Gln Trp Met
            1905                1910                1915                1920
Asn Arg Leu Ile Ala Phe Ala Ser Arg Gly Asn His Val Ala Pro Thr
            1925                1930                1935
His Tyr Val Thr Glu Ser Asp Ala Ser Gln Arg Val Thr Gln Leu Leu
            1940                1945                1950
Gly Ser Leu Thr Ile Thr Ser Leu Leu Arg Arg Leu His Asn Trp Ile
            1955                1960                1965
Thr Glu Asp Cys Pro Ile Pro Cys Gly Gly Ser Trp Leu Arg Asp Val
            1970                1975                1980
Trp Asp Trp Val Cys Thr Ile Leu Thr Asp Phe Lys Asn Trp Leu Thr
1985                1990                1995                2000
Ser Lys Leu Phe Pro Lys Met Pro Gly Leu Pro Phe Val Ser Cys Gln
            2005                2010                2015
Lys Gly Tyr Lys Gly Val Trp Ala Gly Thr Gly Ile Met Thr Thr Arg
            2020                2025                2030
Cys Pro Cys Gly Ala Asn Ile Ser Gly Asn Val Arg Leu Gly Ser Met
            2035                2040                2045
Arg Ile Thr Gly Pro Lys Thr Cys Met Asn Ile Trp Gln Gly Thr Phe
            2050                2055                2060
Pro Ile Asn Cys Tyr Thr Glu Gly Gln Cys Val Pro Lys Pro Ala Pro
2065                2070                2075                2080
Asn Phe Lys Val Ala Ile Trp Arg Val Ala Ala Ser Glu Tyr Ala Glu
            2085                2090                2095
Val Thr Gln His Gly Ser Tyr His Tyr Ile Thr Gly Leu Thr Thr Asp
            2100                2105                2110
Asn Leu Lys Val Pro Cys Gln Leu Pro Ser Pro Glu Phe Phe Ser Trp
            2115                2120                2125
Val Asp Gly Val Gln Ile His Arg Phe Ala Pro Thr Pro Lys Pro Phe
            2130                2135                2140
Phe Arg Asp Glu Val Ser Phe Cys Val Gly Leu Asn Ser Phe Val Val
2145                2150                2155                2160
Gly Ser Gln Leu Pro Cys Asp Pro Glu Pro Asp Thr Asp Val Leu Met
            2165                2170                2175
Ser Met Leu Thr Asp Pro Ser His Ile Thr Ala Glu Thr Ala Ala Arg
            2180                2185                2190
Arg Leu Ala Arg Gly Ser Pro Pro Ser Glu Ala Ser Ser Ser Ala Ser
            2195                2200                2205
Gln Leu Ser Ala Pro Ser Leu Arg Ala Thr Cys Thr Thr His Gly Lys
            2210                2215                2220
Ala Tyr Asp Val Asp Met Val Asp Ala Asn Leu Phe Met Gly Gly Asp
2225                2230                2235                2240
```

```
Val Thr Arg Ile Glu Ser Gly Ser Lys Val Val Leu Asp Ser Leu
            2245                2250                2255

Asp Pro Met Val Glu Glu Arg Ser Asp Leu Glu Pro Ser Ile Pro Ser
            2260                2265                2270

Glu Tyr Met Leu Pro Lys Lys Arg Phe Pro Ala Leu Pro Ala Trp
            2275                2280                2285

Ala Arg Pro Asp Tyr Asn Pro Pro Leu Val Glu Ser Trp Lys Arg Pro
2290                2295                2300

Asp Tyr Gln Pro Ala Thr Val Ala Gly Cys Ala Leu Pro Pro Arg
2305                2310                2315                2320

Lys Thr Pro Thr Pro Pro Pro Arg Arg Arg Arg Thr Val Gly Leu Ser
            2325                2330                2335

Glu Asp Ser Ile Gly Asp Ala Leu Gln Gln Leu Ala Ile Lys Ser Phe
            2340                2345                2350

Gly Gln Pro Pro Pro Ser Gly Asp Ser Gly Leu Ser Thr Gly Ala Gly
            2355                2360                2365

Ala Ala Asp Ser Gly Ser Gln Thr Pro Pro Asp Glu Leu Ala Leu Ser
    2370                2375                2380

Glu Thr Gly Ser Ile Ser Ser Met Pro Pro Leu Glu Gly Glu Leu Gly
2385                2390                2395                2400

Asp Pro Asp Leu Glu Pro Glu Gln Val Glu Pro Gln Pro Pro Gln
            2405                2410                2415

Gly Gly Val Ala Ala Pro Gly Ser Asp Ser Gly Ser Trp Ser Thr Cys
            2420                2425                2430

Ser Glu Glu Asp Asp Ser Val Val Cys Cys Ser Met Ser Tyr Ser Trp
            2435                2440                2445

Thr Gly Ala Leu Ile Thr Pro Cys Ser Pro Glu Glu Glu Lys Leu Pro
    2450                2455                2460

Ile Asn Pro Leu Ser Asn Ser Leu Leu Arg Tyr His Asn Lys Val Tyr
2465                2470                2475                2480

Cys Thr Thr Thr Lys Ser Ala Ser Leu Arg Ala Lys Lys Val Thr Phe
            2485                2490                2495

Asp Arg Met Gln Val Leu Asp Ser Tyr Tyr Asp Ser Val Leu Lys Asp
            2500                2505                2510

Ile Lys Leu Ala Ala Ser Lys Val Thr Ala Arg Leu Leu Thr Met Glu
            2515                2520                2525

Glu Ala Cys Gln Leu Thr Pro Pro His Ser Ala Arg Ser Lys Tyr Gly
            2530                2535                2540

Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Ser Glu Thr Pro Ile
            2565                2570                2575

Pro Thr Thr Ile Met Ala Lys Asn Glu Val Phe Cys Val Asp Pro Thr
            2580                2585                2590

Lys Gly Gly Lys Lys Ala Ala Arg Leu Ile Val Tyr Pro Asp Leu Gly
            2595                2600                2605

Val Arg Val Cys Glu Lys Met Ala Leu Tyr Asp Ile Thr Gln Lys Leu
    2610                2615                2620

Pro Gln Ala Val Met Gly Ala Ser Tyr Gly Phe Gln Tyr Ser Pro Ala
2625                2630                2635                2640

Gln Arg Val Glu Phe Leu Leu Lys Ala Trp Ala Glu Lys Lys Asp Pro
            2645                2650                2655
```

-continued

```
Met Gly Phe Ser Tyr Asp Thr Arg Cys Phe Asp Ser Thr Val Thr Glu
        2660                2665                2670
Arg Asp Ile Arg Thr Glu Glu Ser Ile Tyr Arg Ala Cys Ser Leu Pro
    2675                2680                2685
Glu Glu Ala His Thr Ala Ile His Ser Leu Thr Glu Arg Leu Tyr Val
2690                2695                2700
Gly Gly Pro Met Phe Asn Ser Lys Gly Gln Thr Cys Gly Tyr Arg Arg
2705                2710                2715                2720
Cys Arg Ala Ser Gly Val Leu Thr Thr Ser Met Gly Asn Thr Ile Thr
            2725                2730                2735
Cys Tyr Val Lys Ala Leu Ala Ala Cys Lys Ala Ala Gly Ile Ile Ala
        2740                2745                2750
Pro Thr Met Leu Val Cys Gly Asp Asp Leu Val Val Ile Ser Glu Ser
        2755                2760                2765
Gln Gly Thr Glu Glu Asp Glu Arg Asn Leu Arg Ala Phe Thr Glu Ala
    2770                2775                2780
Met Thr Arg Tyr Ser Ala Pro Pro Gly Asp Pro Pro Arg Pro Glu Tyr
2785                2790                2795                2800
Asp Leu Glu Leu Ile Thr Ser Cys Ser Ser Asn Val Ser Val Ala Leu
            2805                2810                2815
Gly Pro Gln Gly Arg Arg Arg Tyr Tyr Leu Thr Arg Asp Pro Thr Thr
        2820                2825                2830
Pro Ile Ala Arg Ala Ala Trp Glu Thr Val Arg His Ser Pro Val Asn
    2835                2840                2845
Ser Trp Leu Gly Asn Ile Ile Gln Tyr Ala Pro Thr Ile Trp Ala Arg
2850                2855                2860
Met Val Leu Met Thr His Phe Phe Ser Ile Leu Met Ala Gln Asp Thr
2865                2870                2875                2880
Leu Asp Gln Asn Leu Asn Phe Glu Met Tyr Gly Ala Val Tyr Ser Val
            2885                2890                2895
Ser Pro Leu Asp Leu Pro Ala Ile Ile Glu Arg Leu His Gly Leu Asp
        2900                2905                2910
Ala Phe Ser Leu His Thr Tyr Thr Pro His Glu Leu Thr Arg Val Ala
        2915                2920                2925
Ser Ala Leu Arg Lys Leu Gly Ala Pro Pro Leu Arg Ala Trp Lys Ser
    2930                2935                2940
Arg Ala Arg Ala Val Arg Ala Ser Leu Ile Ser Arg Gly Gly Arg Ala
2945                2950                2955                2960
Ala Val Cys Gly Arg Tyr Leu Phe Asn Trp Ala Val Lys Thr Lys Leu
            2965                2970                2975
Lys Leu Thr Pro Leu Pro Glu Ala Arg Leu Leu Asp Leu Ser Ser Trp
        2980                2985                2990
Phe Thr Val Gly Ala Gly Gly Gly Asp Ile Tyr His Ser Val Ser Arg
    2995                3000                3005
Ala Arg Pro Arg Leu Leu Leu Phe Gly Leu Leu Leu Phe Val Gly
2010                3015                3020
Val Gly Leu Phe Leu Leu Pro Ala Arg
3025                3030
```

HCV/BVDV CHIMERIC GENOMES AND USES THEREOF

RELATED APPLICATIONS

This application represents the U.S. National Phase of International Application No. PCT/US00/15527 filed Jun. 2, 2000, designating the United States of America and published in English as WO 00/75352, which claims the benefit of priority of U.S. Provisional Application No. 60/137,817 filed Jun. 4, 1999, which is hereby expressly incorporated by reference in its entirety.

FIELD OF INVENTION

The present invention relates to molecular approaches to the production of nucleic acid sequences which comprise the genomes of chimeric hepatitis C virus-bovine viral diarrhea viruses (HCV-BVDV). The invention also relates to the use of these chimeric nucleic acid sequences to produce chimeric virions in cells and the use of these chimeric virions in HCV antibody neutralization assays, and for the development of vaccines and therapeutics for HCV.

BACKGROUND OF INVENTION

Hepatitis C virus (HCV) has a positive-sense single-strand RNA genome and is a member of the genus Hepacivirus within the Flaviviridae family of viruses (Rice, 1996). As for all positive-stranded RNA viruses, the genome of HCV functions as mRNA from which all viral proteins necessary for propagation are translated.

The viral genome of HCV is approximately 9600 nucleotides (nts) in length and consists of a highly conserved 5' untranslated region (UTR), a single long open reading frame (ORF) of approximately 9,000 nts and a complex 3' UTR. The 5' UTR contains an internal ribosomal entry site (Tsukiyama-Kohara et al., 1992; Honda et al., 1996). The 3' UTR consists of a short variable region, a polypyrimidine tract of variable length and, at the 3' end, a highly conserved region of approximately 100 nucleotides (Kolykhalov et al., 1996; Tanaka et al., 1995; Tanaka et al., 1996; Yamada et al., 1996). The last 46 nucleotides of this conserved region predicted to form a stable stem-loop structure thought to be critical for viral replication (Blight and Rice, 1997; Ito and Lai, 1997; Tsuchihara et al., 1997). The ORF encodes a large polypeptide precursor that is cleaved into at least 10 proteins by host and viral proteinases (Rice, 1996). The predicted envelope proteins contain several conserved N-linked glycosylation sites and cysteine residues (Okamoto et al., 1992a). The NS3 gene encodes a serine protease and an RNA helicase and the NS5B gene encodes an RNA-dependent RNA polymerase.

A remarkable characteristic of HCV is its genetic heterogeneity, which is manifested throughout the genome (Bukh et al., 1995). The most heterogeneous regions of the genome are found in the envelope genes, in particular the hypervariable region 1 (HVR1) at the N-terminus of E2 (Hijikata et al., 1991; Weiner et al., 1991). HCV circulates as a quasispecies of closely related genomes in an infected individual. Globally, six major HCV genotypes (genotypes 1–6) and multiple subtypes (a, b, c, etc.) have been identified (Bukh et al., 1993; Simmonds et al., 1993).

The nucleotide and deduced amino acid sequences among isolates within a quasispecies generally differ by <2%, whereas those between isolates of different genotypes vary by as much as 35%. Genotypes 1, 2 and 3 are found worldwide and constitute more than 90% of the HCV infections in North and South America, Europe, Russia, China, Japan and Australia (Forns and Bukh, 1998). Throughout these regions genotype 1 accounts for the majority of HCV infections but genotypes 2 and 3 each account for 5–15%.

At present, more than 80% of individuals infected with HCV become chronically infected and these chronically infected individuals have a relatively high risk of developing chronic hepatitis, liver cirrhosis and hepatocellular carcinoma (Hoofnagle, 1997). The only effective therapy for chronic hepatitis C, interferon (IFN), alone or in combination with ribavirin, induces a sustained response in less than 50% of treated patients (Davis et al., 1998; McHutchinson et al., 1998). Consequently, HCV is currently the most common cause of end stage liver failure and the reason for about 30% of liver transplants performed in the U.S. (Hoofnagle, 1997). In addition, a number of recent studies suggested that the severity of liver disease and the outcome of therapy may be genotype-dependent (reviewed in Bukh et al., 1997). In particular, these studies suggested that infection with HCV genotype 1b was associated with more severe liver disease (Brechot, 1997) and a poorer response to IFN therapy (Fried and Hoofnagle, 1995). As a result of the inability to develop a universally effective therapy against HCV infection, it is estimated that there are still more than 25,000 new infections yearly in the U.S. (Alter 1997) Moreover, since there is no vaccine for HCV, HCV remains a serious public health problem.

Despite the intense interest in the development of vaccines and therapies for HCV, progress has been hindered by the absence of a useful cell culture system for laboratory study (2–7). For example, although the virus has been grown in some cell lines, the level of replication is so low that RT-PCR assays are required for virus detection; these RT-PCR assays, especially those for negative strand RNA, are tedious and prone to artifacts, and the results have been difficult to reproduce.

SUMMARY OF THE INVENTION

The present invention relates to chimeric nucleic acid sequences which comprise the genomes of chimeric hepatitis C virus-bovine viral diarrhea viruses (HCV-BVDV). More specifically, the chimeric viruses are produced by replacing the structural region or a structural gene of a bovine viral diarrhea virus (BVDV) with the corresponding region or gene of an infectious hepatitis C virus (HCV).

The present invention also relates to the in vitro and in vivo production of chimeric HCV/BVDV viruses from the chimeric nucleic acid sequences of the invention.

The present invention also relates to the use of the chimeric viruses of the invention to identify cell lines capable of supporting the replication of the chimeric viruses.

The invention further relates to the use of the chimeric viruses of the invention to screen for neutralizing antibodies to HCV of different genotypes.

The invention also relates to the use of the chimeric nucleic acid sequences of the invention in the production of HCV-BVDV virions, and the use of these HCV-BVDV virions for the development of inactivated or attenuated vaccines to prevent HCV-BVDV in a mammal.

The invention also relates to the use of the chimeric nucleic acid sequences to study the molecular properties of HCV indirectly in vitro.

The present invention also relates to the polypeptides encoded by the chimeric nucleic acid sequences of the invention or fragments thereof.

The invention also provides that the chimeric nucleic acid sequences and the chimeric viruses of the invention be supplied in the form of a kit, alone or in the form of a pharmaceutical composition.

DESCRIPTION OF FIGURES

FIGS. 3A–3H show the nucleotide and deduced amino acid sequences of the infectious HCV clone of genotype 1a.

FIGS. 4A–4H show the nucleotide and deduced amino acid sequences of the infectious clone of genotype 1b.

DESCRIPTION OF THE INVENTION

Figure 1:
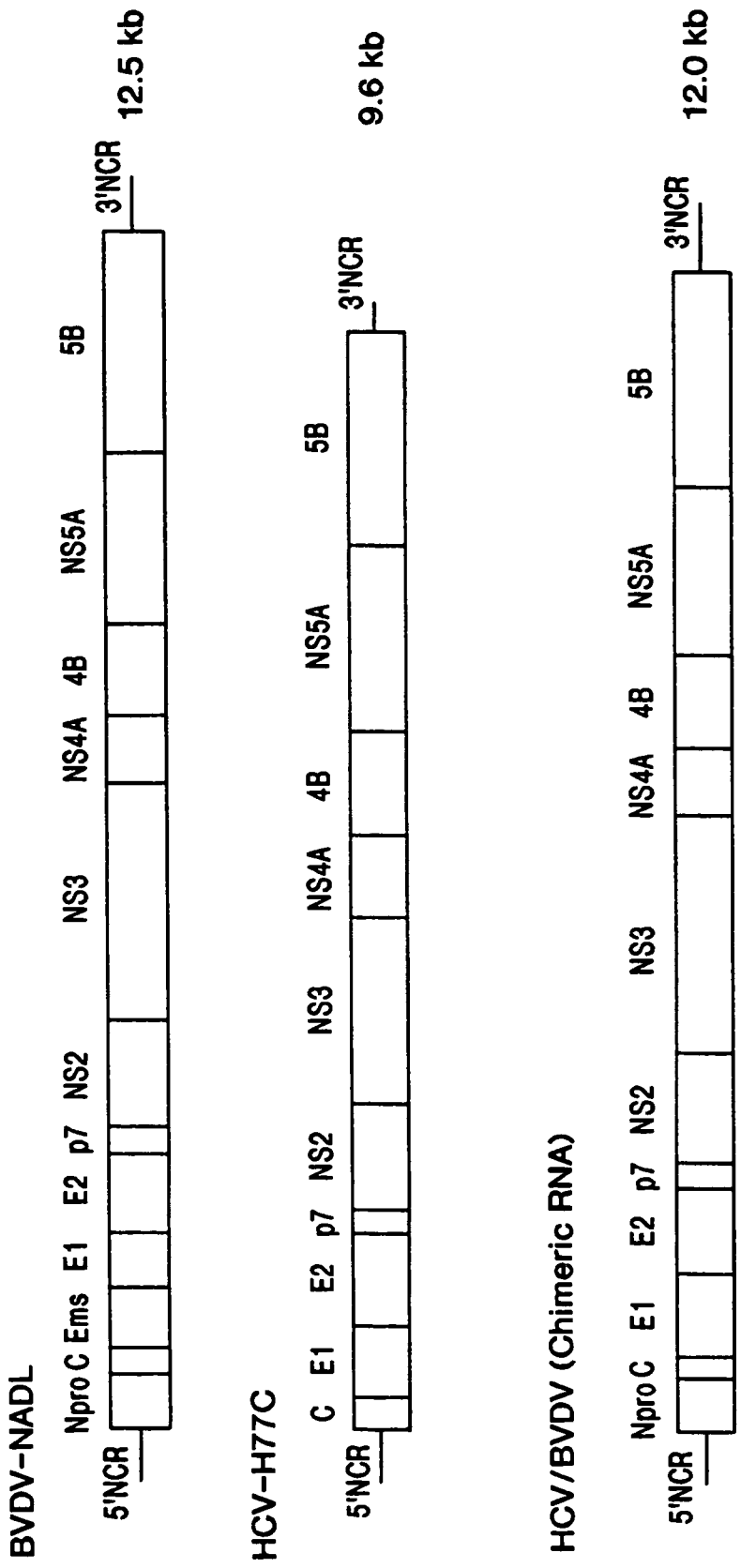
FIG. 1. Genomic organization of BVDV, HCV and HCV/BVDV chimera. The BVDV and HCV are NADL (14, 21) and H77 strains (12), respectively. The complete BVDV-NADL genome consists of, in 5' to 3' order, 5'NCR (nucleotides 1–385), $N^{pro}$ (nucleotides 386–889), Core (nucleotides 890–1195), $E^{rns}$ (nucleotides 1196–1876), E1 (nucleotides 1877–2461), E2 (nucleotides 2462–3583), P7 and nonstructural genes (nucleotides 3584–12349) and 3'NCR (nucleotides 12352–12578).

The present invention relates to nucleic acid sequences which comprise the genomes of chimeric HCV-BVDV. The chimeric viruses are produced by replacing the structural region or a structural gene (or fragment thereof) of a bovine viral diarrhea virus (BVDV) with the corresponding region or gene (or fragment thereof) of an hepatitis C virus (HCV). The gene borders of the HCV genome, including nucleotide and amino acid locations, have been determined, for example, as depicted in Houghton, M. (1996), and the putative gene borders of the BVDV genome are shown in FIG. 1.

In one embodiment, the chimeric nucleic acid sequence comprises the structural genes from an infectious HCV clone and the nonstructural genes and untranslated regions from an BVDV clone.

In another embodiment, additional HCV/BVDV chimeras can be constructed to study HCV infection of cell lines. For example, additional HCV/BVDV chimeras may be made in which only E1 and E2 genes of the BVDV infectious clone are replaced with the corresponding genes from an HCV clone. Such chimeras can be used to determine whether the core protein of BVDV is critical for encapsidation of the viral RNA. Alternatively, HCV/BVDV chimeras in which either the E1 or E2 gene of BVDV is replaced by the corresponding gene of HCV may be constructed. Such chimeras can be used to determine the relative importance of E1 or E2 for infection of cell lines. In another embodiment, HCV/BVDV chimeras in which one of the nonstructural genes of BVDV, such as NS3 RNA helicase, NS3 protease, or the NS5B RNA-dependent RNA polymerase are replaced by the corresponding non-structural genes of HCV may be constructed. Such chimeras would, for example, be useful in identifying inhibitors of viral enzyme activity which would be useful as antiviral agents.

In yet another embodiment, hypervariable region 1 (HVR1) from multiple HCV genotypes may be combined into one HCV/BVDV chimera. The only limit for constructing this type of chimera is that the viral genome must be able to be packaged. Alternatively, a chimera can be constructed which contain an HVR1 sequence from one HCV genotype. Such chimeras can be used as an inactivated multivalent vaccine or to screen for neutralizing antibodies to multiple HCV genotypes.

The HCV/BVDV chimeras of the invention may be constructed using any HCV and BVDV clones. However, in a preferred embodiment, the HCV clones are infectious HCV clones of genotype 1a (ATCC accession number PTA-157; FIGS. 3A–3F), 1b (ATCC accession number 209596; FIGS. 4A–4F) or 2a (ATCC accession number PTA-153; SEQ ID NOS: 3–4) and the infectious BVDV clone pVVNADL are used.

In constructing the chimeric nucleic acid sequences of the invention, it is to be understood that the retention of the $E^{rns}$ gene of BVDV in any chimeric is entirely optional. Thus, when it is stated that the HCV/BVDV chimeras could be constructed in which, for example, the E1 or E2 gene of BVDV is replaced by the corresponding E1 or E2 gene of HCV, it is to be understood that the resultant chimeras may or may not retain the BVDV $E^{rns}$ gene.

The present invention further relates to the production of chimeric HCV/BVDV viruses from the HCV/BVDV chimeras of the invention.

In one embodiment, the chimeric sequences of the invention can be inserted into an expression vector that functions in eukaryotic cells. Such eukaryotic expression vectors are well known to those of ordinary skill in the art and include, but are not limited to, plasmids, vaccinia viruses, retroviruses, adenoviruses and adeno-associated viruses.

The sequences contained in the recombinant expression vector can then be transcribed in vitro by methods known to those of ordinary skill in the art in order to produce RNA transcripts which encode the chimeric viruses of the invention. The chimeric viruses of the invention may then be produced by transfecting cells by methods known to those of ordinary skill in the art with either the in vitro transcription mixture containing the RNA transcripts or with the recombinant expression vectors containing the nucleic acid sequences described herein.

Where transfection of cells with recombinant expression vectors containing the nucleic acid sequences of the invention is used, transfection may be done by methods known in the art such as electroporation, precipitation with DEAE-Dextran or calcium phosphate, or incorporation into liposomes.

In one such embodiment, the method comprises the growing of animal cells in vitro and transfecting the cells with the chimeric nucleic acid of the invention, then determining if the cells show indicia of HCV infection. Such indicia include the detection of viral antigens in the cell, for example, by immunofluorescence procedures well known in the art; the detection of viral polypeptides by Western blotting using antibodies specific therefor; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the signs and symptoms of HCV infection. Alternatively, the presence of live, infectious virus particles following such tests may also be shown by serial passaging the chimeric virus in cells.

Suitable cells or cell lines for culturing the chimeric viruses of the invention include, but are not limited to, EBTr(A) and Huh7.

Preferably, transfection of cells with the chimeric sequences is carried out in the presence of helper BVDV which is preferably of a noncytopathogenic strain. In one embodiment, the cell lines to be infected may already contain a helper BVDV. Such cells include, but are not limited to, EBTr(A). Alternatively, the cell lines to be transfected may be infected with a helper BVDV prior to, or concurrent with, transfection with the chimeric sequences of the invention.

The present invention also relates to polypeptides encoded by the chimeric nucleic acid sequences of the invention or fragments thereof. In one embodiment, said polypeptide or polypeptides may be fully or partially purified from viruses produced by cells transfected with the chimeric nucleic acid sequences of the invention. In another embodiment, the polypeptide or polypeptides may be produced recombinantly from a fragment of the chimeric nucleic acid sequences of the invention. In yet another embodiment, the polypeptides may be chemically synthesized.

The present invention also relates to the use of the chimeric sequences of the invention to identify cell lines capable of supporting the replication of the chimeric viruses of the invention.

In another embodiment, the invention relates to the use of HCV/BVDV chimeras to screen for neutralizing antibodies to HCV of different genotypes. For example, chimeric viruses produced in cell lines infected with the chimeric clones of the invention can be used in neutralization assays to test the neutralizing ability of anti-HCV antibodies.

In yet another embodiment, the invention relates to the use of the infectious chimeric clones of the invention to develop inactivated or attenuated vaccines to prevent Hepatitis C in a mammal. For example, chimeric virions from cell lines infected with a chimeric virus of the invention, or transfected with a chimeric sequence of the invention, can be purified from the cells and inactivated by methods known to those of ordinary skill in the art. The inactivated HCV-BVDV virions can be used to immunize mice, and if neutralizing antibody to HCV is produced, the virions can then be used to immunize chimpanzees to determine whether the antibodies are protective. Alternatively, cells infected with the chimeric viruses of the invention may be passaged in cell culture to produce attenuated viruses which can be tested as candidate live vaccines. In assaying the ability of the chimeric viruses of the invention to infect mammals one can assay sera or liver of the infected mammal by RT-PCR to determine viral titer. In addition, the virulence phenotype of the virus produced by transfection of mammals with the sequences of the invention can be monitored by methods known in the art such as measurement of liver enzyme levels (alanine aminotransferase (ALT) or isocitrate dehydrogenase (ICD)) or by histopathology of liver biopsies.

Alternatively, mutations may be introduced into the HCV portion of the HCV/BVDV chimeras of the invention in order to enable the production of virions in cell cultures which could then be tested in vivo for improved vaccine properties.

In another embodiment, multiple chimeras containing HCV structural genes (or fragments thereof, such as the HVR1) from multiple genotypes can be administered to generate multivalent vaccines.

When used as a vaccine, the chimeric virions can be administered alone or in a suitable diluent, including, but not limited to, water, saline, or some type of buffered medium. The vaccine according to the present invention may be administered to an animal, especially a mammal, and most especially a human, by a variety of routes, including, but not limited to, intradermally, intramuscularly, subcutaneously, or in any combination thereof. Of course, it is understood that formulations or compositions comprising the chimeric virions of the invention may be used either therapeutically or prophylactically to treat or prevent the signs and symptoms of HCV.

The present invention therefore also relates to antibodies reactive with the HCV structural polypeptide(s) contained in the HCV-BVDV virions of the invention where such antibodies are produced following immunization with the HCV-BVDV virions.

The antibody molecules of the present invention may be polyclonal or monoclonal and may be useful in the prevention or treatment of diseases caused by HCV in mammals.

The invention also provides that the chimeric nucleic acid sequences and the chimeric viruses of the invention be supplied in the form of a kit, alone or in the form of a pharmaceutical composition.

All scientific publications and/or patents cited herein are specifically incorporated by reference. The following examples illustrate various aspects of the invention but are in no way intended to limit the scope thereof.

EXAMPLES

Materials and Methods

Cell Lines

The different cell lines used in the present study are listed in Table 1. Most cells were grown in Dulbecco's Minimum Essential Medium (DMEM) or DMEM-F12 supplemented with horse serum or with irradiated fetal calf serum. In some cases, Boyt serum, a fetal calf serum free of BVDV and antibodies to BVDV (Boyt Veternary, Neoshoe, Mo.) was used. All cells were incubated at 37° C. in 5% $CO_2$.

TABLE 1

List of Cell Lines

| Cell | Origin | Medium |
| --- | --- | --- |
| EBTr (A) | Embryonic bovine trachea | 10% FBS/MEM |
| BT | Bovine turbinate | 10% horse serum/MEM |
| MDBK | Bovine kidney | 10% horse serum/MEM |
| EBTr (B) | Embryonic bovine trachea | 10% FBS/MEM |
| Huh 7 | human hepatoma | 10% FBS/DMEM F12 |

Antibodies

H79: plasma from patient H obtained in the chronic phase two years after the onset of HCV infection (11); CH1530: serum pool from chimpanzee 1530, obtained in the chronic phase one to two years after the onset of HCV infection.

Chimpanzee 1530 became infected with HCV following intrahepatic transfection with pCV-H77C (Yanagi 1997); LMF86 and LMF87: anti-HVR1 (Farci 1996), rabbit anti-peptide sera; Mab NS: anti-BVDV NS3 murine monoclonal antibody kindly provided by Dr. E. Dubovi (Cornell University, Ithaca, N.Y.).

Construction of HCV/BVDV Chimeric Clone

Figure 2:
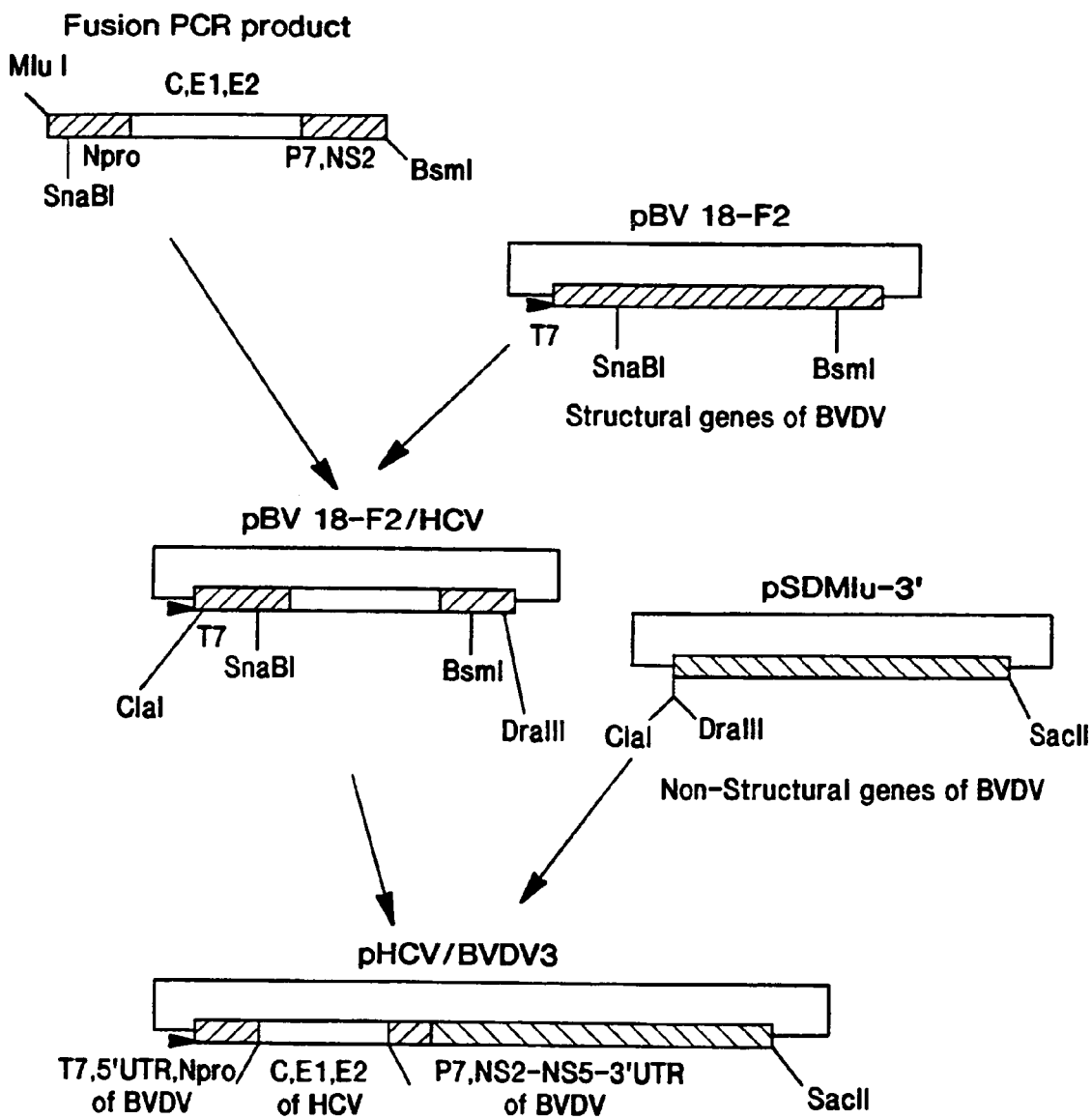
FIG. 2. Strategy for the construction of chimeric cDNA, pHCV/BVDV-3, which has core, E1 and E2 of HCV in the backbone of BVDV. The fusion PCR products were cloned into pBV18-F2 after digestion with SnaB I and Bsm I. The fragments containing fusion PCR products were cloned into pSDMlu-3' after digestion with Cla I and Dra III.

The C, E1 and E2 genes originating from an infectious clone of the H77 strain of HCV (pCV-H77C, ref. Yanagi 1997), and the backbone originating from two subgenomic plasmids (pBV18-F2 and pSDMlu-3'), used by Vassilev et al. (Vassilev 1997) to generate the infectious clone of the NADL strain of BVDV (pVVNADL), were used to construct the chimeric cDNA clone pHCV-BVDV-3 (ATCC deposit Number PTA-158). The chimeric clone includes sequences corresponding to nucleotides 345–2579 (amino acids 2–746) of the pCV-H77C clone of HCV and nucleotides 1–927 (amino acids 1–168) and nucleotides 3622–14578 (amino acids 1067–3988) of the pVVNADL clone of BVDV (FIG. 1). To generate the desired junctions between HCV and BVDV, standard PCR and fusion PCR were performed with pfu polymerase (Strategene) and the oligonucleotides listed in Table 2. One PCR fragment was amplified from pCV-H77C with primers Npro-C/H77/S and E2-P7/H77/R, two other fragments were amplified from pBV18-F2 with primers MluI/NADL/S and Npro-C/NADL/R and with primers E2-P7/NADL/S and BsmI/NADL/R, respectively. Following purification with the QIAquick PCR purification kit (Qiagen), the three PCR products were mixed and a fusion PCR was performed with primers MluI/NADL/S and BsmI/NADL/R. After purification, the fusion PCR product was cloned into pBV18-F2 by using SnaBI and BsmI sites (FIG. 2) and multiple clones were screened by sequence analysis. Finally, a clone with the correct sequence was digested with ClaI and DraIII and the insert was cloned into pSDMlu-3' to generate the full-length chimeric clone, pHCV/BVDV-3 (FIG. 2). This clone was transformed into JM109 competent cells (Promega) and selected on LB agar plates containing 100 μg/ml ampicillin (SIGMA). Several colonies were cultured in LB liquid containing ampicillin at 30° C. for 18–20 hrs. After small scale preparation (Qiagen Minipreps DNA Purification Systems), a plasmid preparation with the expected digestion pattern was retransformed to select a single clone, and large-scale preparation of plasmid DNA was performed with a QIAGEN plasmid Maxi kit as described previously (Yanagi 1997). The complete HCV/BVDV sequence of the final preparation was determined using standard procedures and about 90 specific sense and antisense primers. Clone pHCV/BVDV-3 was apparently stable since the digestion pattern was as expected following retransformation. The complete sequence differed slightly from the published BVDV sequence of the NADL strain (21), but encoded an intact polyprotein.

TABLE 2

Oligonucleotides used for PCR amplification

| Name | Sequences (5'–3') | Underline |
|---|---|---|
| N-C/H77/S | CAAGTTGCAGCACGAATCCTAAACCTCAAAGAA | N OF BVDV-NADL |
| MluI/NADL/S | CACGCGTATCGATGAATTCG | Mlu i |
| B2-P7/NADL/S | AGCGGAGGCGATTCAGTATGGATCAGGGGAAGTG | E2 OF HCV |
| E2-P7/H77/R | ATACTGAATCGCCTCCGCTTGGGATATGAG | P7 OF BVDV-NADL |
| N-C/NADL/R | AGGATTCGTGCTGCAACTTGTGACCCATAGAGGCAGTC | Core OF HCV |
| BanI/NADL/R | TACCAGGCTGAGAATGCACTGTAAC | Bsm I |
| 2937S-HCBV | CCTTGTCCACCGGCCTCATCCACCTCCACC | |
| 1353S-NADL | CAATTCATGGTATGATGGATGC | |
| 1419S-NADL | AGTGGAACAAGCATGGTTGGTG | |
| 2335-NADL | CCACGTGGACGAGGGCATGCC | |
| 3342R-NADL | CCTGAATCGGCCTTTACCACATCCCCAATC | |
| 1623R-NADL | TTCTTTCCTTTCTTGCAACCTGT | |
| 1590R-NADL | GGGCTATCTCTAGCTTGTGTTAC | |
| 389R-NADL | CCATGTGCCATGTACAGCAGAG | |

Transfection of Cell Lines with Transcribed RNA

The plasmid pHCV/BVDV-3 was linearized with SacII (NEB) and treated with T4 DNA polymerase (GIBCO/BRL) to remove the resulting 3' overhang. A truncated form of pHCV/BVDV-3, generated by digestion with HindIII, was used as a negative control. Two micrograms of DNA were transcribed at 37° C. for 2 hrs in a 100 μl reaction volume containing 50 U of T7 RNA polymerase (Promega), 10 mM DTT (Promega), 120 U of Rnasin (Promega) and 1 mM rNTPs (GIBCO/BRL). Five microliters of the final reaction mixture was analyzed by agarose gel electrophoresis and ethidium bromide staining. The RNA of each transcription mixture was extracted with the TRIzol system (GIBCO/BRL) and resuspended in 50 μl of DEPC-treated water, and stored at −80° C.

For transfection, 3–5 μg of RNA was added to 1 ml of Optimem with 15 μl of DMRIE-C (GIBCO/BRL) and incubated with cells for 5 hrs. The Optimem was removed and complete medium was added. Cells were cultured in the presence of the appropriate medium (Table 1) and transfected at 80% confluency either in one well of a 12 well plate (Costar) or in a 60 mm dish (Costar). About 24 hrs prior to immunofluorescent staining, transfected cells were split into 4- or 8-well chamber slides (LAB-TEK).

Serial Passage From Transfected or Infected Cells

The supernatant was collected and stored at −80° C. Cells were scraped with 1 ml of supernatant medium and centrifuged. The pellet was taken through three freezing and thawing cycles to lyse the cells. For homologous passages, lysed cells or supernatant (100–500 μl) were transferred onto new cells of the same type. For heterologous passages, lysed cells or supernatant from EBTr(A) cells were transferred onto different cell lines. Inoculated cells were incubated at 37° C. for two hrs followed by the addition of complete medium. Inoculated cells were incubated at 37° C. for 4–12 days.

Immunofluorescent Staining of Transfected or Infected Cells

Cells grown on chamber slides were fixed and permeabilized with cold acetone for 5 min and washed with phosphate buffered saline (PBS) for 10 min. Thereafter, cells were incubated for 20–60 min at 37° C. with primary antibodies diluted in 10% bovine serum albumin (BSA) in PBS. As primary antibodies we used an anti-HCV human plasma sample (H79, 1:100 dilution), an anti-HCV chimpanzee serum (CH1530, 1:100 dilution) and an anti-BVDV NS3 monoclonal antibody (Mab-NS, 1:10 dilution). After washing with PBS for 15 min, cells were incubated for 20–40 min at 37° C. with secondary antibodies; fluorescein-isothiocyanate (FITC)-conjugated goat anti-human antibody (SIGMA) for H79 and CH1530, and rhodamine-conjugated anti-mouse antibody (PIERCE) for anti-BVDV NS3. For double staining, H79 or CH1530 anti-HCV antibody was mixed with the anti-BVDV NS3 monoclonal antibody and incubated on fixed cells as above, followed by washing and incubation with a mixture of both secondary antibodies. After washing, slides were mounted and examined by fluorescence microscopy (Zeiss).

Determination of Sucrose Gradient Density of Recovered Viruses

A T150 flask of EBTr(A) cells was inoculated with virus stock. At days 9 and 13, respectively, supernatant was harvested. A total of 70 ml of supernatant was layered over 20% sucrose in TN buffer [50 mM Tris and 100 mM NaCl (pH 7.4)] and centrifuged at 28,000 rpm in an SW28 swinging bucket rotor (Beckman) for 19 hrs at 4° C. The pellet was resuspended in 100 µl of TN buffer. For sucrose equilibrium gradient centrifugation, the resuspended pellet was layered onto a 20–60% (wt/wt) sucrose gradient in TN buffer and centrifuged at 36,000 rpm in an SW40 swinging bucket rotor (Beckman) for 20 hrs at 4° C. Fractions of 500 µl each were collected from the bottom of the tube, and the density was determined by refractometry. Finally, the different fractions obtained by RT-PCR were tested for the presence of chimeric HCV/BVDV genomes.

Western Blotting for HCV Structural Proteins

For immunoblotting analysis, EBTr(A) cells (60 mm dish) infected with the HCV/BVDV chimeric virus were lysed by adding 300 $\mu$l of M-PER mammalian protein extraction reagent (PIERCE). The cell lysate was cleared of cell debris by low speed centrifugation at 13000 rpm for 5 min. Also, thirty ml of the supernatant from EBTr(A) cells infected with chimeric virus stock was harvested, ultra centrifuged and tested for HCV proteins by immunoblot. Thirty ml of supernatants was layered over 20% sucrose in TN buffer and centrifuged at 28,000 rpm in a SW28 swinging bucket rotor (Beckman) for 19 hrs at 4° C. The pellet was resuspended with 50 $\mu$l of TN buffer and 20 $\mu$l was assayed by immunoblot. For separation of proteins, 20 $\mu$l of lysate or pellet was electrophoresed through a sodium dodecyl sulfate—12% polyacrylamide gel (SDS-PAGE) and then proteins were transferred onto a nitrocellulose membrane (NOVEX). The membrane was incubated at 4° C. for 16 hrs with CH1530 anti-HCV (1:750 dilution) in a blocking buffer containing 1% BSA in TBST buffer (20 mM Tris-HCl, pH 7.5; 150 mM NaCl, 0.05% Tween 20). Following washing with TBST buffer, the membrane was incubated at room temperature for 1 hr with a 1:5000 dilution of goat anti-human immunoglobulin conjugated to horseradish peroxidase (PIERCE). After washing, the membrane was incubated with ECL Western blotting detection reagent (Amersham) and exposed to film.

Detection of Chimeric Genomic RNA by RT-PCR Assays

Total RNA was extracted with the TRIzol reagent from 10 or 100 $\mu$l of cell suspension, supernatant or material from the sucrose gradient. The RNA pellet was resuspended in 10 mM dithiothreitol (DTT) containing 5% (vol/vol) of RNAsin (20–40 U/$\mu$l) (Promega). The RT was performed with avian myeloblastosis virus reverse transcriptase (Promega) and the external anti-sense primer (see below) and PCR was performed with AmpliTaq Gold DNA polymerase (Perkin Elmer) as described (Bukh 1998a). Specificity was confirmed by sequence analysis of selected DNA products. Each set of experiments included a low titer positive control sample and appropriate negative controls. HCV/BVDV chimeric genomes were detected in one round of PCR with the primers 2937S—HCBV and 3342R—HCBV (Table 2). The structural region of BVDV was detected in an RT-nested PCR with external primers 1353S-NADL and 1623R-NADL and internal primers 1419S-NADL and 1590R-NADL (Table 2). These primers were conserved among all known BVDV strains. Finally, the 5' UTR sequence of BVDV was detected by using universal primers that detect both HCV and BVDV (Bukh 1992, Yanagi 1996), as well as universally conserved BVDV primers (233S-NADL and 389R-NADL). The genome equivalent (GE) titer of HCV, BVDV and HCV/BVDV in positive samples was determined by RT-nested PCR on 10-fold serial dilutions of the extracted RNA (Bukh 1998a). One GE was defined as the number of genomes present in the highest dilution positive in RT-nested PCR. The sensitivity of the RT-PCR assays for HCV/BVDV was established by comparison with the HCV titer determined by using HCV primers with established optimal sensitivity. The consensus sequence of the chimeric HCV/BVDV genome was determined by direct sequencing of overlapping PCR products obtained by long RT-nested PCR on supernatant from infected EBTr(A) cells.

Chimeric Virus Stocks

Medium harvested from EBTr(A) cells infected with serially passaged chimeric virus was frozen at −80° C. and thawed only once.

Focus Assay

EBTr(A) cells were trypsinized, diluted in DMEM containing 10% Boyt fetal calf serum, (10% Boyt DMEM) and plated in 2 well chamber slides at 37° C. with 5% $CO_2$. When the cells were confluent, the medium was aspirated and 200 $\mu$l of chimeric virus diluted in 10% Boyt DMEM was added and the cells were gently rocked for 2 hours at room temperature. Cells were then overlaid with 2 ml/well of 0.5% low melting point agarose in minimal essential medium containing 2% fetal calf serum, 20 mM glutamine and 250 $\mu$g of gentamicin sulfate/ml. After the agar solidified, the slides were incubated at 37° C. and 5% $CO_2$. After 4 days, the chambers were removed and the agarose discarded. Slides were rinsed briefly in cold phosphate buffered saline (PBS) and immersed in acetone for fixation. Slides were air dried and stained at room temperature for 30 minutes with 100 µl/well of CH1530 anti-HCV serum in diluent containing 1 part 10% bovine serum albumin to 1 part PBS. Slides were washed 5 minutes in PBS. Color development was by the Vectastain Elite kit (Vector Laboratories, Burlingame, Calif.) for peroxidase staining per the manufacturer's directions. The peroxidase substrate kit was Vector VIP (Vector Laboratory). Color development was stopped by washing the slide with water followed by air drying. Foci were counted with the aid of a dissecting microscope.

Focus Neutralization Assay

The assay was performed exactly as for the focus assay except the 200 µl inoculum consisted of 100 µl of chimeric virus diluted in 10% DMEM, 20 µl undiluted test or control serum, and 80 µl 10% DMEM. Each 200 µl sample was incubated at 4° C. in ice overnight prior to inoculation of cells. Sera included fetal calf serum (Boyt) and rabbit pre-immune serum as negative controls, hyperimmune rabbit antisera raised to peptides spanning the HVR1 region of the H27 strain of HCV (Farci, 1996), and goat anti-BVDV (VMRD Pullman, Wash.) prepared without azide. All sera had been heat-inactivated at 56° C. for 30 minutes.

Immunofluoresence Neutralization Assay in Huh7 Cells

Two hundred microliters of chimeric virus was mixed with 20 µl of serum or plasma, incubated on ice overnight and added to one well of a four-well chamber slide. After 2 hours at 30° C., 1 ml of agarose overlay was added as for the focus assay. Four days later, slides were fixed and stained as for immunofluoresence microscopy and stained cells were manually counted by scanning the entire well using a Zeis microscope and the 40× objective.

RESULTS

RNA genomes transcribed from the chimeric virus cDNA pHCV-BVDV-3 were transfected into four bovine cell lines, including two independently derived lines of embryonic bovine trachea cells (EBTr). Cells from all four transfected cell lines produced HCV proteins as evidenced by immunofluorescence microscopy using anti-HCV serum (Table 3). However, upon continued incubation, the number of stained cells remained low (<1 percent) in all except the EBTr(A) line, in which approximately 10 percent of cells stained by day 10. The medium from the transfected EBTr(A) cell line was serially passaged onto new EBTr(A) cells. By the fifth passage, approximately 70 percent of the cells were stained with anti-HCV serum. At passage 5, the entire open reading frame of the genome was amplified by RT-PCR and sequenced. Only one amino acid change, (lys to arg) in the NS3 gene (nucleotide 5373, A to G), was found. This single amino acid mutation coincided with the increased infectivity and may represent an adaptive mutation. After the 10th serial passage in EBTr(A) cells the medium contained $10^8$ to $10^9$ GE/ml of chimeric genome.

Figure 5:
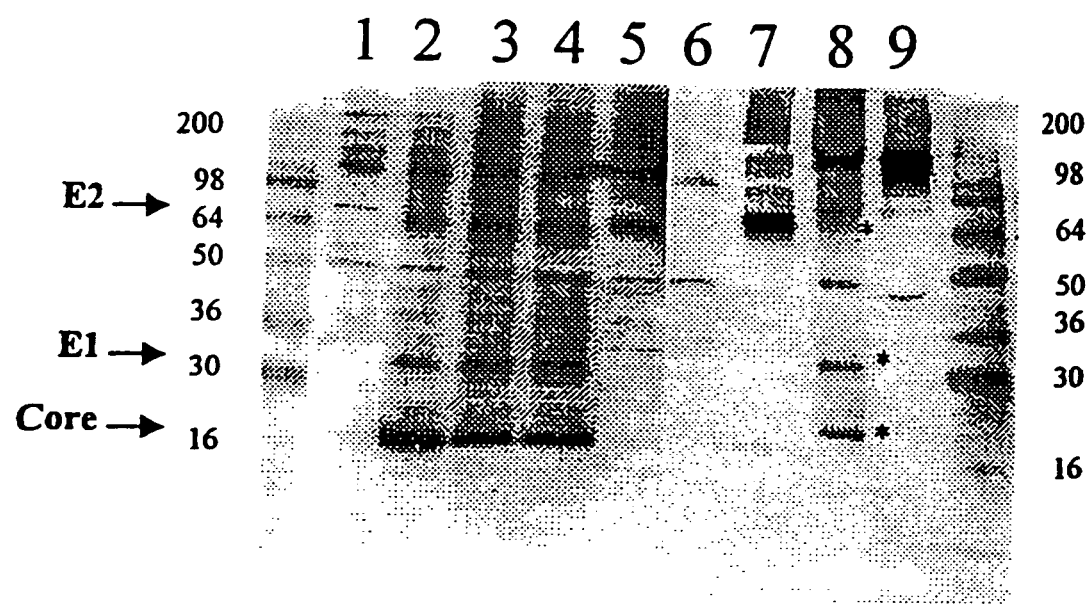
FIG. 5 shows a Western blot of lysate and supernatant from EBTr(A) cells infected with chimeric HCV-BVDV clone pHCV-BVDV-3 using antibody to HCV E1, E2 or core proteins.

A Western blot of material pelleted from the medium by ultracentrifugation revealed anti-HCV reactive bands consistent in size with core, E1 and E2 proteins of HCV (FIG. 5). The chimeric genomes, concentrated by high-speed centrifugation, banded in a sucrose gradient at a density of 1.119 to 1.128 g/ml, suggesting that they were in enveloped virus particles. The sucrose banding pattern, coupled with the Western blot data, suggest that the chimeric genome was enveloped in a particle containing significant amounts of HCV proteins.

Although the proportion of cells producing HCV proteins increased in EBTr(A) cells, it remained low in the MDBK, BT, and EBTr(B) cell lines, suggesting that the virus was not spreading in these cells. In order to determine if these cells were making infectious virus, a homologous transmission was attempted by removing supernatant from each transfected culture and adding it to a new culture of the same cell line. The only successful transmission was from the transfected EBTr(A) cells to naive EBTr(A) cells (Table 3). Therefore, although the chimeric virus genome could replicate in all four cell lines and produced HCV proteins, only in the EBTr(A) cells was virion morphogenesis coupled with availability of a receptor conducive to infection.

TABLE 3

Homologous passage and heterologous passage

| | Transfection | Homologous passage | Heterologous passage |
|---|---|---|---|
| EBTr (A) | + | + | |
| EBTr (B) | + | − | + |
| BT | + | − | + |
| MDBK | + | − | + |

[1]Supernatants from transfected cells were passed onto new cells of the same type.
[2]Supernatants from transfected EBTr (A) cells were passed to indicated cells.

Two heterologous transmission experiments were performed to determine if the three other cell lines released infectious particles. In the first experiment, supernatant from transfected MDBK cells was inoculated onto the EBTr(A) cells. Immunofluorescence microscopy showed that the cells did not produce HCV proteins, suggesting that infectious particles had not been produced by the transfected MDBK cells. In the second experiment, heterologous transmission of known infectious chimeric virus was attempted. Medium from transfected EBTr(A) cells was inoculated onto cultures of each of the other three cell lines. All of the cell lines became infected, indicating that each displayed a functional receptor for the chimeric virus. Therefore, the MDBK, BT and EBTr(B) cell lines all were permissive for chimeric virus entry and viral genome replication.

The EBTr(A) cells were obtained from the ATCC (ATCC ascession number CLL44) and were not listed as being contaminated with BVDV (9). However, one of the antibodies used to check replication of the chimera was raised against the NS3 protein of the NADL strain of BVDV. At high concentrations this antibody stained, on average, 30–40 percent of uninfected EBTr(A) cells but did not stain EBTr(B) cells, MDBK or BT cells. Therefore, it appeared that EBTr(A) cells either were persistently infected with a non-cytopathogenic strain of BVDV, or were harboring a BVDV replicon, or were producing a protein that cross-reacted with the anti-NS3 antibody. To discriminate among these possibilities, medium from naive EBTr(A) cells was inoculated onto MDBK cells. The cells were incubated at 37° C. for 4 days and stained with anti-BVDV serum to NS3. A high proportion of the inoculated cells stained with anti-NS3 whereas parallel uninoculated cultures remained negative for NS3 staining. From this result, it was concluded that the EBTr(A) cell line was contaminated with a transmissible agent, most likely a noncytopathogenic strain of BVDV. RT-PCR primers designed to amplify known BVDV strains were able to amplify a cDNA fragment from uninoculated EBTr(A) cultures (titer: $10^6$ GE/ml). The sequence of the cDNA was determined and found to match that of the CP-7 strain of BVDV (18).

Based on the data that only EBTr cells harboring BVDV were able to produce infectious particles containing the chimeric genome, it was hypothesized that the endogenous virus was serving as a helper virus, possibly by providing BVDV structural proteins. In order to determine if the infectious chimeric particles contained BVDV glycoproteins, a focus assay was developed in which cells expressing the chimeric genome were identified by their reactivity with CH1530 anti-HCV serum. An infectivity titer of $10^5$ chimeric viruses/ml was obtained for passage 10 virus, which had an RT-PCR titer of $10^8$ to $10^9$ GE/ml. Chimeric virus produced in EBTr(A) cells was examined for its susceptibility to neutralization by anti-serum to BVDV as compared to neutralization by anti-sera raised against the hypervariable region 1 (HVR1) of the same HCV strain as was in the chimera. Dilutions of chimeric virus were incubated overnight with anti-BVDV, anti-HCV or control sera and the number of infectious particles remaining was determined by the focus assay (Table 4). The number of foci in the rabbit and bovine serum controls decreased in parallel with the dilution factor, indicating that the assay was linear and reliable. The anti-HCV sera did not neutralize the chimera. In contrast, anti-BVDV eliminated all foci at each dilution, suggesting that each and every infectious particle contained BVDV glycoproteins and that they were probably serving as the viral receptor for binding to the bovine cells. Therefore, the chimeric virus was actually also a pseudotype since the virion contained glycoproteins contributed by a helper virus.

TABLE 4

Neutralization Assay (Number of Foci/Well)

| Virus | Serum | | | | |
|---|---|---|---|---|---|
| dilution[1] | LMF86[2] | LMF87[2] | 554[3] | FCS[4] | anti-BVDV[5] |
| 1:1000 | 154[6] | 148[6] | 168[6] | 148[6] | 0 |
| 1:3,200 | 65 | 72 | 61 | 61 | 0 |
| 1:10,000 | 25 | 29 | 20 | 25 | 0 |

[1]Chimeric virus harvested from the 10th serial passage in EBTr (A) cells.
[2]hyperimmune rabbit sera to HVR1 of the H77 strain of HCV.
[3]normal rabbit serum.
[4]fetal calf serum from Boyt.
[5]goat anti-BVDV serum.
[6]the number of foci is approximate due to the difficulty in counting overlapping foci.

Western blots of harvested medium described above (FIG. 3) suggested that the HCV glycoproteins were present on the virions in significant amounts even though the chimera was not neutralized by the anti-HVR1 serum.

There are several possible explanations for the failure of the anti-HVR1 serum to neutralize HCV glycoproteins. First, the neutralizing titer may not have been high enough. An earlier bleeding from rabbit LMF87 was able to neutralize 64 chimpanzee infectious doses of the H77 strain of HCV in both of two attempts when tested in chimpanzees. The anti-HVR1 serum we used was from a later bleeding and had not been similarly tested for neutralizing antibodies. Secondly, the HCV glycoproteins might not bind to bovine cells and entry into these cells might be totally independent of HCV glycoprotein. Thirdly, the HCV E2 glycoprotein might not have folded properly to function or to be recognized by the antibody. The question of the neutralizing potential of the anti-HVR1 serum cannot be answered at this time. By an immunofluoresence microscopy assay, the anti-HVR1 serum had titers of 1:1600 and 1:3200 for rabbits LMF86 and LMF87 respectively but the antibody detected by this assay is not necessarily neutralizing antibody. The functionality of the HCV glycoproteins would best be proved by infecting cells which are not susceptible to infection by BVDV due to an absence of the BVDV receptor. Huh 7 cells were chosen as an experimental system to test for functional HCV glycoproteins because they are a human cell line which grows well and is of hepatocyte origin. Attempts to infect Huh 7 cells with the endogenous BVDV virus of the EBTr(A) cell line were not successful, suggesting either that the receptor for BVDV was absent or that the BVDV genome was unable to replicate in these cells. Attempts to infect the Huh 7 cells with the chimera were more successful. Four days after incubation with $2\times10^4$ EBTr(A) tissue culture infectious doses (TCID) of the chimera, Huh 7 cells could be stained with antibody to NS3 as well as with antibody to HCV. Quantification of the number of infected cells indicated that the inoculum contained $10^3$ TCID/ml for Huh 7 as compared to $10^5$/ml for EBTr(A) cells. Although the cells could be infected, the virus did not spread, suggesting that in Huh 7 cells, as in the MDBK and BT cells, virions either were not assembled or were not released from cells. Most likely, the CP-7 virus could not provide the required helper function because it could not enter the cells. This suggested that at least one of the HCV glycoproteins was functioning as a receptor or receptor-component for entry into Huh 7 cells. However, entry into Huh 7 cells was not blocked by preincubation with rabbit LMF87 anti-HVR1 serum but was totally blocked by anti-BVDV serum (Table 5). Therefore, it was possible that one or both of the HCV glycoproteins was functioning in association with one or both of the BVDV glycoproteins, which would have been incorporated during growth in the persistently infected EBTr(A) cells. The failure to neutralize with the anti-HVR1 serum might be due to low neutralizing titers, to mediation of virus entry into these cells by E1 rather than E2 or to interference with antibody binding to the HVR1 because of the BVDV glycoproteins.

The neutralization assay was repeated on Huh 7 cells using human chronic phase plasma (H79) that had, like LMF87 rabbit serum, been shown to neutralize the H72 strain of HCV in a chimpanzee experiment (Farci et al. Proc. Natl. Acad. Sci. USA 91:7792–7796, 1994) (Table 6). Plasmas from 3 chimpanzees that had either been experimentally infected with a monoclonal virus of the H72 strain of HCV (Ch1530 and 1494) or vaccinated with a DNA vaccine expressing the E2 glycoprotein of HCV were also tested. The results suggested that two of the four samples tested contained neutralizing antibodies to HCV. The sample incubated with the human H79 plasma did not infect any cells indicating complete neutralization while the sample incubated with plasma from the DNA vaccinated chimp infected only ⅓ to ¼ s many cells as the control suggesting it also had neutralizing antibody but at a lower titer. Since the DNA vaccine expressed only the E2 glycoprotein, this protein must be involved in binding to Huh 7 cells. The plasma from chimp 1530 contained antibodies to the HCV envelope proteins as measured by ELISA or immunofluoresence microscopy but apparently, these were not neutralizing antibodies. Chimpanzee 1494 did not have demonstrable antiodies against the HCV glycoproteins so its failure to neutralize was not unexpected. Therefore, the chimera should be very useful for screening samples for neutralizing antibodies and discriminating between those that neutralize as compared to those that just bind.

TABLE 5

Neutralization of chimeric virus growth in Huh 7 cells[1]

| Virus dilution | Fetal Calf Serum (Boyt) | Anti-HCV HVR1 | Anti-BVDV |
|---|---|---|---|
| Undiluted | 191 | 298 | 0 |
| Dilution (1:10) | 23 | 43 | 0 |

[1]Huh 7 cells were used for infection but the virus had been grown in EBTr (A) cells.
[2]Foci stained with chimp 1530 anti-HCV and visualized by immunofluoresence microscopy.

TABLE 6

Neutralization of chimeric virus growth in Huh 7 cells[1]
Number of foci[2]

| Fetal Calf Serum (Boyt) | Anti-HCV CH 1530 | Anti-HCV H79 | Anti-HCV CH 3001 | Anti-HCV CH 1494 |
|---|---|---|---|---|
| 46 | 37 | 0 | 12 | 38 |

[1]Huh 7 cells were used for infection but the virus had been grown in EBTr (A) cells; viruses were undiluted.
[2]Foci stained with chimp 1530 anti-HCV and visualized by immunofluoresence microscopy.

DISCUSSION

A chimeric genome consisting of HCV structural genes and BVDV nonstrucural genes and untranslated regions was able to replicate in cell lines of bovine and human origin. The HCV glycoproteins and core protein were efficiently expressed from this genome. Virion particles incorporating the chimeric genome were formed only in the presence of an endogenous BVDV helper virus that provided E1 and/or E2 BVDV glycoproteins to each infectious particle. In the presence of helper virus, this chimera replicated to high titers and significant amounts of HCV glycoprotein were released from the cells. Whereas the BVDV glycoproteins are believed to mediate entry into the bovine cells, the HCV glycoproteins on the virions are believed to mediate entry of the chimeric virus into cultured hepatocytes (Huh 7 cells) where the genome replicated via the BVDV non-structural proteins.

Since the chimeric virus replicated to such high levels and such large quantities of HCV glycoproteins were synthesized, it would be feasible to test purified chimeric virions as a candidate inactivated vaccine. Purified chimeric virions can be tested first in mice and if antibody to HCV is produced, the virions will be tested in chimpanzees to determine if the candidate vaccine is efficacious. The fact that virions grown in EBTr(A) cells were able to infect Huh 7 cells and were neutralized by some anti-HCV positive plasmas (Table 6) suggests that such chimeric viruses could be used to screen for neutralizing antibodies to HCV as well as to screen other cell lines for HCV receptors. The infectivity of the chimera proves the principle that HCV-BVDV chimeras can serve as a useful tool for studying the molecular biology of HCV. The glycoprotein genes from the five other genotypes of HCV can be similarly inserted into the BVDV backbone in order to provide an assay for antibodies to each genotype. Additional chimeras are being constructed in which the core protein of BVDV is included so that only the glycoproteins of HCV are introduced. If BVDV core is critical for encapsidation of the RNA, it may be possible to generate chimeric viruses in the absence of helper. It will also be revealing to determine if the HCV contribution to the chimera can be localized to either E1 or E2 alone. Such a chimera will be tested for its ability to infect EBTr(A) and Huh 7 cells. These studies will help determine the relative importance of E1 and E2 for infection of Huh 7 cells and may define any association with the BVDV glycoproteins. In addition, chimeras in which the BVDV nonstructural genes such as p7 or NS4B or NS5A are replaced with the corresponding genes of HCV may also be generated to determine if they are functional in cell culture.

REFERENCES

1. Major M E and Feinstone S M. The molecular virology of hepatitis C. Hepatology 1997; 25:1527–1538.
2. Mizutani T, Kato N, Horota M, Sugiyama K, Murakami A, and Shimotohno K. Inhibition of hepatitis C virus replication by antisense oligonucleotide in culture cells. Biochem Biophys Res Commun 1995; 212:906–911
3. Shimizu Y K and Yoshikura H. Multicycle infection of hepatitis C virus in cell culture and inhibition by alpha and beta interferons. J Virol 1994; 68:8406–8408.
4. Kato N, Nakazawa T, Mizutani T, and Shimotohno K. Susceptibility of human T-lymphotropic virus type I infected cell line MT-2 to hepatitis C virus infection. Biochem Biophys Res Commun 1995; 206:863–869.
5. Cribier B, Scmitt C, Bingen A, Kirn A and Keller F. In vitro infection of peripheral blood mononuclear cells by hepatitis C virus. J Gen Virol 1995; 76:2485–2491.
6. Yoo B J, Selby M, Choe J, Suh B S, Joh J S, Nuovo G J, Lee H S, Noughton M and Han J H. Transfection of a differentiated human hepatoma cell line (Huh7) with in vitro-transcribed hepatitis C virus (HCV) RNA and establishment of a long-term culture persistently infected with HCV. J Virol 1995; 69:32–38.
7. Nakajima N, Hijikata M, Yoshikura H and Shimizu YK. Characterization of long-term cultures of hepatitis C virus. J Virol 1996; 70:3325–3329.
8. Meyers G and Thiel H-J. Molecular characterization of pestiviruses. Adv Virus Res 1996; 47:53–118.
9. Bolin S R, Ridpath J F, Black J, Macy M and Roblin R. Survey of cell lines in the American Type Culture Collection for bovine viral diarrhea virus. J Virol Meth 1994;48:211–221.
10. Behrens S-E, Grassmann C W, Thiel H-J, Meyers G and Tautz N. Characterization of an autonomous subgenomic pestivirus RNA replicon. J Virol 1998; 72:2364–2372.
11. Farci P, Alter H J, Wong D C, Miller R H, Govindarajan S, Engle R, Shapiro M and Purcell R H. Proc Natl Acad Sci USA 1994; 91:7792–7796.
12. Yanagi M, Purcell RH, Emerson SU and Bukh J. Transcripts from a single full-length cDNA clone of hepatitis C virus are infectious when directly transfected into the liver of a chimpanzee. Pro Natl Acad Sci USA 1997; 94:8738–8743.
13. Farci P, Shimoda A, Wong D, Cabezon T, Gioannis DD, Strazzera A, Shimizu Y, Shapiro M, Alter H J and Purcell RH. Prevention of hepatitis C virus infection in chimpanzees by hyperimmune serum against the hypervariable region 1 of the envelope 2 protein. Pro Natl Acad Sci USA 1996; 93:15394–15399.

14. Vassilev V B, Collett M S and Donis R O. Authentic and chimeric full-length genomic cDNA clones of bovine viral diarrhea virus that yield infectious transcripts. J Virol 1997; 71(1): 471–478.
15. Bukh J, Kim J P, Govindarajan S, Apgar C L, Foung S K H, Wages J, Yun A J, Shapiro M, Emerson S U and Purcell R H. Experimental infection of chimpanzees with hepatitis G virus and genetic analysis of the virus. J Infect Dis 1998; 177:855–862.
16. Bukh J, Purcell RH and Miller R. Importance of primer selection for the detection of hepatitis C virus RNA with the polymerase chain reaction assay. Proc Batl Acad Sci USA 1992; 89:187–191.
17. Yanagi M, Buck J, Emerson SU and Purcell RH. Contamination of commercially available fetal bovine sera with bovine viral diarrhea virus genomes: Implications for the study of hepatitis C virus in cell cultures. J Infect Dis 1996; 174:1324–1327.
18. Meyers G, Tautz N, Becher P, Thiel H J and Kummerer B M. Recovery of cytopathogenic and noncytopathogenic bovine viral diarrhea viruses from cDNA constructs. J. Virol. 1996; 70 (12): 8606–8613.
19. Rice CM. Flaviviridae: The viruses and their replication. Field Virology, Third Edition Lippincott-Raven Publishers, Philadelphia 1996; 931–959.
20. Houghton M. Hepatitis C viruses. Field Virology, Third Edition Lippincott-Raven Publishers, Philadelphia 1996; 1035–1058.
21. Collett M S, Larson R, Gold C, Strick D, Anderson D K and Purchio A F. Molecular cloning and nucleotide sequence of the pestivirus Bovine Viral Diarrhea virus. Virology 1988; 165:191–199.
22. Alter, M. J. (1997). Hepatology 26, 62S–65S.
23. Blight, K. J. and Rice, C. M. (1997). J. Virol. 71, 7345–7352.
24. Brechot, C. (1997). Hepatology 25, 772–774.
25. Bukh, J., Emerson, S. U. and Purcell, R. H. (1997). Genetic heterogeneity of hepatitis C virus and related viruses. In "Viral Hepatitis and Liver Disease, Proceedings of IX Triennial International Symposium on Viral Hepatitis and Liver Disease, Rome, Italy, 1996" (M. Rizzetto, R. H. Purcell, J. L. Gerin and G. Verme, Eds.), pp. 167–175. Edizioni Minerva Medica, Turin.
26. Bukh, J., Miller, R. H. and Purcell, R. H. (1995). Genetic heterogeneity of hepatitis C virus: quasispecies and genotypes. Semin. Liver Dis. 15, 41–63.
27. Bukh, J., Purcell, R. H. and Miller, R. H. (1993). At least 12 genotypes of hepatitis C virus predicted by sequence analysis of the putative E1 gene of isolates collected worldwide. Proc. Natl. Acad. Sci. USA 90, 8234–8238.
28. Davis, G. L., Esteban-Mur, R., Rustgi, V., Hoefs, J., Gordon, S. C., Trepo, C., Shiffman, M. L., Zeuzem, S., Craxi, A., Ling, M.-H. and Albrecht, J., for the international hepatits interventional therapy group. (1998). Interferon alfa-2b alone or in combination with ribavirin for the treatment of relapse of chronic hepatitis C. N. Engl. J. Med. 339, 1493–1499.
29. Forns, X. and Bukh, J. (1998). Methods for determining the hepatitis C virus genotype. Viral Hepatitis Reviews 4, 1–19.
30. Hijikata, M., Kato, N., Ootsuyama, Y., Nakagawa, M., Ohkoshi, S. and Shimotohno, K. (1991). Hypervariable regions in the putative glycoprotein of hepatitis C virus. Biochem. Biophys. Res. Commun. 175, 220–228.
31. Honda, M., et al. (1996). RNA 2, 955–968.
32. Hoofnagle, J. H. (1997). Hepatitis C: the clinical spectrum of disease. Hepatology 26, 15S–20S.
33. Ito, T. and Lai, M. M. C. (1997). J. Virol. 71, 8698–8706.
34. Kolykhalov, A. A., Feinstone, S. M. and Rice, C. M. (1996). Identification of a highly conserved sequence element at the 3' terminus of hepatitis C virus genome RNA. J. Virol. 70, 3363–3371.
35. McHutchison, J. G., Gordon, S. C., Schiff, E. R., Shiffman, M. L., Lee, W. M., Rustgi, V. K., Goodman, Z. D., Ling, M.-H., Cort, S. and Albrecht, J. K., for the hepatits interventional therapy group. (1998). Interferon alfa-2b alone or in combination with ribavirin as initial treatment for chronic hepatitis C. N. Engl. J. Med. 339, 1485–1492.
36. Okamoto, H., Kurai, K., Okada, S. I., Yamamoto, K., Iizuka, H., Tanaka, T., Fukuda, S., Tsuda, F. and Mishiro, S. (1992). Full-length sequence of hepatitis C virus genome having poor homology to reported isolates: comparative study of four distinct genotypes. Virology 188, 331–341.
37. Simmonds, P., Holmes, E. C., Cha, T.-A., Chan, S.-W., McOmish, F., Irvine, B., Beall, E., Yap, P. L., Kolberg, J. and Urdea, M. S. (1993). Classification of hepatitis C virus into six major genotypes and a series of subtypes by phylogenetic analysis of the NS-5 region. J. Gen. Virol. 74, 2391–2399.
38. Tanaka, T., Kato, N., Cho, M.-J. and Shimotohno, K. (1995). A novel sequence found at the 3' terminus of hepatitis C virus genome. Biochem. Biophys. Res. Commun. 215, 744–749.
39. Tanaka, T., Kato, N., Cho, M.-J., Sugiyama, K. and Shimotohno, K. (1996). Structure of the 3' terminus of the hepatitis C virus genome. J. Virol. 70, 3307–3312.
40. Tsuchihara, K., et al. (1997) J. Virol. 71, 6720–6726.
41. Tsukiyama-Kohara, K., et al. (1992) J. Virol. 66, 1476–1483.
42. Weiner, A. J., Brauer, M. J., Rosenblatt, J., Richman, K. H., Tung, J., Crawford, K., Bonino, F., Saracco, G., Choo, Q.-L., Houghton, M. and Han, J. H. (1991). Variable and hypervariable domains are found in the regions of HCV corresponding to the Flavivirus envelope and NS1 proteins and the Pestivirus envelope glycoproteins. Virology 180, 842–848.
43. Yamada, N., Tanihara, K., Takada, A., Yorihuzi, T., Tsutsumi, M., Shimomura, H., Tsuji, T. and Date, T. (1996). Genetic organization and diversity of the 3' noncoding region of the hepatitis C virus genome. Virology 223, 255–261.

What is claimed is:

1. A nucleic acid molecule comprising a chimeric virus genome, said genome being a bovine viral diarrhea virus (BVDV) genome in which at least one gene from the structural region of the BVDV genome has been replaced by the corresponding gene from the structural region of a hepatitis C virus genome.

2. The nucleic acid molecule of claim 1, wherein the structural region of the BVDV genome has been replaced by the structural region of the hepatitis C virus genome.

3. The nucleic acid molecule of claim 1, wherein the gene from the structural region is selected from the group consisting of E1, E2, or C.

4. The nucleic acid molecule of claim 1, wherein the E1 and E2 genes from the structural region of the BVDV genome have been replaced by the E1 and E2 genes of a hepatitis C virus genome.

5. The nucleic acid molecule of claim 1, wherein the E2 gene from the structural regions of the BVDV genome has been replaced by the E2 gene of a hepatitis C virus genome.

6. A DNA construct comprising the nucleic acid molecule of claim 1.

7. An RNA transcript of the DNA construct of claim 6.

8. An isolated host cell transfected with the DNA construct of claim 6.

9. An isolated host cell transfected with the RNA transcript of claim 7.

10. A chimeric HCV-BVDV virus produced by transfecting a host cell infected by BVDV with the DNA construct of claim 6.

11. A chimeric HCV-BVDV virus produced by transfecting a host cell infected by BVDV with the RNA transcript of claim 7.

12. An isolated cell infected with the virus of claim 10.

13. An isolated cell infected with the virus of claim 11.

14. A composition comprising the virus of claim 10 or 11 in a suitable excipient, diluent or carrier.

15. The nucleic acid molecule of claim 1, wherein the hepatitis C virus genome is an infectious hepatitis C virus genome.

* * * * *